US009783618B2

(12) United States Patent
Friedrich et al.

(10) Patent No.: US 9,783,618 B2
(45) Date of Patent: Oct. 10, 2017

(54) MANIPULATION OF IMMUNOGLOBULIN GENE DIVERSITY AND MULTI-ANTIBODY THERAPEUTICS

(71) Applicant: Kymab Limited, Cambridge (GB)

(72) Inventors: Glenn Friedrich, Cambridge (GB); E-Chiang Lee, Cambridge (GB); Jasper Clube, Cambridge (GB); Nicholas England, Cambridge (GB)

(73) Assignee: Kymab Limited, Cambridge (GB)

( * ) Notice: Subject to any disclaimer, the term of this patent is extended or adjusted under 35 U.S.C. 154(b) by 0 days.

(21) Appl. No.: 14/220,095

(22) Filed: Mar. 19, 2014

(65) Prior Publication Data

US 2015/0037337 A1 Feb. 5, 2015

Related U.S. Application Data

(60) Provisional application No. 61/818,121, filed on May 1, 2013.

(51) Int. Cl.
C12P 21/00 (2006.01)
C12N 15/00 (2006.01)
C07K 16/46 (2006.01)
G01N 33/50 (2006.01)
G01N 33/569 (2006.01)
C07K 16/00 (2006.01)

(52) U.S. Cl.
CPC ............ C07K 16/468 (2013.01); C07K 16/00 (2013.01); G01N 33/5005 (2013.01); G01N 33/5052 (2013.01); G01N 33/569 (2013.01); C07K 2317/51 (2013.01); C07K 2317/515 (2013.01); C07K 2317/565 (2013.01)

(58) Field of Classification Search
None
See application file for complete search history.

(56) References Cited

U.S. PATENT DOCUMENTS

| | | | |
|---|---|---|---|
| 4,720,449 A | 1/1988 | Borror et al. ................. 430/338 |
| 5,169,939 A | 12/1992 | Gefter et al. ............. 530/387.3 |
| 5,545,807 A | 8/1996 | Surani et al. ...................... 800/2 |
| 5,633,425 A * | 5/1997 | Lonberg et al. ................ 800/18 |
| 5,770,429 A | 6/1998 | Lonberg et al. ........... 435/240.2 |
| 5,789,215 A | 8/1998 | Berns et al. ................ 435/172.3 |
| 5,939,598 A | 8/1999 | Kucherlapati et al. ......... 800/25 |
| 5,948,600 A | 9/1999 | Roschger et al. ............ 430/348 |
| 6,130,364 A * | 10/2000 | Jakobovits ............. C07K 16/00 435/326 |
| 6,162,963 A | 12/2000 | Kucherlapati et al. ......... 800/18 |
| 6,395,487 B1 | 5/2002 | Bradley et al. |
| 6,461,818 B1 | 10/2002 | Bradley et al. |
| 6,596,541 B2 † | 7/2003 | Murphy |
| 6,673,986 B1 | 1/2004 | Kucherlapati et al. ......... 800/18 |
| 6,713,610 B1 | 3/2004 | Kucherlapati et al. .. 530/388.23 |
| 6,833,268 B1 | 12/2004 | Green et al. ................ 435/320.1 |
| 6,914,128 B1 | 7/2005 | Salfeld et al. ............. 530/387.3 |
| 6,998,514 B2 | 2/2006 | Brüggemann ................... 800/18 |
| 7,119,248 B1 | 10/2006 | Rajewsky et al. ................ 800/6 |
| 7,205,140 B2 | 4/2007 | Gottschalk et al. |
| 7,205,148 B2 | 4/2007 | Economides et al. ........ 435/462 |
| 7,435,871 B2 | 10/2008 | Green et al. ..................... 800/18 |
| 7,501,552 B2 | 3/2009 | Lonberg et al. .................. 800/6 |
| 7,605,237 B2 | 10/2009 | Stevens et al. ............ 530/387.9 |
| 7,605,238 B2 * | 10/2009 | Korman et al. ......... 530/388.15 |
| 7,910,798 B2 | 3/2011 | Tanamachi et al. ........... 800/18 |
| 7,932,431 B2 | 4/2011 | Bruggemann .................. 800/18 |
| 8,158,419 B2 | 4/2012 | Lonberg et al. ............. 435/328 |
| 8,502,018 B2 | 8/2013 | Murphy et al. ................. 800/18 |
| 8,592,644 B2 | 11/2013 | Harriman et al. |
| 8,642,835 B2 | 2/2014 | MacDonald et al. .......... 800/16 |
| 8,697,940 B2 | 4/2014 | Macdonald et al. |
| 8,877,901 B2 * | 11/2014 | Govindan ........ A61K 47/48384 530/387.1 |

(Continued)

FOREIGN PATENT DOCUMENTS

| | | | | |
|---|---|---|---|---|
| CA | 2 307 503 A1 | 11/2001 | ............. A61K 39/42 |
| DE | 10251918 A1 | 5/2004 | |

(Continued)

OTHER PUBLICATIONS

Kawasaki et al. Genome Res 1997;7:250-61.*
Polyclonal Antibodies Wikipedia, 2008.*
Monoclonal antibodies, Wikipedia, 2008.*
Kawasaki et al. Genome Res 1997;7:250-61. Provided on Jun. 28, 2016.*
Polyclonal Antibodies Wikipedia, 2008. Provided on Jun. 28, 2016.*
Monoclonal antibodies, Wikipedia, 2008. Provided on Jun. 28, 2016.*

(Continued)

Primary Examiner — Janice Li

(74) Attorney, Agent, or Firm — Sunstein Kann Murphy & Timbers LLP

(57) ABSTRACT

The invention provides improved non-human vertebrates and non-vertebrate cells capable of expressing antibodies comprising human variable region sequences. The present invention is directed to the provision of long HCDR3s from non-human vertebrates and cells. The present invention is also directed to the provision of novel V, D and J pairings in immunoglobulin heavy and light chain loci. Novel, biased antibody diversities and potentially expanded diversities are provided. The invention also provides for novel and potentially expanded diversity or diversity that is biased towards variable gene usage common to antibodies useful for treating and/or preventing certain diseases or conditions, such as infectious diseases. The invention also provides methods of generating antibodies using such vertebrates, as well as the antibodies per se, therapeutic compositions thereof and uses.

12 Claims, 9 Drawing Sheets

(56) References Cited

U.S. PATENT DOCUMENTS

| | | | |
|---|---|---|---|
| 9,253,965 B2 | 2/2016 | Bradley et al. | |
| 2002/0088016 A1 | 7/2002 | Bruggemann | 800/18 |
| 2002/0183275 A1 | 12/2002 | Murphy et al. | |
| 2003/0108925 A1 | 6/2003 | Dix et al. | 435/6 |
| 2003/0217373 A1 | 11/2003 | Green et al. | 800/6 |
| 2004/0231012 A1 | 11/2004 | Bruggemann | |
| 2005/0048621 A1 | 3/2005 | Grasso et al. | 435/69.1 |
| 2006/0015949 A1 | 1/2006 | Lonberg et al. | 800/5 |
| 2006/0015957 A1 | 1/2006 | Lonberg et al. | 800/18 |
| 2006/0021074 A1 | 1/2006 | Kellermann et al. | 800/18 |
| 2006/0199204 A1 | 9/2006 | Dix et al. | 800/16 |
| 2007/0280945 A1 | 12/2007 | Stevens et al. | 424/145.1 |
| 2008/0098490 A1 | 4/2008 | Jakobovits et al. | A01K 67/00 |
| 2009/0083870 A1 | 3/2009 | Horn et al. | 800/13 |
| 2009/0196112 A1 | 8/2009 | Cho | 365/200 |
| 2009/0209036 A1 | 8/2009 | Reynaud et al. | 435/455 |
| 2010/0011450 A1 | 1/2010 | Garcia et al. | |
| 2010/0069614 A1 | 3/2010 | Houtzager et al. | 530/387.1 |
| 2010/0146647 A1 | 6/2010 | Logtenberg et al. | 800/4 |
| 2010/0196367 A1 | 8/2010 | Day | 424/130.1 |
| 2010/0330676 A1 | 12/2010 | Horowitz et al. | |
| 2011/0138489 A1 | 6/2011 | Tanamachi et al. | 800/6 |
| 2011/0145937 A1 | 6/2011 | MacDonald et al. | 800/6 |
| 2011/0195454 A1† | 8/2011 | McWhirter | |
| 2011/0236378 A1 | 9/2011 | Green et al. | 424/133.1 |
| 2011/0283376 A1 | 11/2011 | Murphy et al. | |
| 2012/0070861 A1 | 3/2012 | Macdonald et al. | 435/91.1 |
| 2012/0073004 A1 | 3/2012 | Macdonald et al. | 800/18 |
| 2012/0167237 A1 | 6/2012 | Bradley et al. | 800/9 |
| 2012/0204278 A1 | 8/2012 | Bradley et al. | 800/18 |
| 2012/0233715 A1 | 9/2012 | Kuroiwa et al. | 800/3 |
| 2012/0322108 A1 | 12/2012 | Macdonald et al. | 435/69.6 |
| 2013/0039850 A1 | 2/2013 | Lonberg et al. | 424/1.49 |
| 2013/0102031 A1 | 4/2013 | King et al. | 435/69.6 |
| 2013/0160153 A1 | 6/2013 | Macdonald et al. | 800/18 |
| 2013/0198879 A1 | 8/2013 | McWhirter et al. | |
| 2013/0212719 A1 | 8/2013 | Macdonald et al. | 800/6 |
| 2013/0254911 A1 | 9/2013 | Macdonald et al. | 800/18 |
| 2013/0263293 A1 | 10/2013 | Bradley et al. | C07K 16/46 |
| 2013/0323790 A1 | 12/2013 | Macdonald et al. | 435/70.2 |
| 2013/0323791 A1 | 12/2013 | Macdonald et al. | 435/91.1 |
| 2013/0326647 A1 | 12/2013 | Macdonald et al. | 800/18 |
| 2013/0333057 A1 | 12/2013 | Macdonald et al. | 800/6 |
| 2014/0017228 A1 | 1/2014 | Macdonald et al. | 424/132.1 |
| 2014/0130193 A1 | 5/2014 | Macdonald et al. | 800/18 |
| 2014/0130194 A1 | 5/2014 | Macdonald et al. | 800/18 |
| 2014/0137275 A1 | 5/2014 | Macdonald et al. | 800/18 |
| 2014/0213773 A1 | 7/2014 | Macdonald et al. | 530/387.3 |
| 2014/0331344 A1 | 11/2014 | Friedrich et al. | A01K 67/027 |

FOREIGN PATENT DOCUMENTS

| | | | | |
|---|---|---|---|---|
| EP | 1780272 A1 | 5/2007 | | C12N 15/00 |
| EP | 2550363 | 10/2012 | | C12N 15/85 |
| EP | 2 421 357 | 1/2013 | | A01K 67/027 |
| GB | 2398784 A | 9/2004 | | A01K 67/027 |
| GB | 2403475 A | 1/2005 | | |
| KR | 102050042792 A | 5/2005 | | A01K 67/027 |
| WO | WO 90/04036 | 4/1990 | | C12P 21/08 |
| WO | WO 91/00906 | 1/1991 | | C12N 15/00 |
| WO | WO 91/10741 | 7/1991 | | C12P 21/06 |
| WO | WO 93/12227 | 6/1993 | | C12N 15/00 |
| WO | WO 94/02602 | 2/1994 | | C12N 15/00 |
| WO | WO 94/04667 | 3/1994 | | C12N 15/00 |
| WO | WO 96/30498 | 10/1996 | | C12N 15/00 |
| WO | WO 98/24884 | 6/1998 | | C12N 5/00 |
| WO | WO 98/24893 | 6/1998 | | C12N 15/00 |
| WO | WO 99/45962 | 9/1999 | | A61K 39/295 |
| WO | WO 02/08409 A2 | 1/2002 | | C12N 15/00 |
| WO | WO 02/36789 A2 | 5/2002 | | C12N 15/85 |
| WO | WO 02/43478 | 6/2002 | | A01K 67/027 |
| WO | WO 02/053596 A2 | 7/2002 | | C07K 16/28 |
| WO | WO 02/059263 A2 | 8/2002 | | |
| WO | WO 02/066630 A1 | 8/2002 | | C12N 15/00 |
| WO | WO 02/070648 A2 | 9/2002 | | |
| WO | WO 03/006639 A1 | 1/2003 | | C12N 5/10 |
| WO | WO 03/047336 A2 | 6/2003 | | |
| WO | WO 03/061363 A2 | 7/2003 | | |
| WO | WO 2004/050838 A2 | 6/2004 | | |
| WO | WO 2005/003364 A2 | 1/2005 | | C12N 15/90 |
| WO | WO-2005004592 A2 | 1/2005 | | |
| WO | WO 2005/019463 A1 | 3/2005 | | C12N 15/85 |
| WO | WO-2005058815 A2 | 6/2005 | | |
| WO | WO 2006/044492 | 4/2006 | | C12N 15/52 |
| WO | WO-2006055704 A2 | 5/2006 | | |
| WO | WO-2006068953 A2 | 6/2006 | | |
| WO | WO 2006/122442 A1 | 11/2006 | | C12N 9/22 |
| WO | WO 2007/096779 A2 | 8/2007 | | |
| WO | WO 2007/117410 A2 | 10/2007 | | A01K 67/027 |
| WO | WO-2007143168 A2 | 12/2007 | | |
| WO | WO 2008/022391 A1 | 2/2008 | | C07K 16/28 |
| WO | WO 2008/054606 A2 | 5/2008 | | C07K 16/00 |
| WO | WO 2008/070367 A2 | 6/2008 | | C12N 15/09 |
| WO | WO 2008/076379 A2 | 6/2008 | | C07K 16/18 |
| WO | WO 2008/094178 A2 | 8/2008 | | C12Q 1/68 |
| WO | WO 2008/103474 A1 | 8/2008 | | C12N 15/13 |
| WO | WO 2008/118970 A2 | 10/2008 | | A61K 48/00 |
| WO | WO 2008/122886 A2 | 10/2008 | | C12N 15/85 |
| WO | WO 2008/151081 A1 | 12/2008 | | C12N 15/13 |
| WO | WO 2009/013620 A2 | 1/2009 | | |
| WO | WO 2009/018411 A1 | 2/2009 | | C07K 16/28 |
| WO | WO 2009/023540 A1 | 2/2009 | | A61K 39/395 |
| WO | WO 2009/076464 A2 | 6/2009 | | C12N 15/09 |
| WO | WO 2009/080254 A1 | 7/2009 | | C07K 16/46 |
| WO | WO 2009/094178 A2 | 7/2009 | | C09B 67/08 |
| WO | 2009/129247 A2 † | 10/2009 | | |
| WO | WO 2009/118524 A2 | 10/2009 | | C12N 5/00 |
| WO | WO-2009129247 A2 | 10/2009 | | |
| WO | 2009/143472 A2 † | 11/2009 | | |
| WO | WO 2009/143472 A2 | 11/2009 | | C07K 16/46 |
| WO | WO 2009/157771 A2 | 12/2009 | | A01K 67/027 |
| WO | 2010/039900 A2 † | 4/2010 | | |
| WO | WO 2010/039900 A2 | 4/2010 | | C12N 15/13 |
| WO | WO 2010/070263 A1 | 6/2010 | | C12N 15/85 |
| WO | WO-2010077854 A1 | 7/2010 | | |
| WO | WO 2010/097385 A1 | 9/2010 | | C07K 16/24 |
| WO | WO 2010/113039 A1 | 10/2010 | | C12N 5/00 |
| WO | WO 2011/004192 A1 | 1/2011 | | A01K 67/027 |
| WO | WO 2011/008093 A1 | 1/2011 | | C07K 16/00 |
| WO | WO 2011/056864 A1 | 5/2011 | | C12P 21/06 |
| WO | WO 2011/062206 A1 | 5/2011 | | C12N 15/09 |
| WO | WO-2011062207 A1 | 5/2011 | | |
| WO | WO-2011071957 A1 | 6/2011 | | |
| WO | WO 2011/097603 A1 | 8/2011 | | C12N 15/85 |
| WO | WO-2011146121 A1 | 11/2011 | | |
| WO | 2011/163311 A1 † | 12/2011 | | |
| WO | WO 2011/158009 A1 | 12/2011 | | A01K 67/027 |
| WO | WO 2011/163311 A1 | 12/2011 | | C12N 15/85 |
| WO | WO 2011/163314 A1 | 12/2011 | | C12N 15/85 |
| WO | WO 2012/018764 A1 | 2/2012 | | C12N 15/85 |
| WO | WO 2012/023053 A2 | 2/2012 | | |
| WO | WO 2012/141798 A1 | 10/2012 | | C12N 15/85 |
| WO | WO 2012/148873 A2 | 11/2012 | | A01K 67/027 |
| WO | WO 2013/022782 A1 | 2/2013 | | C12N 15/85 |
| WO | WO 2013/041844 A2 | 3/2013 | | C12N 15/85 |
| WO | WO 2013/041845 A2 | 3/2013 | | C12N 15/85 |
| WO | WO 2013/059230 A1 | 4/2013 | | C12N 15/85 |
| WO | WO 2013/061098 A2 | 5/2013 | | C12N 15/85 |
| WO | WO 2013/096142 | 6/2013 | | A01K 67/027 |
| WO | WO 2013/116609 A1 | 8/2013 | | A01K 67/027 |
| WO | WO-2013176772 A1 | 11/2013 | | |
| WO | WO-2014093622 A2 | 6/2014 | | |

OTHER PUBLICATIONS

Grippo et al. J Immunol 2009;183 :8015-25.*
Wang et al. Immunogenetic 2012;64:713-7.*
Arnaout et al., "High-Resolution Description of Antibody Heavy-Chain Repertoires in Humans," Public Library of Science ONE, vol. 6, Issue 8, pp. 1-8, Aug. 2011.
Atlas Genetics Oncology, "Atlas of Genetics and Cytogenetics in Oncology and Hematology: VPREB1," Accessed Online: <http://

(56) References Cited

OTHER PUBLICATIONS atlasgeneticsoncology.org/Genes/GC_VPREB1.html> on May 25, 2015, 5 pages.
Baker et al., "Adaptation of TCR Expression Vectors for the Construction of Mouse-Human Chimeric MBP-Specific TCR Transgenes," Journal of Neuroscience Research, vol. 45, No. 4, pp. 487-491. Aug. 15, 1996.
Bode et al., "The Transgeneticist's Toolbox: Novel Methods for the Targeted Modification of Eukaryotic Genomes," Biological Chemistry, vol. 381, No. 9-10, pp. 801-813, Sep.-Oct. 2000.
Bransteitter et al., "Activation-Induced Cytidine Deaminase Deaminates Deoxcytidine on Single-Stranded DNA But Requires the Action of RNase," Proceedings of the National Academy of Sciences of the United States of America, vol. 100, No. 7, pp. 4102-4107, Apr. 1, 2003.
Bruggemann, "Human Monoclonal Antibodies from Translocus Mice," Molecular Biology of B Cells, Chapter 34, pp. 547-561, 2003.
Butler, "Immunoglobulin Diversity, B-Cell and Antibody Repertoire Development in Large Farm Animals," Revue Scientifique et Technique (Paris), vol. 17, No. 1, pp. 43-70, Apr. 1998.
Davies et al., "Creation of Mice Expressing Human Antibody Light Chains by Introduction of a Yeast Artificial Chromosome Containing the Core Region of the Human Immunoglobulin λ Locus," Nature Biotechnology, vol. 11, No. 8, pp. 911-914, Sep. 1993.
de Bono et al., "VH Gene Segments in the Mouse and Human Genomes," Journal of Molecular Biology, vol. 342, No. 1, pp. 131-143, Sep. 3, 2004.
Edwards et al., "The ADAM Metalloproteinases," Molecular Aspects of Medicine, vol. 29, No. 5, pp. 258-289, Oct. 2008.
Feng et al., "Site-Specific Chromosomal Integration in Mammalian Cells: Highly Efficient CRE Recombinase-Mediated Cassette Exchange," Journal of Molecular Biology, vol. 292, No. 4, pp. 779-785, Oct. 1, 1999.
Gama Sosa et al., "Animal Transgenesis: An Overview", Brain Structure & Function, vol. 214, No. 2-3, pp. 91-109, Mar. 2010.
GenBank, Rattus norvegicus clone CH230-30N12 Sequencing in Progress 6—Nucleotide, accessed Mar. 9, 2015, 42 pages.
GenBank, GenBank Accession No. x97051.1 S64822, DNA Sequence of the Human Immunoglobulin D Segment Locus, 26 pages, Mar. 3, 2015.
GenBank, Mus Musculus Strain 129S1/SvImJ Chromosome 12 Genomic Scaffold, GRCm38—Nucleotide—NCBI, GenBank Accession No. NT_114985, Dec. 27, 2013, 1 page.
Harding et al., Class Switching in Human Immunoglobulin Transgenic Mice, Annals of New York Academy of Science, vol. 764, pp. 536-546, Sep. 29, 1995.
Huber et al., Distinct Contributions of Vaccine-Induced Immunoglobulin G1 (IgG1) and IgG2a Antibodies to Protective Immunity against Influenza, Clinical and Vaccine Immunology, vol. 13, No. 9, pp. 981-990, Sep. 2006.
Janeway et al., Structural Variation in Immunoglobulin Constant Regions, Immunobiology: The Immune System in Health and Disease. 5th Edition, New York: Garland Science, 2001.
Janeway et al., The Rearrangement of Antigen-Receptor Gene Segments Controls Lymphocyte Development, in Immunobiology, 5th edition, 13 pages, Aug. 14, 2015 (retrieved online at <http://www.ncbi.nlm.nih.gov/books/NBK27113/>).
Kaushik et al., "Novel Insight Into Antibody Diversification From Cattle," Veterinary Immunology and Immunopathology, vol. 87, No. 3-4, pp. 347-350, Sep. 10, 2002.
Kim et al., "Expression and Relationship of Male Reproductive Adams in Mouse," Biology of Reproduction, vol. 74, No. 4, pp. 744-750, Apr. 2006.
Lefrenc et al., The Immunoglobulin Facts Book, Academic Press, ISBN:978-0-08-057447, May 29, 2001.
Little et al., "Generation of a Large Complex Antibody Library From Multiple Donors," Journal of Immunology Methods, vol. 231, No. 1-2, pp. 3-9 , Dec. 10, 1999.

Macdonald et al., "Velocigene Technology Extended to Humanization of Several Megabases of Complex Gene Loci," (Abstract) 1st International MUGEN Conference on Animal Models for Human Immunological Dissease, Athens Greece, 1 page ,Sep. 10-13, 2006.
Matthews et al., "A Locus Affecting Immunoglobulin Isotype Selection (Igis1) Maps to the MHC Region in C57BL, BALB/C and NOD Mice," Immunology and Cell Biology, vol. 79, No. 6, pp. 576-582, Dec. 2001.
Parng et al., "Gene Conversion Contributes to Ig Light Chain Diversity in Cattle," The Journal of Immunology, vol. 157, No. 12, pp. 5478-5486, Dec. 15, 1996.
Qi et al., "A New Transgenic Rat Model of Hepatic Steatosis and the Metabolic Syndrome," Hypertension, vol. 45, No. 5, pp. 1004-1011, May 2005.
Ramirez-Solis et al., "Chromosome Engineering in Mice," Nature, vol. 378, No. 6558, pp. 720-724, Dec. 14, 1995.
Ramsden et al., "Conservation of Sequence in Recombination Signal Sequence Spacers," Nucleic Acids Research, vol. 22, No. 10, pp. 1785-1796, Apr. 13, 1994.
Ristevski, "Making Better Transgenic Models, Molecular Biotechnology," vol. 29, No. 2, pp. 153-163, Feb. 2005.
Rosner et al., "Third Complementarity-Determining Region of Mutated VH Immunoglobulin Genes Contains Shorter V, D, J, P, and N Components Than Non-Mutated Genes," Immunology, vol. 103, No. 2, pp. 179-187, Jun. 2001.
Rusk, "Making Mice at High Speed," Nature Methods, vol. 4, No. 3, pp. 196-197, Mar. 2007.
Schultz et al., "Humanized Mice in Translational Biomedical Research," Nature Reviews Immunology, vol. 7, No. 2, pp. 118-130. Feb. 2007.
Shi et al., "The Mapping of Transgenes by Fluorescence In Situ Hybridization on G-Banded Mouse Chromosomes," Mammalian Genome, vol. 5, No. 6, pp. 337-341, Jun. 1994.
Shih, "Discovery Process for Antibody-Based Therapeutics," Development of Antibody-Based Therapeutics, Chapter 2, pp. 9-32, Apr. 24, 2012.
Smith, "Gene Transfer in Higher Animals: Theoretical Considerations and Key Concepts," Journal of Biotechnology, vol. 99, No. 1, pp. 1-22, Oct. 9, 2002.
Stevens et al., "Velocimmune: Humanization of Immunoglobulin Loci Using Velocigene Technology," (Abstract) Presented at 1st International MUGEN Conference on Animal Models for Human Immunological Disease, Athens, Greece, 1 page, Sep. 10-13, 2006.
Takeda et al., "Construction of Chimaeric Processed Immunoglobulin Genes Containing Mouse Variable and Human Constant Region Sequences," Nature, vol. 314, pp. 452-454, Apr. 4, 1985.
The Jackson Laboratory, Breeding Strategies for Maintaining Colonies of Laboratory Mice, A Jackson Laboratory Resource Manual, pp. 1-29, 2007.
Tonegawa, "Somatic Generation of Antibody Diversity," Nature, vol. 302, No. 5909, p. 575-581, Apr. 14, 1983.
van Snick et al., "Genetic Control of Rheumatoid Factor Production in the Mouse," Arthritis & Rheumatism, vol. 26, No. 9, pp. 1085-1090, Sep. 1983.
Wagner, "Antibodies Generated From Human Immunoglobulin Miniloci in Transgenic Mice," Nucleic Acids Research, vol. 22, No. 8, pp. 1389-1393, Apr. 25, 1994.
Waterston et al., "Initial Sequencing and Comparative Analysis of the Mouse Genome," Nature, vol. 420, No. 6915, pp. 520-562, Dec. 2002.
Zemlin et al., Expressed Murine and Human CDR-H3 Intervals of Equal Length Exhibit Distinct Repertoires that Differ in their Amino Acid Composition and Predicted Range and Structures, Journal of Molecular Biology, vol. 334, No. 4, pp. 733-749, Dec. 5, 2003.
European Patent Office, International Search Report—International Application No. PCT/GB2012/052298, dated Jun. 13, 2013, together with the Written Opinion of the International Searching Authority, 22 pages.
European Patent Office, International Search Report—International Application No. PCT/GB2010/051122, dated Sep. 29, 2010, 3 pages.

(56) References Cited

OTHER PUBLICATIONS

European Patent Office, International Search Report, Application No, PCT/GB2012/052296, dated May 17, 2013, together with the Written Opinion of the International Searching Authority, 30 pages.
European Patent Office, European Search Report, Application EP 12194977, dated Jul. 5 2013, 4 pages.
European Patent Office, International Search Report, Application No. PCT/GB2012/052956, 8 pages, dated Mar. 1, 2013.
European Patent Office, International Search Report, Application No. PCT/GB2013/051280, 19 pages, dated Nov. 15, 2013, together with the Written Opinion of the International Searching Authority.
European Patent Office, International Search Report—International Application No. PCT/GB2013/050682, dated Sep. 25, 2013, together with the Written Opinion of the International Searching Authority, 17 pages.
European Patent Office, European Search Report, Application No. EP 12195041.4, dated Nov. 18, 2013, 8 pages.
European Patent Office, Extended European Search Report, Application No. EP14176740.0, 7 pages, dated Oct. 15, 2014.
European Patent Office, Extended European Search Report, Application No. EP12171791.2, 5 pages, dated Jun. 18, 2013.
France IP Office, International Search Report, Application No. FR 1359518, 3 pages, dated Aug. 20, 2014.
European Patent Office Munich, Extended European Search Report, Application No. 14196645.7, 12 pages, dated Jun. 26, 2015.
United Kingdom IP Office, Combined Search and Examination Report under Sections 17 and 18(3), Application No. GB1317447.9, 7 pages, dated Jan. 14, 2014.
Dr. Mathias Ricker, Opposition against EP2421357 B1 in the name of Kymab Limited Statement of Facts and Arguments pertaining to Application No. 10734546.4, 29 pages, dated Oct. 23, 2013.
European Patent Office, Opposition against EP2421357 Animal Models and Therapeutic Molecules in the name of Kymab Limited pertaining to Application No. 10734546.4, 44 pages, dated Oct. 23, 2013.
European Patent Office, Statement of Fact and Arguments in Support of Opposition pertaining to Application No. 10734546.4, 41 pages, dated Oct. 22, 2013.
European Patent Office, Opposition against EP2421357 pertaining to Appl. No. EP 10734546.4, 41 pages, dated Jan. 23, 2013.
Grund IP Office, Third Party Observation in PCT/GB2012/052960, 3 pages, dated Apr. 2, 2014.
Grund IP Group, Third-Party Observations according to Article 115 EPC regarding EP 11705964.2, 5 pages, dated. Feb. 26, 2015.
Grund IP Group, Third-Party Observations according to Article 115 EPC regarding EP 11705964.2, 4 pages, dated Apr. 30, 2014.
Grund IP Group, Third-Party Observations according to Article 115 EPC regarding EP 11705964.2, 8 pages, dated Oct. 9, 2013.
Grund IP Group, Third-Party Observations according to Article 115 EPC regarding EP 12171791.2, 9 pages, dated Feb. 26, 2014.
Grund IP Group, Third-Party Observations according to Article 115 EPC regarding EP 12171791.2, 6 pages, dated Aug. 4, 2014.
Grund IP Group, Third-Party Observations according to Article 115 EPC regarding EP 12171793.8, 7 pages, dated Jun. 25, 2014.
Grund IP Group, Third-Party Observations according to Article 115 EPC regarding EP 12194970.5, dated Mar. 5, 2014.
Grand IP Group, Third-Party Observations according to Article 115 EPC regarding EP 12194970.5, 5 pages, dated Aug. 12, 2014.
Grund IP Group, Third-Party Observations according to Article 115 EPC regarding EP 12194977.0, 4 pages, dated Mar. 26, 2014.
Grund IP Office, Third-Party Observations according to Article 115 EPC regarding EP 12194977.0, 5 pages, dated May 12, 2015.
Grund IP Group, Third-Party Observations according to Article 115 EPC regarding EP 12195041.4, 5 pages, dated Jul. 30, 2014.
Grund IP Group, Third-Party Observations according to Article 115 EPC regarding EP 12795606.8, 6 pages, dated Feb. 26, 2014.
Grund IP Group, Third-Party Observations according to Article 115 EPC regarding EP 12795606.8, 4 pages, dated Mar. 26, 2015.

Dr. Martin Grund, Grund IP Group, Third Party Observation regarding Application No. PCT/GB2013/050682, 3 pages, dated Jul. 28, 2014.
Grund IP Group, Third Party Observation regarding PCT/GB2013/050683, 2 pages, dated Jul. 28, 2014.
Martin Grund, Third Party Observation Application No. PCT/GB2012/052297, 3 pages, dated Jan. 17 2014.
Martin Grund, Third Party Observation Application PCT/GB2012/052298, 4 pages, dated Jan. 17, 2014.
Martin Grund, Third Party Observation Application No. PCT/GB2012/052380, 4 pages, dated Jan. 24, 2014.
Kymab Ltd., Third Party Observation regarding Application PCT/US2012/026416, 2 pages, dated Jun. 7, 2013.
Grund IP Group, Third Party Observations according to Article 115 EPC regarding EP12171791.2, 7 pages, dated Dec. 19, 2014.
Grund IP Group, Third Party Observations according to Article 115 EPC regarding EP12194970.5, 6 pages, dated Apr. 25, 2014.
Grund IP Group, Third Party Observations according to Article 115 EPC regarding EP12194970.5, 6 pages, dated Nov. 15, 2013.
Grund IP Group, Third Party Observations according to Article 115 EPC regarding EP12772122.3, 5 pages, dated Mar. 12, 2015.
Grund IP Group, Third Party Observations according to Article 115 EPC regarding EP14176740.0, 13 pages, dated Aug. 10, 2015.
Charles E. Lyon, Third-Party Pre-Issuance Submission Under 37 CFR 1.290 in U.S. Appl. No. 14/040,405, 18 pages, dated Jan. 16, 2015.
Excerpts from U.S. Appl. No. 14/682,859, filed Apr. 9, 2015, including Applicant initiated Interview Summary; Amendments to the Claims; and Information Disclosure Statement, 14 pages.
Declaration of Lynn E. MacDonald, Declaration of Lynn E. MacDonald with Exhibits, dated Feb. 3, 2015 relating to International Patent Application No. PCT/US02/04500, Published as WO 02/066630 A1, 13 pages.
Declaration of Andrew J. Murphy, Declaration of Andrew J. Murphy, dated Oct. 6, 2014, including Slide Presentation dated Nov. 3, 2009, at Wellcome Trust Advanced Course: Genetic Manipulation of ES Cells, in Hinxton, UK, entitled "BAC-based Modifications of the Mouse Genuine: The Big and the Backward", cited in and IDS in U.S. Appl. No. 14/192,051 of MacDonald et al. 62 pages.
U.S. Appl. No. 13/434,361, filed Mar. 29, 2012.
Adams, D., et al., "A Genome-Wide, End-Sequenced 129Sv BAC Library Resource for Targeting Vector Construction," Genomics, vol. 86, pp. 753-758, 2005.
Askew, R., et al., "Site-Directed Point Mutations in Embryonic Stem Cells: a Gene-Targeting Tag-and-Exchange Strategy," Molecular and Cellular Biology, pp. 4115-4124, Jul. 1993.
Auerbach, et al., "Establishment and Chimera Analysis of 129/Svev- and C57BL/6-Derived Mouse Embryonic Stem Cell Lines," Biotechniques, vol. 29: pp. 1024-1032 (Nov. 2000).
Baker et al., "Homologous Recombination between Transferred and Chromosomal Immunoglobulin k Genes," Molecular and Cellular Biology, pp. 4041-4047, Oct. 1988.
Barreto et al., "AID From Bony Fish Catalyzes Class Switch Recombination," Journal of Experimental Medicine, pp. 1-6, Sep. 12, 2005.
Bates et al., "Chromosomal Position of a VH Gene Segment Determines Its Activation and Inactivation as a Substrate for V(D)J Recombination," The Journal of Experimental Medicine, vol. 204, No. 13, pp. 3247-3256, Dec. 24, 2007.
Beard, et al., "Efficient Method to Generate Single-Copy Transgenic Mice by Site-Specific Integration in Embryonic Stem Cells," Genesis, vol. 44, No. 1, pp. 23-28, Jan. 2006.
Beck et al., "Nucleotide Sequence and Exact Localization of the Neomycin Phosphotransferase Gene From Transposon Tn5". Gene, vol. 19, pp. 327-336, Oct. 1982.
Berg et al., "Inverted Repeats of Tn5 Are Transposable Elements", Proceedings of National Academy of Sciences USA, Genetics, vol. 79, pp. 2632-2635, Apr. 1982.
Bethke et al., "Segmental Genomic Replacement by Cre-Mediated Recombination: Genotoxic Stress Activation of the P53 Promoter in Single-Copy Transformants," Nucleic Acids Research, vol. 25, No. 14, pp. 2828-2834, 1997.

(56) References Cited

OTHER PUBLICATIONS

Bhattacharya, et al., "Switch Region Identity Plays an Important Role in Ig Class Switch Recombination," Journal of Immunology, vol. 184, pp. 6242-6248, Apr. 28, 2010.
Billiard, et al., "Ongoing Dll4-Notch Signaling Is Required for T-Cell Homeostasis in the Adult Thymus," European Journal of Immunology, vol. 41, pp. 2207-2216, Aug. 4, 2011.
Blankenstein, et al., "Immunoglobulin $V_H$ Region Genes of the Mouse are Organized in Overlapping Clusters," European Journal of Immunology, vol. 17, No. 9, pp. 1351-1357, Jul. 13, 1987.
Bogen, et al., "A Rearranged λ2 Light Gene Chain Retards But Does Not Exclude χ and λ1 Expression," vol. 21, No. 10, pp. 2391-2395, Oct. 1991.
Bolland et al., "Antisense Intergenic Transcription Precedes IghD-to-J Recombination and is Controlled by the Intronic Enhancer Eμ," Molecular and Cellular Biology, vol. 27, No. 15, pp. 5523-5533, Aug. 2007.
Bonin et al., "Isolation, Microinjection, and Transfer of Mouse Blastocysts" Methods in Molecular Biology, vol. 158, Gene Knockout Protocols, pp. 121-134, 2001.
Bottaro et al., "Deletion of the IgH Intronic Enhancer and Associated Matrix-Attachment Regions Decreases, but Does Not Abolish, Class Switching at the μ Locus," International Immunology. vol. 10, No. 6, pp. 799-806, Jun. 1998.
Bradley et al., "Formation of Germ-Line Chimaeras From Embryo-Derived Teratocarcinoma Cell Lines," Nature Publishing Group, vol. 309, pp. 255-256, May 17, 1984.
Breden et al., "Comparison of Antibody Repertoires Produced by HIV-1 Infection, Other Chronic and Acute Infections, and Systemic Autoimmune Disease," PloS One. vol. 6, Issue 3, pp. 1-11, Mar. 2011.
Brezinchek, et al., "Analysis of the Human $V_H$ Gene Repertoire," The American Society for Clinical Investigations, Inc., vol. 99, No. 10, pp. 2488-2501, May 1997.
Briney, et al., "Human Peripheral Blood Antibodies with Long HCDR3s Are Established Primarily at Original Recombination Using a Limited Subset of Germline Genes," Public Library of Science One, vol. 7, No. 5, e36750, 13 pages, May 9, 2012.
Brocker et al., "Evolutionary Divergence and Functions of the ADAM and ADAMTS Gene Families" Human Genomics, vol. 4, No. 2, pp. 43-55, Oct. 2009.
Brüggemann, et al, "Immunogenicity of Chimeric Antibodies," The Journal of Experimental Medicine, vol. 170, No. 6, pp. 2153-2157, Dec. 1, 1989.
Brüggemann, et al., "Human Antibody Production in Transgenic Mice: Expression From 100 Kb of the Human lgH Locus," European Journal of Immunology, vol. 21, Issue 5, pp. 1323-1326, May 1991.
Brüggemann, et al., "Strategies for Expressing Human Antibody Repertoires in Transgenic Mice," Immunology Today, vol. 17, No. 8, pp. 391-397, Aug. 1996.
Brüggemann, "Human Antibody Expression in Transgenic Mice," Archivum Immunologiae et Therapiae Experimentalis, vol. 49, pp. 203-208, 2001.
Brüggemann et al., "Immunoglobulin heavy chain locus of the rat: Striking homology to mouse antibody genes," Proceedings of the National Academy of Sciences USA, Immunology, vol. 83, pp. 6075-6079, Aug. 1986.
Brüggemann et al., "A repertoire of monoclonal antibodies with human heavy chains from transgenic mice," Proceedings of the National Academy of Sciences USA, Immunology, vol. 86, pp. 6709-6713, Sep. 1989.
Buehr et al., "Capture of Authentic Embryonic Stem Cells from Rat Blastocysts," Cell, vol. 135, pp. 1287-1298, Dec. 26, 2008.
Cadinanos et al., "Generation of an Inducible and Optimized Piggyback Transposon System," Nucleic Acids Research, vol. 35, No. 12, Jun. 18, 2007.
Carstea, et al., "Germline Competence of Mouse ES and Ips Cell Lines: Chimera Technologies and Genetic Background," World Journal of Stem Cells, vol. 1, No. 1, pp. 22-29, Dec. 31, 2009.

Chen et al., "B Cell Development in Mice That Lack One or Both Immunoglobulin χ Light Chain Genes," The EMBO Journal, vol. 12, No. 3, pp. 821-830, 1993.
Chen et al., "Immunoglobulin Heavy Chain Gene Replacement: A Mechanism of Receptor Editing" Immunity, vol. 3, pp. 747-755, Dec. 1995.
Cho, "Testicular and Epididymal ADAMs: Expression and Function During Fertilization," Nature, vol. 9, pp. 550-560, Oct. 2012.
Choi et al., "Characterization and Comparative Genomic Analysis of Intronless Adams With Testicular Gene Expression," Genomics 83, pp. 636-646, Aug. 2003.
Clark, Michael R., "IgG Effector Mechanisms," Chemical Immunology, vol. 65, pp. 88-110, 1997.
Clark et al., "Trends in Antibody Sequence Changes During the Somatic Hypermutation Process," The Journal of Immunology, vol. 177, pp. 333-340, 2006.
Clark et al., "A Future for Transgenic Livestock," Nature Reviews, Genetics, vol. 4, pp. 825-833, Oct. 2003.
Colbere Garapin et al., "A New Dominant Hybrid Selective Marker for Higher Eukaryotic Cells". Journal of Molecular Biology, vol. 150, No. 1, pp. 1-14, Jul. 25, 1981.
Collins, et al., "A Mouse for All Reasons," Cell, vol. 128, Issue 1, pp. 9-13, Jan. 2007.
Combriato, et al., "Regulation of Human Igλ Light Chain Gene Expression by NF-κB1," Journal of Immunology, Issue 168, vol. 3, pp. 1259-1266, Feb. 1, 2002.
Conrath, et al., "Camel Single-domain Antibodies as Modular Building Units in Bispecific and Bivalent Antibody Constructs," The Journal of Biological Chemistry, vol. 276, No. 10, pp. 7346-7350, Mar. 9, 2001.
Copeland et al., "Recombineering: A Powerful New Tool for Mouse Functional Genomic," Nature Reviews, Genetics, vol. 2, No. 10, pp. 769-779, Oct. 2001.
Corbett, et al., "Sequence of the Human Immunoglobulin Diversity (D) Segment Locus: A Systematic Analysis Provides No Evidence for the Use of DIR Segments, Inverted D Segments, "Minor" D Segments or D-D Recombination," Journal of Molecular Biology, vol. 270, No. 4, pp. 587-597, Jul. 25, 1997.
Corti et al., "A Neutralizing Antibody Selected from Plasma Cells That Binds to Group 1 and Group 2 Influenza A Hemagglutinins" Science, vol. 333, pp. 850-856, Aug. 12, 2011.
Cuesta et al., "Multivalent Antibodies: When Design Surpasses Evolution," Trends Biotechnology, vol. 28, No. 7, pp. 355-362, Jul. 2010.
Deng, et al., "Reexamination of Gene Targeting Frequency as a Function of the Extent of Homology between the Targeting Vector and the Target Locus," Molecular and Cellular Biology, vol. 12, No. 8, pp. 3365-3371, Aug. 1992.
De Saint Vincent et al., "Homologous Recombination in Mammalian Cells Mediates Formation of a Functional Gene From Two Overlapping Gene Fragments," Proceedings of National Academy of Sciences, USA, Genetics, vol. 80, No. 7, pp. 2002-2006, Apr. 1983.
DeChiara et al., "VelociMouse: Fully ES Cell-Derived FO-Generation Mice Obtained from the Injection of ES Cells into Eight-Cell-Stage Embryos," Methods in Molecular Biology, vol. 530, pp. 311-324, 2009.
DeChiara et al., "Producing Fully ES Cell-Derived Mice From Eight-Cell Stage Embryo Injections," Methods in Enzymology, vol. 476, Chapter 16, pp. 285-294, Jan. 2010.
Denome et al., "Patterns of Polyadenylation Site Selection in Gene Constructs Containing Multiple Polyadenylation Signals," Mol. Cell Biol., vol. 8, No. 11, pp. 4829-4839, Nov. 1988.
Diez-Roux et al., "A High-Resolution Anatomical Atlas of the Transcriptome in the Mouse Embryo," PloS Biology, vol. 9, Issue 1, pp. 1-13, Jan. 2011.
Ding, et al., "Generation of High-Affinity Fully Human Anti-Interleukin-8 Antibodies From Its cDNA by Two-Hybrid Screening and Affinity Maturation in Yeast," Protein Science, vol. 19, No. 10, pp. 1957-1966, Oct. 2010.
DiNoia et al., "Molecular Mechanism of Antibody Somatic Hypermutation," Annual Review of Biochemistry, vol. 76, No. 1, pp. 1-22, 2007.

(56) References Cited

OTHER PUBLICATIONS

Doetschman et al., "Establishment of Hamster Blastocyst-Derived Embryonic Stem (ES) Cells," Developmental Biology, vol. 127, No. 1, pp. 224-227, May 1988.

Doetschman, et al., "Targeted Mutation of the Hprt Gene in Mouse Embryonic Stem Cells," Proceedings of the National Academy of Sciences, USA, vol. 85, No. 22, pp. 8583-8587, Nov. 1988.

Doyle, et al., "The Construction of Transgenic and Gene Knockout/Knockin Mouse Models of Human Disease," Transgenic Research, vol. 21, No. 2, pp. 327-349, Apr. 2012.

Durbin, "A Map of Human Genome Variation From Population-Scale Sequencing," Nature, vol. 467, pp. 1061-1074, Oct. 28, 2012.

Durdik et al., "Isotype Switching by a Microinjected μ Immunoglobulin Heavy Chain Gene in Transgenic Mice," Proceedings of the National Academy of Sciences USA Immunol, vol. 86, pp. 2346-2350, Apr. 1989.

Edwards, et al., "Recombineering: A Powerful New Tools for Mouse Functional Genomic," Nature Reviews Genetics, vol. 2, No. 10, pp. 796-869, Oct. 2001.

Eisener-Dorman, et al., "Cautionary Insights on Knockout Mouse Studies: The Gene or Not the Gene?," Brain, Behavior, and Immunity, vol. 23, No. 3, pp. 318-324, Sep. 2009.

Ekiert et al., "A Highly Conserved Neutralizing Epitope on Group 2 Influenza A Viruses," Science, vol. 333, pp. 843-850, Aug. 12, 2011.

Evans, "Fertilin B and Other Adams As Integrin Ligands: Insights Into Cell Adhesion and Fertilization," BioEssays 23.7, pp. 628-639, Jul. 2001.

Featherstone et al., "The Mouse Immunoglobulin Heavy Chain V-D Intergenic Sequence Contains Insulators That May Regulate Ordered V(D)J Recombination," The Journal of Biological Chemistry, vol. 285, No. 13, pp. 9327-9338, Mar. 26, 2010.

Feeny, "Genetic and Epigenetic Control of V Gene Rearrangement Frequency," V(D)J Recombination Advances in Experimental Medicine and Biology, vol. 650, pp. 73-81, 2009.

Fell et al., "Homologous Recombination in Hybridoma Cells: Heavy Chain Chimeric Antibody Produced by Gene Targeting," Proceedings of the National Academy of Sciences USA Immunology, vol. 86, pp. 8507-8511, Nov. 1989.

Feschotte et al., "DNA Transposons and the Evolution of Eukaryotic Genomes," Annual Review Genetics, vol. 41, pp. 331-368, Dec. 2007.

Fleischer, et al., "Reactivity of Mouse T-Cell Hybridomas Expressing Human Vbeta Gene Segments With Staphylococcal and Streptococcal Superantigens," Infection and Immunity, vol. 64, No. 3, pp. 987-994, Mar. 1996.

Folger et al., "Patterns of Integration of DNA Microinjected into Cultured Mammalian Cells: Evidence for Homologous Recombination Between Injected Plasmid DNA Molecules," Molecular and Cellular Biology, vol. 2, No. 11, pp. 1372-1387, Nov. 1982.

Forconi et al., "The Normal IGHV1-69-derived B-cell Repertoire Contains Stereotypic Patterns Characteristic of Unmutated CLL," vol. 115, pp. 71-77, 2010.

Fukita et al., "Somatic Hypermutation in the Heavy Chain Locus Correlates with Transcription," Immunity, vol. 9, pp. 106-114, Jul. 1998.

Fujieda, et al., "Multiple Types of Chimeric Germ-Line Ig Heavy Chain Transcripts in Human B Cells: Evidence for Trans-Splicing of Human Ig RNA," The Journal of Immunology, vol. 157, No. 8, pp. 3450-3459, Oct. 15, 1996.

Gallo, et al., "The Human Immunoglobulin Loci Introduced Into Mice: V (D) and J Gene Segment Usage Similar to That of Adult Humans," European Journal of Immunology, vol. 30, pp. 534-540, Aug. 28, 2000.

Gavilondo, et al, "Antibody Engineering at the Millennium," BioTechniques, vol. 29, No. 1, pp. 128-145, Jul. 2000.

Gefter et al., "Expression of a VHC kappa chimaeric protein in mouse myeloma cells," Nature, pp. 364-367, May 24-30, 1984 (Abstract only).

Gerdes et al., "Physical Map of the Mouse λ Light Chain and Related Loci," Immunogenetics, vol. 54, pp. 62-65, 2002.

Gerstein, et al., "Isotype Switching of an Immunoglobulin Heavy Chain Transgene Occurs by DNA Recombination Between Different Chromosomes," Cell, vol. 63, No. 3, pp. 537-548, Nov. 1990.

Geurts et al., "Knockout Rats via Embryo Microinjection of Zinc-Finger Nucleases," Science, vol. 325, p. 433, Jul. 24, 2009.

Giallourakis, et al., "Elements Between the Igh Variable (V) and Diversity (D) Clusters Influence Antisense Transcription and Lineage-Specific V(D)J Recombination," Proceedings of the National Academy of Science USA, vol. 107, No. 51, pp. 22207-22212, Dec. 2010.

Giraldo, et al., Size Matters: Use of YACs, BACs and PACs in Transgenic Animals, Transgenic Research, vol. 10, No. 2, pp. 83-103, Apr. 2001.

Giusti, et al., "Hypermutation is Observed Only in Antibody H Chain V Region Transgenes That Have Recombined with Endogenous Immunoglobulin H DNA: Implications for the Location of cis-acting Elements Required for Somatic Mutation," The Journal of Experimental Medicine, vol. 177, pp. 797-809, Mar. 1, 1993.

Glanville, et al., "Naïve Antibody Gene-Segment Frequencies Are Heritable and Unaltered by Chronic Lymphocyte Ablation," Proceedings of the National Academy of Sciences, USA, vol. 108, No. 50, pp. 20066-20071, Dec. 13, 2011.

Gluzman, "SV40-Transformed Simian Cells Support the Replication of Early SV40 Mutants". Cell, vol. 23, pp. 175-182, Jan. 1981.

Goodhart, et al., "Rearrangement and Expression of Rabbit Immunoglobulin Kappa Light Chain Gene in Transgenic Mice," Proceedings of the National Academy of Sciences, USA, vol. 84, No. 12, pp. 4229-4233, Jun. 1987.

Gorman et al., "The Igκ 3' Enhancer Influences the Ratio of Igλ Versus Igλ B lymphocytes" Immunity, vol. 5, pp. 241-252, Sep. 1996.

Gorny et al., "Human Anti-V3 HIV-1 Monoclonal Antibodies Encoded by the VH5-51/VL Lambda Genes Define a Conserved Antigenic Structure," PloSone, vol. 6, Issue 12, pp. 1-10, Dec. 2011.

Goyenechea et al., "Cells Strongly Expressing Ig(Kappa) Transgenes Show Clonal Recruitment of Hypermutation: A Role for Both MAR and the Enhancers" The EMBO Journal, vol. 16, No. 13., pp. 3987-3994, 1997.

Green, et al, Antigen-Specific Human Monoclonal Antibodies From Mice Engineered With Human Ig Heavy and Light Chain YACs, Nature Genetics, vol. 7, No. 1, pp. 13-21, May 1994.

Green, et al, Regulation of B Cell Development by Variable Gene Complexity in Mice Reconstituted with Human Immunoglobulin Yeast Artificial Chromosomes, The Journal of Experimental Medicine, vol. 188, No. 3, pp. 483-495, Aug. 3, 1998.

Green, et al, "Antibody Engineering via Genetic Engineering of the Mouse: Xenomouse Strains are a Vehicle for the Facile Generation of Therapeutic Human Monoclonal Antibodies," Journal of Immunology Methods, vol. 231, No. 1-2, pp. 11-23, Dec. 10, 1999.

Gu et al., Independent Control of Immunoglobulin Switch Recombination at Individual Switch Regions Evidenced through Cre-loxP-Mediated Gene Targeting. Cell, vol. 73, pp. 1155-1164, Jun. 18, 1993.

Guerrero et al., "The Bleomycin Resistance Gene of Transposon Tn5 Is an Excellent Marker for Transformation of Corynebacteria," Applied Microbiology Biotechnology, vol. 36, No. 6, pp. 759-762, Mar. 1992.

Guntaka, "Transcription Termination and Polyadenylation in Retroviruses" Microbiological Reviews, vol. 57, No. 3, pp. 511-521, Sep. 1993.

Han et al., "Comprehensive Analysis of Reproductive ADAMs: Relationship of ADAM4 and ADAM6 with an ADAM Complex Required for Fertilization in Mice," Biology of Reproduction 80, pp. 1001-1008, Jan. 7, 2009.

Hasty et al., "Target Frequency and Integration Pattern for Insertion and Replacement Vectors in Embryonic Stem Cells," Molecular Cellular Biology, vol. 11, No. 9, pp. 4509-4517, Sep. 1991.

Hagiwara, Transgenic Expression of Vpreb-3 Under the Control of the Immunoglobulin Heavy Chain Enhancer and SV40 Promoter, Kobe Journal of Medical Sciences, vol. 42, No. 1, pp. 43-59 (English Abstract) Feb. 1996.

(56) References Cited

OTHER PUBLICATIONS

Hendricks, et al, "Organization of the Variable Region of the Immunoglobulin Heavy-Chain Gene Locus of the Rat," Immunogenetics, vol. 62, No. 7, pp. 479-486, Jul. 2010.
Houldsworth, et al, "Comparative Genomic Hybridization: an Overview," American Journal of Pathology, vol. 145, No. 6, pp. 1253-1260, Dec. 1994.
Houvila et al., "Shedding Light on ADAM Metalloproteinases," Trends in Biochemical Sciences, vol. 30, No. 7, pages, Jul. 2005.
Hudziak et al., "Establishment of Mammalian Cell Lines Containing Multiple Nonsense Mutations and Functional Suppressor tRNA Genes," Cell, vol. 31, pp. 137-146, Nov. 1982.
Huang, et al., "Structural Basis of Tyrosine Sulfation and VH-Gene Usage in Antibodies that Recognize the HIV Type 1 Coreceptor-Binding Site on gp120," PSNA, vol. 101, No. 9, pp. 2706-2711, Mar. 2, 2004.
Iglesias-Ussel, et al, "Forced Expression of AID Facilitates the Isolation of Class Switch Variants From Hybridoma Cells," Journal of Immunological Methods, Oct. 2006; 316(1-2), pp. 59-66.
Ivics et al., "The Expanding Universe of Transposon Technologies for Gene and Cell Engineering," Mobile DNA, pp. 1-25, 2010.
Ivics et al., "The Sleeping Beauty Transposable Element: Evolution, Regulation and Genetic Applications," Current. Issues in Molecular Biology, vol. 6, pp. 43-56, 2004.
Izsvak et al., "Sleeping Beauty Transposition: Biology and Applications for Molecular Therapy," Molecular Therapy, vol. 9, No. 2, pp. 147-156, Feb. 2, 2004.
Jacob et al., "Gene Targeting in the Rat: Advances and Opportunities," Trends in Genetics, vol. 26, No. 12, pp. 510-518, Dec. 2010.
Jakobovits, et al, "Production of Fully Human Antibodies by Transgenic Mice," Biotechnology, vol. 6, No. 5, pp. 561-566, Oct. 1995.
Jakobovits, "The Long-Awaited Magic Bullets: Therapeutic Human Monoclonal Antibodies from Transgenic Mice," Expert Opinion on Investigational Drugs, vol. 7, No. 4, pp. 607-614, Apr. 1998.
Jakobovits, et al., "From XenoMouse Technology to Panitumumab, The First Fully Human Antibody Product From Transgenic Mice," Nature Biotechnology, vol. 25, No. 10, pp. 1134-1143, Oct. 2007.
Janssens, et al., "Generation of heavy-chain-only antibodies in mice," Proceedings of the National Academy of Sciences, USA, Oct. 10, 2006, vol. 103, No. 41, pp. 15130-15135.
Jendreyko, et al., "Intradiabodies, Bispecific, Tetravalent Antibodies for the Simultaneous Functional Knockout of Two Cell Surface Receptors," The Journal of Biological Chemistry, vol. 278, pp. 47812-47819, Nov. 28, 2003.
Jessen, et al., "Molecular Analysis of Metastasis in a Polyomavirus Middle T Mouse Model: The Role of Osteopontin," Breast Cancer Research, vol. 6, No. 3, pp. R157-R169, Feb. 25, 2004.
Johnston, et al., "Complete Sequence Assembly and Characterization of the C57BL/6 Mouse Ig Heavy Chain V Region," The Journal of Immunology, vol. 176, No. 7, pp. 4221-4234, Apr. 1, 2006.
Jung, et al., "Mechanism and Control of V(D)J Recombination at the Immunoglobulin Heavy Chain Locus," Annual Review of Immunology, vol. 24, pp. 541-570, Apr. 2006.
Kaminski, et al., "Antibody Class Switching Differs Among SJL, C57BL/6 and 129 Mice," International Immunology, vol. 19, No. 4, pp. 545-556 , 2007.
Karu, et al, "Recombinant Antibody Technology," Institute for Laboratory Animal Research, vol. 37, No. 3, pp. 132-141, 1995.
Kellerman, et al, "Developing the Xenomouse Technology for Evaluating Immunogenicity ," AntibOZ 2 Conference, Australia, 2004.
Kenter, et al., "Three Dimensional Architecture of the IgH Locus Facilitates Class Switch Recombination," Annals of the New York Academy of Sciences, vol. 1267, No. 1, pp. 86-94, Sep. 1, 2012.
Kim et al., "CHO Cells in Biotechnology for Production of Recombinant Proteins: Current State and Further Potential" Appl. Microbiology Biotechnology, vol. 93, pp. 917-930, Dec. 9, 2011.
Kingzette et al., "Trans-Chromosomal Recombination Within the Ig Heavy Chain Switch Region in B Lymphocytes," Proceeding of the National Academy of Science USA, vol. 95, pp. 11840-11845, Sep. 1998.
Kitamura et al., "A B Cell-Deficient Mouse by Targeted Disruption of the Membrane Exon of the Immunoglobulin Chain Gene," Nature, vol. 350, pp. 423-426, Apr. 1991.
Kohrer et al., "Import of Amber and Ochre Suppressor tRNAs Into Mammalian Cells: A General Approach to Site-Specific Insertion of Amino Acid Analogues Into Proteins," Proceedings of the National Academy of Sciences USA, vol. 98, No. 25, pp. 214310-214315, Dec. 4, 2001.
Kostenuik, et al., Denosumab, A Fully Human Monoclonal Antibody to RANKL, Inhibits Bone Resorption and Increases BMD in Knock-In Mice That Express Chimeric (Murine/Human) RANKL, Journal of Bone and Mineral Research, vol. 24, No. 2, pp. 182-195, Nov. 2, 2009.
Kotzamaris et al., "Recombining Overlapping Bacs Into a Single Larger BAC," BMC Biotechnology, vol. 4, No. 1, pp. 1-10, Jan. 6, 2004.
Kouskoff, et al, "Cassette Vectors Directing Expression of T Cell Receptor Genes in Transgenic Mice," Journal of Immunology Methods, vol. 180, pp. 273-280, Mar. 27, 1995.
Krause, Epitope-Specific Human Influenza Antibody Repertoires Diversify by B Cell Intraclonal Sequence Divergence and Interclonal Convergence, The Journal of Immunology, pp. 3704-3711, Aug. 31, 2011.
Kruif et al., "Human Immunoglobulin Repertoires against Tetanus Toxoid Contain a Large and Diverse Fraction of High-Affinity Promiscuous $V_h$ Genes," Journal of Molecular Biology, vol. 387, Issue 3, pp. 548-558, Apr. 3, 2009.
Krutskikh et al., "Epididymal Protein Rnase10 Is Required for Post-Testicular Sperm Maturation and Male Fertility," The Federation of American Societies for Experimental Biological Journal, vol. 26, No. 10, pp. 4198-4209, Oct. 2012.
Kucherlapati et al., "Homologous Recombination Between Plasmids in Mammalian Cells Can Be Enhanced by Treatment of Input DNA," Proceedings of the National Academy of Sciences USA Genetics, vol. 81, pp. 3135-3157, May 1984.
Kuroiwa et al., "Sequential Targeting of the Genes Encoding Immunoglobulin and Prion Protein in Cattle," Nature Genetics, vol. 36, No. 7, pp. 775-780, Jul. 2004.
Laventie, et al., "Heavy Chain-Only Antibodies and Tetravalent Bispecific Antibody Neutralizing *Staphylococcus aureus* Leukotoxins," Proceedings of the National Academy of Sciences, USA, vol. 108, No. 39, pp. 16404-16409, Sep. 27, 2011.
Lee et al, "Human C5ar Knock-In Mice Facilitate the Production and Assessment of Anti-Inflammatory Monoclonal Antibodies," Nature Biotechnology, vol. 24, No. 10, pp. 1279-1284, Oct. 2006.
Lee, et al., "Complete Humanization of the Mouse Immunoglobulin Loci Enables Efficient Therapeutic Antibody Discovery," Nature Biotechnology, vol. 32, No. 4, pp. 356-363, Mar. 16, 2014.
Lefranc, Marie-Paule, "Nomenclature of the Human Immunoglobulin Heavy (IGH) Genes," Experimental and Clinical Immunogenetics, vol. 18, pp. 100-1116, Aug. 31, 2000.
Lefranc, Marie-Paule, "Nomenclature of the Human Immunoglobulin Lambda (IGL) Genes," Experimental and Clinical Immunogenetics, Mar. 17, 2001.
Li et al., "Transgenic Mice With a Diverse Human T Cell Antigen Receptor Repertoire," Nature Medicine, vol. 16, No. 9, pp. 1029-1035, Sep. 2010.
Li et al., "The Minimum Internal and External Sequence Requirements for Transposition of the Eukaryotic Transformation Vector Piggyback," Mol. Genet. Genomics, vol. 266, pp. 190-198, 2001.
Li et al., "Crafting Rat Genomes With Zinc Fingers," Nature Biotechnology, vol. 29, No. 1, pp. 39-41, Jan. 2011.
Li et al., "Germline Competent Embryonic Stem Cells Derived from Rat Blastocysts," Cell, vol. 135, pp. 1299-1310, Dec. 26, 2008.
Liao et al., "Generation of Induced Pluripotent Stem Cell Lines from Adult Rat Cells," Cell Stem Cell Brief Report, vol. 4, pp. 11-15, Jan. 9, 2009.

(56) References Cited

OTHER PUBLICATIONS

Luciw et al., "Location and Function of Retroviral and SV40 Sequences that Enhance Biochemical Transformation after Microinjection of DNA," Cell., vol. 33, pp. 705-176, Jul. 1983.
Luo et al., "Chromosomal Transposition of a Tc1/Mariner-Like Element in Mouse Embryonic Stem Cells," Proceedings of the National Academy of Science USA, Genetics, vol. 95, pp. 10769-10773, Sep. 1998.
Liu, et al., "Potent and Broad Anti-HIV-1 Activity Exhibited by a Glycosyl-Phosphatidylinositol-Anchored Peptide Derived from the CDR H3 of Broadly Neutralizing Antibody PG16," Journal of Virology, vol. 85, No. 17, pp. 8467-8476, Sep. 2011.
Lonberg, "Human Antibodies From Transgenic Animals," Nature Biotechnology, vol. 23, No. 9, pp. 1117-1125, Sep. 2005.
Loveslati, et al., "A Study of Gm Allotypes and Immunoglobulin Heavy Gamma IGHG Genes in Berbers, Arabs and Sub-Saharan Africans From Jerba Island, Tunisia'" Blackwell Science Ltd., European Journal of Immunogenetics, vol. 28, No. 5, pp. 531-538, Oct. 2001.
Luby, et al., "The Switch Region Tandem Repeats Are Important, But Not Required, for Antibody Class Switch Recombination," The Journal of Experimental Medicine, vol. 193, No. 2, pp. 159-168, Jan. 15, 2001.
Ma, et al, "Human Antibody Expression in Transgenic Rats: Comparison of Chimeric IgH Loci With Human VH, D and JH but Bearing Different Rat C-Gene Regions," Journal of Immunological Methods, vol. 400-401, pp. 78-86, Dec. 31, 2013.
Mack et al., "A Small Bispecific Antibody Construct Expressed As a Functional Single-Chain Molecule With High Tumor Cell Cytotoxicity," Proceeding of the National Academy Science USA, Immunology, vol. 92, pp. 7021-7025, Jul. 1995.
Makris et al., "Mutational Analysis of Insertion Sequence 50 (IS50) and Transposon 5 (Tn5) ends," Proceeding of the National Academy of Science USA, Genetics, vol. 85, pp. 2224-2228, Apr. 1988.
Mallender et al., "Construction, Expression, and Activity of a Bivalent Bispecific Single-chain Antibody," The Journal of Biological Chemistry, vol. 269, No. 1, pp. 199-206, 1994.
Manis, et al., "Mechanism and Control of Class-Switch Recombination," Trends in Immunology, vol. 23, Issue 1, pp. 31-39, Jan. 2002.
Marcello et al., "Lack of Tyrosylprotein Sulfotransferase-2 Activity Results in Altered Sperm-Egg Interactions and Loss of ADAM3 and ADAM6 in Epididymal Sperm," The Journal of Biological Chemistry, vol. 286, No. 15, pp. 13060-13070, Apr. 15, 2011.
Macdonald, et al., "Precise and In Situ Genetic Humanization of 6Mb of Mouse Immunoglobulin Genes," Proceedings of the National Academy of Sciences, USA, vol. 111, No. 14, pp. 5147-5152, Apr. 8, 2014.
Martensson et al., "Role of the Surrogate Light Chain and the Pre-B-Cell Receptor in Mouse B-Cell Development," Immunology, vol. 101, pp. 435-441, 2000.
Maitta, et al., "Immunogenicity and Efficacy of *Cryptococcus neoformans* Capsular Polysaccharide Glucuronoxylomannan Peptide Mimotope-Protein Conjugates in Human Immunoglobulin Transgenic Mice," Infection and Immunity, vol. 72, No. 1, pp. 196-208, Jan. 2004.
Mattila, P.S., et al., "Extensive Allelic Sequence Variation in the J Region of the Human Immunoglobulin Heavy Chain Gene Locus," European Journal of Immunology, vol. 25, No. 9, pp. 2578-2582, Sep. 1995.
Maul et al., "AID and Somatic Hypermutation," Advances in Immunology, vol. 105, pp. 159-191, 2010.
McCreath et al., "Production of Gene-Targeted Sheep by Nuclear Transfer From Cultured Somatic Cells," Nature, vol. 405, pp. 1066-1070, Jul. 29, 2000.
McMurry, et al, "Enhancer Control of Local Accessibility of V(D)J Recombinase," Molecular and Cellular Biology, vol. 17, No. 8, pp. 45533-4561, Aug. 1997.
Mejia et al., "The Assembly of Large BACs by in Vivo Recombination," Genomics, vol. 70, pp. 165-170, 2000.

Mendez, et al., "Functional Transplant of Megabase Human Immunoglobulin Loci Recapitulates Human Antibody Response in Mice," Nature Genetics, vol. 15, pp. 146-156, Feb. 1997.
Milner, et al, "Polymorphism and utilization of Human $V_h$ Genes," Annals of the New York Academy of Sciences, vol. 764, pp. 50-61, Sep. 1995.
Mir, "Sequencing Genomes: From Individuals to Populations," Briefings in Functional Genomics Proteomics, vol. 8, No. 5, pp. 367-378, 2009.
Monaco, et al., YACs, Bas, OPACs and MACs: Artificial Chromosomes As Research Tools, Tends in Biotechnology, vol. 12, No. 7, pp. 280-286, Jul. 1994.
Moreau et al., "The SV40 72 Base Repair Repeat Has a Striking Effect on Gene Expression Both in SV40 and Other Chimeric Recombinants," Nucleic Acids Research, vol. 9, No. 22, pp. 6047-6068, 1981.
Moran, Nuala, "Mouse Platforms Jostle for Slice of Humanized Antibody Market," Nature Biotechnology, vol. 31, pp. 267-268, 2013.
Moreno et al., "The Emerging Role of Matrix Metalloproteases of the ADAM Family in Male Germ Cell Apoptosis," Spermatogenesis, vol. 1, No. 3, pp. 195-208, Jul./Aug./Sep. 2011.
Mouellic et al., "Pattern of Transcription of the Homeo Gene Hox-3.1 in the Mouse Embryo," Genes and Development., vol. 2, No. 1, pp. 125-135, Jan. 1988.
Mortuza et al., "Immunoglobulin Heavy-Chain Gene Rearrangement in Adult Acute Lymphoblastic Leukemia Reveals Preferential Usage of JH-Proximal Variable Gene Segments," Blood, vol. 97, No. 9, pp. 2716-2726, May 2001.
Müller, Ulrike, "Ten Years of Gene Targeting: Targeted Mouse Mutants, From Vector Design to Phenotype Analysis," Mechanisms of Development, vol. 82, Issues 1-2, pp. 3-21, Apr. 1999.
Murphy, "VelocImmune: Immunoglobulin Variable Region Humanized Mice," Recombinant Antibodies for Immunotherapy. $1^{st}$ ed. Cambridge: Cambridge University Press, pp. 100-108, 2009.
Murphy, et al., "Mice With Megabase Humanization of Their Immunoglobulin Genes Generate Antibodies as Efficiently as Normal Mice," Proceedings of the National Academy of Sciences, vol. 111, No. 14, pp. 5153-5158, Apr. 8, 2014.
Muyrers, et al, "Rapid Modification of Bacterial Artificial Chromosomes by ET-Recombination," Nucleic Acids Research, vol. 27, No. 6, pp. 1555-1557, Feb. 2, 1999.
Nadel, et al., "Sequence of the Spacer in the Recombination Signal Sequence Affects V(D)J Rearrangement Frequency and Correlates with Nonrandom Vκ Usage in Vivo," Journal of Experimental Medicine, vol. 187, No. 9, pp. 1495-1503, May 4, 1998.
Nagle, "Regeneron Helps Make Sanofi Velocimmune to Its 'Weak' Pipeline," Outsourcing-Pharmac.com, 2 pages, Dec. 3, 2007.
Nandi et al., "Regulated expression of Genes Inserted at the Human Chromosomal B-Globin Locus by Homologous Recombination," Proceedings of the National Academy of Sciences, USA, Cell Biology, vol. 85, pp. 3845-3849, Jun. 1998.
Narayanan, et al., "Efficient and Precise Engineering of a 200 Kb β-Globin Human/Bacterial Artificial Chromosome in *E. coli* Dh10b Using an Inducible Homologous Recombination System," Gene Therapy, vol. 6, No. 3, pp. 442-447, Mar. 1999.
Narayanan et al., "Bacterial Artificial Chromosome Mutagenesis Using Recombineering" Journal of Biomedicine and Biotechnology, vol. 2011, Article ID 971296, 10 pages, Dec. 9, 2010.
Nelson et al., "Development trends for human monoclonal antibody therapeutics," Nature Reviews, Drug Discovery, vol. 9, pp. 767-774, Oct. 2010.
Neuberger et al., "Somatic hypermutation," Current Opinion in Immunology, vol. 7, pp. 248-254, 1995.
Neuberger, et al, "Isotype Exclusion and Transgene Down-Regulation in Immunoglobulin-Lambda Transgenic Mice," Nature, vol. 338, No. 5213, pp. 350-352, Mar. 23, 1989.
Nicholson, et al., "Antibody Repertoires of Four- and Five-Feature Translocus Mice Carrying Human Immunoglobulin Heavy Chain and κ and λ Light Chain Yeast Artificial Chromosomes," The Journal of Immunology, vol. 163, No. 12, pp. 6898-6906, Dec. 15, 1999.

(56) References Cited

OTHER PUBLICATIONS

Niemann et al. "Transgenic Farm Animals: Present and Future," Revue Scientifique et Technique (International Office of Epizootics)., vol. 24, No. 1, pp. 285-298, Apr. 2005.
Oancea et al., "Expression of the (Recombinant) Endogenous Immunoglobulin Heavy-Chain Locus requires the Intronic Matrix Attachment Regions," Molecular and Cellular Biology, vol. 17, No. 5, pp. 2658-2668, May 1997.
Oberdoerffer et al., "Unidirectional Cre-mediated Genetic Inversion in Mice Using the Mutant Loxp Pair Lox66/Lox71," Nucleic Acids Research, vol. 31, No. 22, pp. 1-7, 2003.
Ohlin, et al., "The Human Antibody Repertoire to Infectious Agents: Implications for Disease Pathogenesis," Molecular Immunology, vol. 40, Issue 1, pp. 1-11, Sep. 2003.
Ohm-Laursen, et al., "Identification of Two New Alleles, IGHV3-23*04 and IGHJ6*04, and the Complete Sequence of the IGHV3-H Pseudogene in the Human Immunoglobulin Locus and Their Prevalences in Danish Caucasians," Immunogenetics, vol. 57, No. 9, pp. 621-627, Oct. 2005.
Osborn et al., "High-Affinity IgG Antibodies Develop Naturally in Ig-Knockout Rats Carrying Germline Human IgH/Ig k/Igλ Loci Bearing the Rat Ch Region," The Journal of Immunology, pp. 1481-1490, Feb. 15, 2013 (E Pub Jan. 9, 2013).
Osoegawa et al., "Bacterial Artificial Chromosome Libraries for Mouse Sequencing and Functional Analysis," Genome Research, vol. 10, No. 1, pp. 116-128, Jan. 2000.
Pavlicek et al., "Ancient Transposable Elements, Processed Pseudogenes, and Endogenous Retroviruses," Genomic Disorders, Chapter 4, pp. 57-72, 2006.
Pelham et al., "Expression of a Drosophila Heat Shock Protein in Mammalian Cells: Transient Association with Nucleoli after Heat Shock," Philosophical Transactions of the Royal Society, pp. 301-307, 1984.
Perlot et al., "Antisense Transcripts From Immunoglobulin Heavy-Chain Locus V(D)J and Switch Regions," Proceedings of the National Academy of Sciences, vol. 105, No. 10, pp. 3843-3848, Mar. 11, 2008.
Perlot et al., "Cis-Regulatory Elements and Epigenetic Changes Control Genomic Rearrangements of the IgH Locus," Advances in Immunology, vol. 99, pp. 1-32, 2008.
Pettitt, et al., "Agouti C57BL/6N Embryonic Stem Cells for Mouse Genetic Resources," Nature Methods, vol. 6, No. 7, pp. 493-495 (Jul. 2009).
Plasterk et al., "Resident aliens: The Tc1/Mariner Superfamily of Transposable Elements," YIG, vol. 15, No. 8, pp. 326-333, Aug. 1999.
Ponsel, et al., "High Affinity, Developability and Functional Size: The Holy Grail of Combinatorial Antibody Library Generation," Molecules, vol. 16, No. 5, pp. 3675-3700, 2011.
Popov et al., "A Human Immunoglobulin λ Locus Is Similarly Well Expressed in Mice and Humans," Journal of Experimental Medicine, vol. 189, No. 10, pp. 1611-1619, May 17, 1999.
Pramanik, et al., Segmental Duplication as One of the Driving Forces Underlying the Diversity of the Human Immunoglobulin Heavy Chain Variable Gene Region, BMC Genomics, vol. 12, No. 78, 2011.
Primakoff et al., "Penetration, Adhesion, and Fusion in Mammalian Sperm-Egg Interaction," Science, vol. 296, pp. 2183-2185, Jun. 21, 2002.
Primakoff et al., "The ADAM Gene Family: Surface Proteins With Adhesion and Protease Activity," Trends in Genetics, vol. 16, No. 2, pp. 83-87, Feb. 2000.
Puente et al., "Comparative Genomic Analysis of Human and Chimpanzee Proteases," Genomics, vol. 86, pp. 638-647, 2005.
Prosser, et al., "Mosaic Complementation Demonstrates a Regulatory Role for Myosin Viia in Actin Dynamics of Stereocilia," Molecular and Cellular Biology, Mar. 2008, vol. 28, No. 5, pp. 1702-1712.
Prosser, et al., "A Resource of Vectors and ES Cells for Targeted Deletion of Micrornas in Mice," Nature Biotechnology, vol. 29, No. 9, pp. 840-845, Sep. 2011.
Pruzina, et al., "Human Monoclonal Antibodies to HIV-1 Gp140 From Mice Bearing YAC-Based Human Immunoglobulin Transloci," Protein Engineering, Design & Selection, vol. 24, No. 10, pp. 791-799, Aug. 2011.
Qu et al., "Gene Targeting of ErbB3 Using a Cre-Mediated Unidirectional DNA Inversion Strategy," Technology Report, Genesis, vol. 44, pp. 477-486, 2006.
Ray, et al., "Ectopic Expression of a C-Kitw42 Minigene in Transgenic Mice: Recapitulation of W Phenotypes and Evidence for C-Kit Function in Melanoblast Progenitors," Genes & Development, vol. 5, pp. 2265-2273, 1991.
Raynard et al., "Cis-acting Regulatory Sequences Promote High-Frequency Gene Conversion Between Repeated Sequences in Mammalian Cells," Nucleic Acids Research, vol. 32, No. 19, pp. 5916-5927, Nov. 4, 2004.
Reddy et al., "Monoclonal Antibodies Isolated Without Screening by Analyzing the Variable-Gene Repertoire of Plasma Cells," Nature Biotechnology, vol. 28, No. 9, pp. 965-971, Sep. 2010.
Regeneron, "Big Pharma Vies for Mice," Nature Biotechnology, Jun. 2007, vol. 25, No. 6, p. 613.
Ren, et al, "Targeted Insertion Results in a Rhombomere 2-Specific Hoxa2 Knockdown and Ectopic Activation of Hoxa1 Expression," Developmental Dynamics, vol. 225, No. 3, pp. 305-315, Nov. 2002.
Retter, "Sequence and Characterization of the Ig Heavy Chain Constant and Partial Variable Region of the Mouse Strain 129S1," The Journal of Immunology, vol. 179, pp. 2419-2427, 2007.
Rivera, et al., "Genetic Background and the Dilemma of Translating Mouse Studies to Humans," Immunity, vol. 28, No. 1, pp. 1-4, Jan. 28, 2008.
Rodriguez, et al., "High-efficiency Deleter Mice Show That Flpe Is an Alternative to Cre-Loxp," Nature Genetics, vol. 25, pp. 139-140, Jun. 2000.
Rogozin et al., "Cutting Edge: DGYW/WRCH Is a Better Predictor of Mutability at G:c Bases in Ig Hypermutation Than the Widely Accepted RGYW/WRCY Motif and Probably Reflects a Two-Step Activation-Induced Cytidine Deaminase-Triggered Process," Journal of Immunology, vol. 172, pp. 3382-3384, 2004.
Sakai et al., "Recombination and Transcription of the Endogenous Ig Heavy Chain Locus Is Effected by the Ig Heavy Chain Intronic Enhancer Core Region in the Absence of the Matrix Attachment Regions," Proceedings of the National Academy of Sciences., vol. 96, pp. 1526-1531, Feb. 1999.
Sarkar et al., "Molecular Evolutionary Analysis of the Widespread *piggyBac* Transposon Family and Related "Domesticated" Sequences," Molecular Genetics and Genomics, vol. 270, No. 2, pp. 173-180, Nov. 2003.
Sasso et al., "Expression of the Immunoglobulin Vh Gene 51p1 Is Proportional to Its Germline Gene Copy Number," Journal of Clinical Investigation., vol. 97, No. 9, pp. 2074-2080, May 1996.
Sasso, et al., "Ethnic differences in Polymorphism of an Immunoglobulin $V_h3$ gene," Journal of Clinical Investigation, vol. 96, No. 3, pp. 1591-1600, Sep. 1995.
Sauer, "Functional Expression of the cre-lox Site-Specific Recombination System in the Yeast *Saccharomyces cerevisiae*," Molecular and Cellular Biology, vol. 7, No. 6, pp. 2087-2096, Jun. 1987.
Sauer et al., "Cre-stimulated Recombination at Loxp-Containing DNA Sequences Placed Into the Mammalian Genome," Nucleic Acids Research, vol. 17, No. 1, pp. 147-161, 1989.
Sauer et al., "Site-specific DNA Recombination in Mammalian Cells by the Cre Recombinase of Bacteriophage P1," Proc. Natl. Acad. Sci. USA, Genetics, vol. 85, pp. 5166-5170, 1988.
Scapini, et al., "Myeloid Cells, BAFF, and IFN-γ Establish an Inflammatory Loop That Exacerbates Autoimmunity in Lyn-Deficient Mice," The Journal of Experimental Medicine, vol. 207, No. 8, pp. 1757-1773, Jul. 12, 2010.
Schnutgen et al., "A Directional Strategy for Monitoring Cre-Mediated Recombination at the Cellular Level in the Mouse", Nature Biotechnology, vol. 21, pp. 562-565, May 2003.

(56) References Cited

OTHER PUBLICATIONS

Schlake et al., "Use of Mutated FLP Recognition Target (FRT) Sites for the Exchange of Expression Cassettes at Defined Chromosomal Loci," Biochemistry, vol. 33, pp. 12746-12751, 1994.
Schrock et al., "Comparative Genomic Hybridization (CGH)—Detection of Unbalanced Genetic Aberrations Using Conventional Micro-Array Techniques," Molecular Cytogenetics, Unit 8.12.1, Supplement 18, 30 pages, 2001.
Schroeder, et al., "Preferential Utilization of Conserved Immunoglobulin Heavy Chain Variable Gene Segments During Human Fetal Life," Proc. Natl. Acad. Science USA, vol. 87, pp. 6146-6150, Aug. 1990.
Schweinfest et al., "A Heat-Shock-Inducible Eukaryotic Expression Vector," Gene. 71, pp. 207-210, 1988.
Scott, "Mice With a Human Touch," Nature Biotechnology, vol. 25, pp. 1075-1077, Dec. 2007.
Seals, et al., "The Adams Family of Metalloproteases: Multidomain Proteins With Multiple Functions," Genes & Development, vol. 17, No. 1, pp. 7-30, Jan. 2003.
Seed et al., "Purification of Genomic Sequences From Bacteriophage Libraries by Recombination and Selection in Vivo," Nucleic Acids Research, vol. 11, No. 8, pp. 2427-2445, 1983.
Seidl, et al, "An Expressed Neo® Cassette Provides Required Functions of the 1gamma2b Exon for Class Switching," International Immunology, vol. 10, No. 11, pp. 1683-1692, Nov. 1998.
Seidl, et al., "Position-Dependent Inhibition of Class-Switch Recombination by PGK-neo$^r$ Cassettes Inserted Into the Immunoglobulin Heavy Chain Constant Region Locus," Proceedings of the National Academy of Sciences,USA, vol. 96, No. 6, pp. 3000-3005, Mar. 16, 1999.
Sen, et al., "Multiple Nuclear Factors Interact With the Immunoglobulin Enhancer Sequences," Cell, vol. 46, pp. 705-716, Aug. 29, 1986.
Seong, et al., "To knockout in 129 or in C57BL/6: that is the question," Trends in Genetics, vol. 20, No. 2, pp. 59-62, Feb. 2004.
Serwe et al., "V(D)J Recombination in B Cells Is Impaired But Not Blocked by Targeted Deletion of the Immunoglobulin Heavy Chain Intron Enhancer," The EMBO Journal, vol. 12, No. 6, pp. 2321-2327, 1993.
Shaul, et al, "Homologous Recombination Between a Defective Virus and a Chromosomal Sequence in Mammalian Cells," Proceedings of the National Academy of Sciences,USA, vol. 89, pp. 3781-3784, Jun. 1985.
Shi, et al., "Comparative Analysis of Human and Mouse Immunoglobulin Variable Heavy Regions from IMGT/LIGM-DB with IMGT/HighV-QUEST," Theoretical Biology and Medical Modelling, vol. 11, pp. 1-11, Nov. 2014.
Shimizu et al., "Immunoglobulin double-isotype expression by trans-mRNA in a human immunoglobulin transgenic mouse," Proceedings of the National Academy of Sciences, USA, Immunology, vol. 86, pp. 8020-8023, Oct. 1989.
Shultz, et al., "Humanized mice in translational biomedical research," The Journal of Immunology, Feb. 2007, vol. 7, No. 2, pp. 118-130.
Sirac, et al., "Role of the Monoclonal κ Chain V Domain and Reversibility of Renal Damage in a Transgenic Model of Acquired Fanconi Syndrome," Blood, Jul. 15, 2006, vol. 108, No. 2, pp. 536-543.
Skarnes, et al., "A Conditional Knockout Resource for the Genome-Wide Study of Mouse Gene Function," Nature, vol. 474, pp. 337-342, Jun. 16, 2011.
Simpson, et al., "Genetic Variation Among 129 Substrains and Its Importance for Targeted Mutagenesis in Mice," Nature Genetics, vol. 16, pp. 19-27, May 16, 1997.
Skoultchi et al., "Expression of Genes Inserted at the Human B-Globin Locus by Homologous Recombination," Developmental Control of Globin Gene Expression, pp. 581-594, 1987.
Smithies, "Direct Alteration of a Gene in the Human Genome," J. Inher. Metab., Dis. 9, Suppl. 1, pp. 92-97, 1986.
Smithies et al., "Insertion of DNA Sequences Into the Human Chromosomal B-Globin Locus by Homologous Recombination," Nature, vol. 317, No. 19, pp. 230-234, Sep. 1985.
Sohn et al., "Somatic Hypermutation of an Immunoglobulin μ Heavy Chain Transgene," Journal of Experimental Medicine, vol. 177, pp. 493-504, Feb. 1993.
Song et al., "Accurate Modification of a Chromosomal Plasmid by Homologous Recombination in Human Cells," Proceedings of the National Academy of Science, USA, Genetics, vol. 84, pp. 6820-6824, Oct. 1987.
Sonoda et al., "B Cell Development under the Condition of Allelic Inclusion," Immunology, vol. 6, pp. 225-233, Mar. 1997.
Soukharev, et al., "Segmental Genomic Replacement in Embryonic Stem Cells by Double lox Targeting," Nucleic Acids Research, vol. 27, No. 18, pp. e21-i to e21-viii, Jun. 1, 1999.
Spanopoulou, et al., "Functional Immunoglobulin Transgenes Guide Ordered B-Cell Differentiation in Rag-1-Deficient Mice," Genes & Development, vol. 8, No. 9, pp. 1030-1042, May 1, 1994.
Stavnezer, et al., "Mechanism and Regulation of Class Switch Recombination," Annual Review of Immunology, vol. 26, pp. 261-292, Apr. 2008.
Storb et al., "Physical Linkage of Mouse Genes by Pulsed-Field Gel Electrophoresis Suggests that the Rearrangement Process Favors Proximate Target Sequences," Molecular and Cellular Biology, vol. 9, No. 2, pp. 711-718, Feb. 1989.
Stevens et al., "Human Antibody Discovery, VelocImmune—A novel platform," Pharma Focus Asia, Clinical Trials Issue 8, pp. 1-5, 2008.
Suárez, et al., "Rearrangement of Only One Human IGHV Gene is Sufficient to Generate a Wide Repertoire of Antigen Specific Antibody Responses in Transgenic Mice," Molecular Immunology, vol. 43, No. 11, pp. 1827-2835, Dec. 2006.
Taki et al., "Targeted Insertion of a Variable Region Gene into the Immunoglobulin Heavy Chain Locus," Science, vol. 262, pp. 1268-1271, Nov. 19, 1993.
Talbot et al., "Cell Adhesion and Fertilization: Steps in Oocyte Transport, Sperm-Zona Pellucida Interactions, and Sperm-Egg Fusion," Biology of Reproduction 68, pp. 1-9, 2003.
Tan, et al., "A Human-Mouse Chimeric Immunoglobulin Gene With a Human Variable Region Is Expressed in Mouse Myeloma Cells," The Journal of Immunology vol. 135, No. 5, pp. 3564-3567, Nov. 1, 1985.
Taylor, et al., "Human Immunoglobulin Transgenes Undergo Rearrangement, Somatic Mutation and Class Switching in Mice That Lack Endogenous IgM," International Immunology, vol. 6, No. 4, pp. 579-591, Apr. 1994.
Te Riele, et al., "Highly Efficient Gene Targeting in Embryonic Stem Cells Through Homologous Recombination With Isogenic DNA Constructs," Proceedings of the National Academy of Sciences, USA, vol. 89, pp. 5128-5132, Jun. 1992.
Thomas et al., "High Frequency Targeting of Genes to Specific Sites in the Mammalian Genome," Cell, vol. 44, pp. 419-428, Feb. 14, 1986.
Thomas et al., "Introduction of Homologous DNA Sequences Into Mammalian Cells Induces Mutations in the Cognate Gene" Nature, vol. 324, Nov. 1986.
Thomas et al., "Site-Directed Mutagenesis by Gene Targeting in Mouse Embryo-derived stem cells," Cell, vol. 51, pp. 503-512, Nov. 6, 1987.
Thykhaer, et al., "Gene Targeting Approaches Using Positive-Negative Selection and Large Flanking Regions," Plant molecular Biology, vol. 35, No. 4, pp. 523-530, Nov. 1997.
Tomizuka, et al., "Double Trans-Chromosomic Mice: Maintenance of Two Individual Human Chromosome Fragments Containing Ig Heavy and K Loci and Expression of Fully Human Antibodies," Proceedings of the National Academy of Sciences, USA, Jan. 18, 2000, vol. 97, No. 2, pp. 722-727.
Tucker, et al., "Mouse IgA Heavy Chain Gene Sequence: Implications for Evolution of Immunoglobulin Hinge Axons," Proceedings of the National Academy of Sciences, USA, vol. 78, No. 12, pp. 7684-7688, Dec. 2008.
Torres et al., "Laboratory Protocols for Conditional Gene Targeting," Institute for Genetics, University of Cologne, pp. 37-40, 1997.

(56) References Cited

OTHER PUBLICATIONS

Ungrin et al., "Strict Control of Telomerase Activation Using Cre-Mediated Inversion," BMC Biotechnology, vol. 6, pp. 1-9, 2006.
Valenzuela, et al., "High-Throughput Engineering of the Mouse Genome Coupled With High-Resolution Expression Analysis," Nature Biotechnology vol. 21, No. 6, p. 652-659 and vol. 21, No. 7, p. 822, (2003).
Van Spriel, et al., "Immunotherapeutic Perspective for Bispecific Antibodies," Immunology Today, vol. 21, No. 8, pp. 391-397, Aug. 1, 2000.
Vassilieva et al., "Establishment of SSEA-1- and Oct-4 Expressing Rat Embryonic Stem-Like Cell Lines and Effects of Cytokines of the IL-6 Family on Clonal Growth," Experimental Cell Research, vol. 258, pp. 361-373, Aug. 2000.
Vasicek, et al., Structure and Expression of the Human Immunoglobulin λ Genes, Journal of Experimental Medicine, vol. 172, pp. 609-620, Aug. 1990.
Venken et al., "P[acman]: A BAC Transgenic Platform for Targeted Insertion of Large DNA Fragments in *D. melanogaster*," Science, vol. 314, pp. 1747-1751, Dec. 15, 2006.
Vollmer, et al., "Antigen Contacts by Ni-Reactive TCR: Typical αβ Chain Cooperation Versus a Chain-Dominated Specificity," International Immunity, vol. 12, No. 12, pp. 1723-1731, May 31, 2000.
Vora et al., "Altering the Antibody Repertoire via Transgene Homologous Recombination: Evidence for Global and Clone-autonomous Regulation of Antigen-driven B Cell Differentiation," Journal of Experimental Medicine, vol. 181, pp. 271-281, Jan. 1995.
Wallace et al., "Manipulating the Mouse Genome to Engineer Precise Functional Syntenic Replacements with Human Sequence," Cell, vol. 18, pp. 197-209, Jan. 12, 2007.
Wang et al., "AID Upmutants Isolated Using a High-Throughput Screen Highlight the Immunity/Cancer Balance Limiting DNA Deaminase Activity," Nature Structural & Molecular Biology, vol. 16, No. 7, Jul. 2009.
Wang et al., "Altering the Spectrum of Immunoglobulin V Gene Somatic Hypermutation by Modifying the Active Site of AID," Journal of Experimental Medicine., vol. 207, No. 1, pp. 141-153, 2010.
Wang et al., "Catching a Moving Target," Science, Biochemistry, vol. 333, pp. 834-835, Aug. 21, 2011.
Wang, et al., "Chromosomal Transposition of piggyBac in Mouse Embryonic Stem Cells," Proceedings of the National Academy of Sciences, USA, vol. 105, No. 27, pp. 9290-9295, 2008.
Wang, et al., "Many Human Immunoglobulin Heavy-Chain IGHV Gene Polymorphisms Have Been Reported in Error," Immunology and Cell Biology, vol. 86, No. 2, pp. 111-115, Feb. 2008.
Waterhouse, et al., "Combinatorial Infection and In Vivo Recombination: A Strategy for Making Large Phage Antibody Repertories," Nucleic Acids Research, vol. 21, No. 9, pp. 2265-2266. May 11, 1993.
White, et al, "Genome-Wide Generation and Systematic Phenotyping of Knockout Mice Revels New Roles for Many Genes," Cell, vol. 154, Issue 2: pp. 452-464, Jul. 18, 2013.
Wilke, et al., "Diagnosis of Haploidy and Triploidy Based on Measurement of Gene Copy Number By Real-Time PCR," Human Mutation vol. 16, Issue 5, pp. 431-436, Nov. 2000.
Wilkie et al., "Analysis of the Integrant in MyK-103 Transgenic Mice in which Males Fail to Transmit the Integrant," Molecular and Cellular Biology, pp. 1646-1655, May 1987.
Williams et al., "Unequal VH Gene Rearrangement Frequency Within the Large Vh7183 Gene Family is not Due to Recombination Signal Sequence Variation, and Mapping of the Genes Shows a Bias of Rearrangement Base on Chromosomal Location," The Journal of Immunology, pp. 257-263, 2001.
Wuerffel, et al., "S-S Synapsis during Class Switch Recombination Is Promoted by Distantly Located Transcriptional Elements and Activation-Induced Deaminase," Immunity, vol. 27, Issue 5, pp. 711-722, Nov. 26, 2007.

Xu, et al., "Deletion of the Igκ Light Chain Intronic Enhancer/Matrix Attachment Region Impairs but Does Not Abolish VκJκ Rearrangement," Immunity, vol. 4, pp. 377-385, Apr. 1, 1996.
Xu, et al., "Combinatorial Surrobody Libraries," Proceedings of the National Academy of Sciences, USA, vol. 105, No. 31, pp. 10756-10761, Jun. 2008.
Yancopoulous et al., "Preferential Utilization of the Most JH-Proximal VH Gene Segments in Pre-B-Cell Lines," Nature, vol. 311, pp. 727-733, 1984.
Yang, et al., "Homologous Recombination Based Modification in *Esherichia coli* and Germline Transmission in Transgenic Mice of a Bacterial Artificial Chromosome," Nature Biotechnology, vol. 15, No. 9, pp. 859-865, Sep. 1997.
Yu, et al., Differential Usage of VH Gene Segments is Mediated by cis Elements, The Journal of Immunology, vol. 161, No. 7, pp. 3444-3454, Oct. 1, 1998.
Yu, et al., "Engineering Chromosomal Rearrangements in Mice," Nature Reviews Genetics, vol. 2, No. 10, pp. 780-790, Oct. 2001.
Zheng et al., Engineering Mouse Chromosomes with Cre-loxP: Range, Efficiency, and Somatic Applications, Molecular and Cellular Biology, vol. 20, No. 2, pp. 648-655, Jan. 2000.
Zhang, et al., "A New Logic for DNA Engineering Using Recombination in *Escherichia coli*," Nature Genetics, vol. 20, No. 2, pp. 123-128, Oct. 1998.
Zhao, Shaving, "A Comprehensive BAC Resource," Nucleic Acids Research, vol. 29, No. 1, Jan. 2001.
Zou et al., "Cre-loxP-mediated Gene Replacement: A Mouse Strain Producing Humanized Antibodies," Current Biology, vol. 4, No. 12, pp. 1099-1104, 1994.
Kling, "News in Brief," Nature Biotechnology, vol. 25, No. 6, p. 613, Jun. 2007.
GenBank Accession No. AC111740.4 GI:24818723, accessed Nov. 9, 2002, 42 pages.
GenBank Accession No. X97051 S64822, accessed Aug. 6, 2014, 29 pages.
Nucleotide Sequence RID Y55HBK1W114, accessed Aug. 6, 2014, 2 pages.
U.S. Appl. No. 13/310,431, filed Dec. 2, 2011.
U.S. Appl. No. 13/416,684, filed Mar. 9, 2012.
U.S. Appl. No. 13/433,084, filed Mar. 28, 2012.
U.S. Appl. No. 13/740,727, filed Jan. 14, 2013.
U.S. Appl. No. 13/846,672, filed Mar. 18, 2013.
U.S. Appl. No. 13/843,528, filed Mar. 15, 2013.
U.S. Appl. No. 13/875,892, filed May 2, 2013.
U.S. Appl. No. 13/886,511, filed May 3, 2013.
U.S. Appl. No. 13/890,147, filed May 8, 2013.
U.S. Appl. No. 14/040,427, filed Sep. 27, 2013.
U.S. Appl. No. 14/040,405, filed Sep. 27, 2013.
U.S. Appl. No. 14/052,259, filed Oct. 11, 2013.
U.S. Appl. No. 14/056,434, filed Oct. 17, 2013.
Ahmed T., "Sanofi-aventis and Regeneron Extend Therapeutic Antibody Agreement," PharmaDeals Review, Nov. 2009, vol. 11, p. 115.
Avery S., Attorney for Applicant, Third-Party Pre-Issuance Submission Under 37 CFR Section 1.290 in U.S. Appl. No. 14/517,755, dated Jun. 26, 2015, 16 pages.
Beerli R.R., et al., "Mining Human Antibody Repertoires," MAbs, Jul./Aug. 2010, vol. 2 (4), pp. 365-378.
Casrouge A., et al., ""Size Estimate of the dx TCR Repertoire, of Na' ve Mouse Splenocytes,"" The Journal of Immunology, 2000, vol. 164 (11), pp. 5782-5787.
Chan A.C., et al., "Therapeutic Antibodies for Autoimmunity and Inflammation," Nature Reviews Immunology, 2010, vol. 10 (5), pp. 301-316.
Chen Y., "PiggyBac Transposon-Mediated, Reversible Gene Transfer in Human Embryonic Stem Cells," Stem Cells and Development, Nov. 2010, vol. 19 (6), 9 pages.
Chinese Patent Office, First Office Action (English Translation) for Chinese Application No. 201180039668.1, dated Jan. 3, 2014, 6 pages.
Chinese Patent Office, First Office Action for Chinese Application No. 201180039668.1, dated Jan. 3, 2014, 6 pages.

(56) References Cited

OTHER PUBLICATIONS

Chinese Patent Office, Search Report, Chinese Application No. 201180039668.1, dated Jan. 3, 2014, 2 pages.
Chinese Patent Office, Search Report (English Translation), Chinese Patent Application No. 201180039668.1, dated Jan. 3, 2014, 1 page.
Crouch E.E., et al., "Regulation of AID expression in the Immune Response," Journal of Experimental Medicine, 2007, vol. 204 (5), pp. 1145-1156.
Ebert A., et al., "The Distal V(H) Gene Cluster of the IgH Locus Contains Distinct Regulatory Elements with Pax5 Transcription Factor-Dependent Activity in Pro-B Cells.," Immunity, 2011, vol. 34 (2), pp. 175-187.
European Patent Office, Alessando Brero, Examiner, International Search Report and Written Opinion for the International Searching Authority for Application No. PCT/GB2012/052297, dated Jun. 19, 2013, 24 pages.
European Patent Office, Communication pursuant to Article 94(3) EPC for Application No. 12194970.5, dated Sep. 23, 2013, 6 pages.
European Patent Office, Communication pursuant to Article 94(3) EPC for Application No. 14176740.0, dated Oct. 23, 2015, 5 pages.
European Patent Office, Extended European Search Report for Application No. 12171793.8 dated Jun. 21, 2013, 8 pages.
European Patent Office, Extended European Search Report for Application No. 12194970, dated Jan. 23, 2013, 9 pages.
European Patent Office, Extended European Search Report for Application No. 12194977.0, dated Jul. 17, 2013, 8 pages.
European Patent Office, Extended European Search Report for Application No. 14170196, dated Oct. 8, 2014, 8 pages.
European Patent Office, Extended European Search Report for Application No. 15188522.5 dated Feb. 2, 2016, 15 pages.
European Patent Office, Gaby Brouns, Authorized Officer, Examination Report for Application No. 12795841.1, dated Feb. 12, 2016, 5 pages.
European Patent Office, Gaby Brouns, Authorized Officer, Examination Report for Application No. 13711119.1, dated Dec. 17, 2015, 6 pages.
European Patent Office, Gaby Brouns, Examiner, International Search Report and Written Opinion for the International Searching Authority for Application No. PCT/GB2012/052960, dated Apr. 29, 2013, 19 pages.
European Patent Office, Gaby Brouns, Examiner, International Search Report and Written Opinion for the International Searching Authority for Application No. PCT/GB2013/050683, dated Jul. 9, 2013, 11 pages.
European Patent Office, International Searching Authority, Examiners Report on Allowable Claims for Application No. PCT/GB2010/051122, dated Jan. 2004, 1 page.
European Patent Office, Laurent Deleu, Authorized Officer, International Preliminary Report on Patentability Chapter II for Application No. PCT/GB2010/051122, dated Nov. 2, 2011, 33 pages.
European Patent Office, Laurent Deleu, Authorized Officer, Written Opinion for the International Searching Authority for Application No. PCT/GB2010/051122, dated Sep. 29, 2010, 6 pages.
European Patent Office, Laurent Deleu, Examiner, International Search Report and Written Opinion for the International Searching Authority, Application No. PCT/GB2011/050019, dated May 16, 2011, 12 pages.
European Patent Office, Third-Party Observations according to Article 114(2) EPC regarding 14772198.9, dated Mar. 30, 2016, 16 pages.
European Patent Office, Invitation to Pay Additional Fees and, Where Applicable, Protest Fee, Application No. PCT/GB2012/052296, dated Jan. 24, 2013, 9 pages.
Friedrich G., "Statement of Dr. Glenn Friedrich," Mar. 3, 2016, 4 pages.
Genbank, "*Homo sapiens* immunoglobulin heavy-chain (IGHV2-5) gene, IGHV2-5*10 allele, partial sequence," Accession No. KF698731.1, dated Nov. 18, 2013, 1 pages.

Goldman I.L., et al., "Transgenic Animals in Medicine: Integration and Expression of Foreign Genes, Theoretical and Applied Aspects," Medical Science Monitor, 2004, vol. 10 (11), pp. RA274-RA285.
Gratz S. et al., "Genome Engineering of *Drosophila* with the CRISPR RNA-Guided Cas9 Nuclease," Genetics, Aug. 2013, vol. 194, pp. 1029-1035.
Grund M., European Patent Attorney, Grund Intellectual Property Group, Third-Party Observations according to Article 115 EPC regarding 12762377.5, dated Feb. 12, 2016, 8 pages.
Grund M., European Patent Attorney, Grund Intellectual Property Group, Third-Party Observations according to Article 115 EPC regarding 12762377.5, dated May 22, 2015, 7 pages.
Grund M., European Patent Attorney, Grund Intellectual Property Group, Third-Party Observations according to Article 115 EPC regarding 13711119.1, dated Dec. 9, 2015, 7 pages.
Grund M., European Patent Attorney, Grund Intellectual Property Group, Third-Party Observations regarding Application No. PCT/GB2012/052956, dated Mar. 26, 2014, 2 pages.
Guirouilh-Barbat J. et al., "Is homologous recombination really an error-free process?", Frontiers in Genetics, Jun. 2014, vol. 5 (175), 15 pages.
Herschbach Jarrell B., Third-Party Pre-Issuance Submission Under 37 CFR Section 1.290 in U.S. Appl. No. 14/052,259, dated Aug. 6, 2014, 7 pages.
Hewitt S.L., et al., "Association Between the Lgk and Lgh Immunoglobulin Loci Mediated by the 3' Lgk Enhancer Induces 'decontraction' of the Lgh Locus in Pre-B Cells," Nature Immunology, 2008, vol. 9 (4), pp. 396-404.
Houdebine L.M., "The Methods to Generate Transgenic Animals and to Control Transgene Expression," Journal of Biotechnology, 2002, vol. 98 (2-3), pp. 145-160.
Houdebine L.M., "Transgenic Animal Models in Biomedical Research," Methods in Molecular Biology, Chapter 10, 2007, vol. 360, pp. 163-202.
Kondo S., "Highly improved Gene Targeting by Germline-Specific Cas9 Expression in *Drosophila*," Genetics, Nov. 2013, vol. 195, pp. 715-721 (Abstract).
Kondo S., "Highly improved Gene Targeting by Germline-Specific Cas9 Expression in *Drosophila*," Genetics, Nov. 2013, vol. 195, pp. 715-721.
Kuraoka M., et al., "AID Expression During B-Cell Development: Searching for Answers," Immunologic Research, 2011, vol. 49 (1-3), pp. 3-13.
Laffleur B., et al., "Production of Human or Humanized Antibodies in Mice," Chapter 9, Methods in Molecular Biology, 2012, vol. 901, pp. 149-159.
Lee E.C., et al., "The Application of Transgenic Mice for Therapeutic Antibody Discovery," Chapter 8, Methods in Molecular Biology, 2012, vol. 901, pp. 137-148.
Lefranc M.P., "Nomenclature of the Human Immunoglobulin Kappa (IGK) Genes," Experimental and Clinical Immunogenetics, 2001, vol. 18 (3), pp. 161-174.
Li H., et al., "Genetic Diversity of the Human Immunoglobulin Heavy Chain VH Region," Immunological Reviews, 2002, vol. 190, pp. 53-68.
Lonberg N., et al., "Fully Human Antibodies from Transgenic Mouse and Phage Display Platforms," Current Opinion in Immunology, 2008, vol. 20 (4), pp. 450-459.
Lyon C., Attorney for Applicant, Third-Party Pre-Issuance Submission Under 37 CFR Sec. 1.290 in U.S. Appl. No. 14/056,700, dated Nov. 28, 2014, 6 pages.
Lyon C., Attorney for Applicant, Third-Party Pre-Issuance Submission Under 37 CFR Sec. 1.290 in U.S. Appl. No. 14/056,707, dated Nov. 28, 2014, 10 pages.
Lyon C., Attorney for Applicant, Third-Party Pre-Issuance Submission Under 37 CFR Sec. 1.290 in U.S. Appl. No. 13/846,672, dated Mar. 17, 2015, 32 pages.
Lyon C., Attorney for Applicant, Third-Party Pre-Issuance Submission Under 37 CFR Sec. 1.290 in U.S. Appl. No. 13/875,892, dated May 5, 2015, 49 pages.

(56) References Cited

OTHER PUBLICATIONS

Lyon C., Attorney for Applicant, Third-Party Pre-Issuance Submission Under 37 CFR Sec. 1.290 in U.S. Appl. No. 13/886,511, dated May 5, 2015, 18 pages.
Lyon C., Attorney for Applicant, Third-Party Pre-Issuance Submission Under 37 CFR Sec. 1.290 in U.S. Appl. No. 14/040,427, dated Jan. 16, 2015, 20 pages.
Lyon C., Attorney for Applicant, Third-Party Pre-Issuance Submission Under 37 CFR Sec. 1.290 in U.S. Appl. No. 14/056,434, dated Dec. 15, 2014, 6 pages.
Lyon C., Attorney for Applicant, Third-Party Pre-Issuance Submission Under 37 CFR Sec. 1.290 in U.S. Appl. No. 14/080,630, dated Oct. 31, 2014, 8 pages.
Lyon C., Attorney for Applicant, Third-Party Pre-Issuance Submission Under 37 CFR Sec. 1.290 in U.S. Appl. No. 14/137,902, dated Nov. 13, 2014, 9 pages.
Lyon C., Attorney for Applicant, Third-Party Pre-Issuance Submission Under 37 CFR Sec. 1.290 in U.S. Appl. No. 14/220,080, dated Jul. 28, 2015, 28 pages.
Lyon C., Attorney for Applicant, Third-Party Pre-Issuance Submission Under 37 CFR Sec. 1.290 in U.S. Appl. No. 14/220,099, dated Apr. 29, 2015, 43 pages.
Lyon C., Attorney for Applicant, Third-Party Pre-Issuance Submission Under 37 CFR Sec. 1.290 in U.S. Appl. No. 14/226,706, dated Jul. 28, 2015, 53 pages.
Lyon C., Attorney for Applicant, Third-Party Pre-Issuance Submission Under 37 CFR Sec. 1.290 in U.S. Appl. No. 14/263,158, dated Apr. 29, 2015, 16 pages.
Lyon C., Attorney for Applicant, Third-Party Pre-Issuance Submission Under 37 CFR Sec. 1.290 in U.S. Appl. No. 14/263,176, dated Apr. 29, 2015, 16 pages.
Lyon C., Attorney for Applicant, Third-Party Pre-Issuance Submission Under 37 CFR Sec. 1.290 in U.S. Appl. No. 14/497,054, dated Oct. 21, 2015, 81 pages.
Lyon C., Attorney for Applicant, Third-Party Pre-Issuance Submission Under 37 CFR Sec. 1.290 in U.S. Appl. No. 14/498,685, dated Sep. 18, 2015, 37 pages.
Lyon C., Attorney for Applicant, Third-Party Pre-Issuance Submission Under 37 CFR Sec. 1.290 in U.S. Appl. No. 14/516,461, dated Aug. 4, 2015, 27 pages.
Lyon C., Attorney for Applicant, Third-Party Pre-Issuance Submission Under 37 CFR Sec. 1.290 in U.S. Appl. No. 14/226,698, dated Jun. 3, 2015, 53 pages.
Macdonald L., Curriculum Vitae of Lynn E. MacDonald, Ph.D., 3 pages.
Macdonald L., et al., Poster: "Velocimmune Technology Extended to Humanization of Several Megabases of Complex" and evidence of unavailability (Exhibit IJR-47), 42 pages (2006).
Macdonald L., et al., Expanded Poster: "Velocimmune Technology Extended to Humanization of Several Megabases of Complex," 6 pages.
Magadan S., et al., "Production of Antigen-Specific Human Monoclonal Antibodies: Comparison of Mice Carrying IgH/kappa or IgH/kappa/lambda transloci," Biotechniques, 2002, vol. 33 (3), pp. 680, 682, 684 passim.
Martinez-Jean C., et al., "Nomenclature and Overview of the Mouse (Mus musculus and Mus sp.) Immunoglobulin Kappa (IGK) Genes," Experimental and Clinical Immunogenetics, 2001, vol. 18 (4), pp. 255-279.
Mills F., et al., "Enhancer Complexes Located Downstream of Both Human Immunoglobulin Ca Genes," The Journal of Experimental Medicine, Sep. 1997, vol. 186 (6), pp. 845-858.
Neuberger M.S., "Expression and regulation of immunoglobulin heavy chain gene transfected into lymphoid cells," The EMBO Journal, 1983, vol. 2 (8), pp. 1373-1378.
New Zealand Patent Office, Simon Maguire, Authorized Officer, Further Examination Report for Patent No. 623756, dated Sep. 9, 2015, 3 pages.
Pear W.S., et al., "Localization of the Rat Immunoglobulin Heavy Chain Locus to Chromosome 6," Immunogenetics, 1986, vol. 23 (6), pp. 393-395.
Pettersson S., et al., "A second B cell-specific enhancer 3' of the immunoglobulin heavy-chain locus," Nature, Mar. 1990, vol. 344, pp. 165-168.
Pobursky K., Third-Party Pre-Issuance Submission Under 37 CFR 1.290 in U.S. Appl. No. 13/843,528, dated Mar. 18, 2014, 14 pages.
Pobursky K., Third-Party Pre-Issuance Submission Under 37 CFR 1.290 in U.S. Appl. No. 13/433,084, dated Apr. 1, 2014, 15 pages.
Pobursky K., Third-Party Pre-Issuance Submission Under 37 CFR 1.290 in U.S. Appl. No. 13/434,361, dated Apr. 1, 2014, 15 pages.
Pobursky K., Third-Party Pre-Issuance Submission Under 37 CFR 1.290 in U.S. Appl. No. 13/740,727, dated May 27, 2014, 25 pages.
Regeneron Pharmaceuticals, Inc., Press Release6—"Astellas Licenses Regeneron's Velocimmune Technology for Discovering Human Monoclonal Antibodies," dated Mar. 30, 2007, 2 pages.
Regeneron Pharmaceuticals, Inc., Press Release—"AstraZeneca Licenses Regeneron's VelocImmune Technology for Discovering Human Monoclonal Antibodies—AstraZeneca Is First Licensee of Novel Velocimmune Technology License Fees Total up to $120 Million Over Six Years," Feb. 5, 2007, 2 pages.
Regeneron Pharmaceuticals, Inc., Press Release—"Regeneron Initiates Major Global Collaboration wtih Sanofi-aventis of Develop and Commercialize Fully-Human Therapeutic Antibodies," Nov. 29, 2007, 2 pages.
Rourke J., Declaration of Jeffrey Rourke, Registered Patent Attorney for Regeneron Pharmaceuticals, Inc.—In the matter of Patent Acceptance 2011266843 in the Name of Kymab Limited and in the Matter of Opposition thereto by Regeneron Pharmaceuticals, Inc., dated Jan. 29, 2016, 5 pages.
Sekiguchi J., et al., "The Mechanism of V(D)J Recombination," Molecular Biology of B Cells, Chapter 5, Elsevier Academic Press, 2004, pp. 61-82.
Sigmund C.D., "Viewpoint: Are Studies in Genetically Altered Mice Out of Control?," Arteriosclerosis, Thrombosis, and Vascular Biology, 2000, vol. 20 (6), pp. 1425-1429.
Stephen R., Kymab Limited Statement of Facts and Evidence in opposition to EP2550363, Olswang LLP, dated Sep. 10, 2015, 22 pages.
Stevens S., et al., Poster: "VelocImmuneTM: Humanization of immunoglobulin loci using VelociGene technology," and evidence of unavailability (Exhibit IJR-46), 42 pages (2006).
Stevens S., et al., Expanded poster: "VelocImmuneTM: Humanization of immunoglobulin loci using VolociGene technology," 2006, 6 pages.
Tanimoto Y., et al., "Embryonic Stem Cells Derived from C5761/6J and C57BL/6N Mice," Comparative Medicine, 2008, vol. 58 (4), pp. 347-352.
Tuaillon N., et al., "Human immunoglobulin heavy-chain minilocus recombination in transgenic mice: Gene-segment use in μ and γtranscripts," Proc. Natl. Acad. Sci. USA, Apr. 1993, vol. 90, pp. 3720-3724.
United Kingdom Intellectual Property Office, Combined Search and Examination Report under Sections 17 and 18(3) for Application No. GB1317410.7, dated Nov. 21, 2013, 8 pages.
United Kingdom Intellectual Property Office, Corrected International Search Report and Opinion for Application No. GB1122047.2, dated Apr. 20, 2012, 5 pages.
United Kingdom Intellectual Property Office, International Search Report for Application No. GB1116122.1, dated Feb. 2, 2012, 1 page.
Urquhart-Dykes & Lord LLP, Third-Party Observation for Application No. EP20140772198, dated Dec. 14, 2015, 8 pages.
Wasserman R., et al., "The Pattern of Joining (JH) Gene Usage in the Human IgH Chain Is Established Predominantly at the B PreCursor Cell Stage," The Journal of Immunology, vol. 149 (2), Jul. 1992, pp. 511-516.
Weichhold G.M., et al., "Megabase Inversions in the Human Genome as Physiological Events," Nature, 1990, vol. 347 (6288), pp. 90-92.

(56) References Cited

OTHER PUBLICATIONS

Weichhold G.M., et al., "The Human Immunoglobulin Kappa Locus Consists of Two Copies that are Organized in Opposite Polarity," Genomics, 1993, vol. 16 (2), pp. 503-511.
Weiner L.M., et al., "Fully Human Therapeutic Monoclonal Antibodies," Journal of Immunology, 2006, vol. 29 (1), pp. 1-9.
Williams K., Attorney for Applicant, Third-Party Pre-Issuance Submission Under 37 CFR 1.290 in U.S. Appl. No. 14/600,829, dated Apr. 1, 2016, 18 pages.
Williams K., Attorney for Applicant, Third-Party Pre-Issuance Submission Under 37 CFR 1.290 in U.S. Appl. No. 14/679,949, dated Apr. 1, 2016, 18 pages.
Yamada M., et al., "Preferential Utilization of Specific Immunoglobulin Heavy Chain Diversity and Joining Segments in Adult Human Peripheral Bood B Lymphocytes," Journal of Experimental Medicine, Feb. 1991, vol. 173, pp. 395-407.
Zheng J., et al., "Immunoglobulin Gene Transcripts Have distinctive VHDJH Recombination Characteristics in Human Epithelial Cancer Cells", J. Biol. Chem., Mar. 2009, vol. 284 (20), pp. 13610-13619.
Zou X., et al., "Removal of the BiP-Retention Domain in Cmicro Permits Surface Deposition and Developmental Progression Without L-Chain," Molecular Immunology, 2008, vol. 45 (13), pp. 3573-3579.
Affidavits Evidencing Murphy Slides as Printed Publication, 84 pages, dated Jun. 20, 2016.
Aguilera R.J. et al., "Characterization of immunoglobulin enhancer deletions in murine plasmacytomas," The EMBO Journal, 1985, vol. 4 (13B), pp. 3689-3693.
Board of Appeal of the European Patent Office, Datasheet for the Decision of Nov. 9, 2015 for Application No. 02709544.7, Case T 2220/14-3.3.08, 83 pages.
Deftos, M., et al., "Defining the Genetic Origins of Three Rheumatoid Synovium-derived IgG Rheumatoid Factors," Journal of Clinical Investigations, Jun. 1994, vol. 93, pp. 2545-2553.
Donohoe M.E., et al., "Transgenic Human λ5 Rescues the Murine λ5 Nullizygous Phenotype," Journal of Immunology, 2000, vol. 164, pp. 5269-5276.
European Patent Office, Examination Report for Application No. 12762378.3, dated Jun. 8, 2016, 5 pages.
European Patent Office, Examination Report for Application No. 13711119.1, dated Jul. 13, 2016, 6 pages.
European Patent Office, Examination Report for Application No. 14176740.0, dated Jun. 6, 2016, 5 pages.
European Patent Office, International Search Report and Written Opinion for Application No. PCT/GB2012/052380, dated Jan. 3, 2013, 17 pages.
European Patent Office, International Search Report and Written Opinion for Application No. PCT/GB2012/052670, dated Feb. 14, 2013, 12 pages.
Grund M., European Patent Attorney, Grund Intellectual Property Group, Third-Party Observations according to Article 115 EPC regarding 12772122.3, dated May 17, 2016, 7 pages.
Grund M., European Patent Attorney, Grund Intellectual Property Group, Third-Party Observations according to Article 115 EPC regarding 13711119.1, dated Jul. 5, 2016, 7 pages.
Grund M., European Patent Attorney, Grund Intellectual Property Group, Third-Party Observations according to Article 115 EPC regarding 13711120.9, dated May 17, 2016, 11 pages.
Guo Y., et al., "A Preliminary Analysis of the Immunoglobulin Genes in the African Elephant (*Loxodonta Africana*)," PLoS ONE, Feb. 2011, vol. 6 (2), pp. e16889-1-e16889-14.
Huang D., et al., "Sequence Analyses of Three Immunoglobulin G Anti-virus Antibodies Reveal Their Utilization of Autoantibody-related Immunoglobulin Vh Genes, but Not Vλ Genes," Journal of Clinical Investigations, Dec. 1992, vol. 90, pp. 2197-2208.
Jasper P.J., et al., "B lymphocyte deficiency in IgH-transgenic rabbits," European Journal of Immunology, 2007, vol. 37, pp. 2290-2299.
LeFranc M.P., et al., "The Immunoglobulin Facts Book—Annex 3," IGHJ group, Academic Press, ISBN:9-12-441351-X, 2001, 4 pages.
Minaee S., et al., "Mapping and Functional Analysis of Regulatory Sequences in the Mouse Lambda5-VpreB1 Domain," Molecular Immunology, 2005, vol. 42 (11), pp. 1283-1292.
Mullins, L.J., et al., "Perspective Series: Molecular Medicine in Genetically Engineered Animals," Journal of Clinical Investigation, Apr. 1996, vol. 97 (7), pp. 1557-1560.
Pera, M.F., et al., "Human embryonic stem cells," Journal of Cell Science, 2000, vol. 113, pp. 5-10.
Sabbattini P., et al., "Analysis of Mice with Single and Multiple Copies of Transgenes Reveals a Novel Arrangement for the λ5-$V_{preB1}$ Locus Control Region," Molecular and Cellular Biology, Jan. 1999, vol. 19 (1), pp. 671-679.
Schonewald, S.L., Attorney for Applicant, Third-Party Pre-Issuance Submission Under 37 CFR Sec. 1.290 in U.S. Appl. No. 14/220,074, dated Jul. 12, 2016, 46 pages.
Schonewald, S.L., Attorney for Applicant, Third-Party Pre-Issuance Submission Under 37 CFR Sec. 1.290 in U.S. Appl. No. 14/750,870, dated Aug. 10, 2016, 34 pages.
Schonewald, S.L., Attorney for Applicant, Third-Party Pre-Issuance Submission Under 37 CFR Sec. 1.290 in U.S. Appl. No. 14/818,162, dated May 24, 2016, 47 pages.
Tong C., et al., "Production of p53 gene knockout rats by homologous recombination in embryonic stem cells," Nature, Sep. 2010, vol. 467 (7312), pp. 211-213.
Van Loo, P.F., et al., "Surrogate-Light-Chain Silencing Is Not Critical for the Limitation of Pre-B Cell Expansion but Is for the Termination of Constitutive Signaling," Immunity, Sep. 2007, vol. 27, pp. 468-480.
U.S. Appl. No. 14/056,700, filed Oct. 17, 2013.
U.S. Appl. No. 14/056,707, filed Oct. 17, 2013.
U.S. Appl. No. 14/080,630, filed Nov. 14, 2013.
U.S. Appl. No. 14/137,902, filed Dec. 20, 2013.
U.S. Appl. No. 14/543,359, filed Nov. 17, 2014.
U.S. Appl. No. 14/220,080, filed Mar. 19, 2014.
U.S. Appl. No. 14/220,074, filed Mar. 19, 2014.
U.S. Appl. No. 14/220,099, filed Mar. 19, 2014.
U.S. Appl. No. 14/226,698, filed Mar. 26, 2014.
U.S. Appl. No. 14/226,706, filed Mar. 26, 2014.
U.S. Appl. No. 14/263,158, filed Apr. 28, 2014.
U.S. Appl. No. 14/263,176, filed Apr. 28, 2014.
U.S. Appl. No. 14/498,685, filed Sep. 26, 2014.
U.S. Appl. No. 14/497,054, filed Sep. 25, 2014.
U.S. Appl. No. 14/516,461, filed Oct. 16, 2014.
U.S. Appl. No. 14/750,870, filed Jun. 25, 2015.
U.S. Appl. No. 14/818,162, filed Aug. 4, 2015.
U.S. Appl. No. 14/935,010, filed Nov. 6, 2015.
U.S. Appl. No. 15/016,211, filed Feb. 4, 2016.
U.S. Appl. No. 15/018,670, filed Feb. 8, 2016.
U.S. Appl. No. 15/088,805, filed Apr. 1. 2016.
U.S. Appl. No. 15/095,315, filed Apr. 11, 2016.
U.S. Appl. No. 15/199,575, filed Jun. 30, 2016.
U.S. Appl. No. 15/214,963, filed Jul. 20, 2016.
U.S. Appl. No. 15/232,122, filed Aug. 9, 2016.
Lefranc, Marie-Paule, and Gérard Lefranc. Immunoglobulin Facts Book. London: Academic Press, 2001. Print. (pp. 1-428).†

\* cited by examiner
† cited by third party

Figure 5A

Alignment of 13 IGHV1-69 alleles showing the variable (V) coding region only. Nucleotides that differ from VH1-69 allele *01 are indicated at the appropriate position whereas identical nucleotides are marked with a dash. Where nucleotide changes result in amino acid differences, the encoded amino acid is shown above the corresponding triplet. Boxed regions correspond to CDR1, CDR2 and CDR3 as indicated.

Figure 5B

Alignment of 13 IGHV1-69 alleles showing the variable (V) coding region only. Nucleotides that differ from VH1-69 allele *01 are indicated at the appropriate position whereas identical nucleotides are marked with a dash. Where nucleotide changes result in amino acid differences, the encoded amino acid is shown above the corresponding triplet. Boxed regions correspond to CDR1, CDR2 and CDR3 as indicated.

Alignment of 13 IGHV1-69 alleles showing the variable (V) coding region only. Nucleotides that differ from VH1-69 allele *01 are indicated at the appropriate position whereas identical nucleotides are marked with a dash. Where nucleotide changes result in amino acid differences, the encoded amino acid is shown above the corresponding triplet. Boxed regions correspond to CDR1, CDR2 and CDR3 as indicated.

SEQUENCE LISTING

```
<160> NUMBER OF SEQ ID NOS: 50

<210> SEQ ID NO 1
<211> LENGTH: 296
<212> TYPE: DNA
<213> ORGANISM: Homo sapiens

<400> SEQUENCE: 1
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc    120
cctggacaag gcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagaga         296

<210> SEQ ID NO 2
<211> LENGTH: 98
<212> TYPE: PRT
<213> ORGANISM: Homo sapiens

<400> SEQUENCE: 2

Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 3
<211> LENGTH: 98
<212> TYPE: PRT
<213> ORGANISM: Homo sapiens
```

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 4
<211> LENGTH: 296
<212> TYPE: DNA
<213> ORGANISM: homo sapiens;

<400> SEQUENCE: 4
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gccttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaga         296

<210> SEQ ID NO 5
<211> LENGTH: 98
<212> TYPE: PRT
<213> ORGANISM: Homo sapiens

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 6
<211> LENGTH: 296
<212> TYPE: DNA
<213> ORGANISM: Homo sapiens

<400> SEQUENCE: 6
caggtccagc tggtgcaatc tggggctgag gtgaagaagc ctgggtcctc ggtgaaggtc      60

```
tcctgcaagg cttctggagg caccttcagc agctatacta tcagctgggt gcgacaggcc    120
cctggacaag ggcttgagtg gatgggaagg atcatcccta tccttggtat agcaaactac    180
gcacagaagt tccagggcag agtcacgatt accgcggaca atccacgag cacagcctac     240 atggagctga gcagcctgag atctgaggac acggccgtgt attactgtgc gagaga        296
```

<210> SEQ ID NO 7
<211> LENGTH: 91
<212> TYPE: PRT
<213> ORGANISM: Homo sapiens

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr
                85                  90
```

<210> SEQ ID NO 8
<211> LENGTH: 274
<212> TYPE: DNA
<213> ORGANISM: Homo sapiens

<400> SEQUENCE: 8

```
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgatgac acgg                                 274
```

<210> SEQ ID NO 9
<211> LENGTH: 98
<212> TYPE: PRT
<213> ORGANISM: Homo sapiens

<400> SEQUENCE: 9

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 10
<211> LENGTH: 296
<212> TYPE: DNA
<213> ORGANISM: Homo sapiens

<400> SEQUENCE: 10

```
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaagg atcatccta tccttggtat agcaaactac       180
gcacagaagt tccagggcag agtcacgatt accgcggaca atccacgag cacagcctac      240
atggagctga gcagcctgag atctgaggac acggccgtgt attactgtgc gagaga         296
```

<210> SEQ ID NO 11
<211> LENGTH: 98
<212> TYPE: PRT
<213> ORGANISM: Homo sapiens

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 12
<211> LENGTH: 294
<212> TYPE: DNA
<213> ORGANISM: Homo sapiens

<400> SEQUENCE: 12

```
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatccta tctttggtac agcaaactac       180
gcacagaagt tccagggcag agtcacgatt accacggacg aatccacgag cacagcctac     240
atggagctga gcagcctgag atctgaggac acggccgtgt attactgtgc gaga           294
```

<210> SEQ ID NO 13
<211> LENGTH: 98
<212> TYPE: PRT
<213> ORGANISM: Homo sapiens

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

```
Ala Ile Ser Trp Val Arg Gln Ala Pro Gly Gln Gly Leu Glu Trp Met
             35                  40                  45
Gly Gly Ile Ile Pro Ile Phe Gly Thr Ala Asn Tyr Ala Gln Lys Phe
 50                  55                  60
Gln Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg

<210> SEQ ID NO 14
<211> LENGTH: 296
<212> TYPE: DNA
<213> ORGANISM: Homo sapiens

<400> SEQUENCE: 14
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaggg atcatcccta tctttggtac agcaaactac   180
gcacagaagt tccagggcag agtcacgatt accgcggaca atccacgag cacagcctac   240 atggagctga gcagcctgag atctgaggac acggccgtgt attactgtgc gagaga       296

<210> SEQ ID NO 15
<211> LENGTH: 77
<212> TYPE: PRT
<213> ORGANISM: Homo sapiens

<400> SEQUENCE: 15

Lys Pro Gly Ser Ser Val Lys Val Ser Cys Lys Ala Ser Gly Gly Thr
  1               5                  10                  15

Phe Ser Ser Tyr Ala Ile Ser Trp Val Arg Gln Ala Pro Gly Gln Gly
                 20                  25                  30

Leu Glu Trp Met Gly Arg Ile Ile Pro Ile Phe Gly Thr Ala Asn Tyr
             35                  40                  45

Ala Gln Lys Phe Gln Gly Arg Val Thr Ile Thr Ala Asp Glu Ser Thr
 50                  55                  60

Ser Thr Ala Tyr Met Glu Leu Ser Ser Leu Arg Ser Glu
 65                  70                  75

<210> SEQ ID NO 16
<211> LENGTH: 233
<212> TYPE: DNA
<213> ORGANISM: Homo sapiens

<400> SEQUENCE: 16
agaagcctgg gtcctcggtg aaggtctcct gcaaggcttc tggaggcacc ttcagcagct    60
atgctatcag ctgggtgcga caggcccctg acaagggct tgagtggatg gaaggatca   120 tccctatctt tggtacagca aactacgcac agaagttcca gggcagagtc acgattaccg   180
cggacgaatc cacgagcaca gcctacatgg agctgagcag cctgagatct gag         233

<210> SEQ ID NO 17
<211> LENGTH: 98
<212> TYPE: PRT
<213> ORGANISM: Homo sapiens

<400> SEQUENCE: 17
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 18
<211> LENGTH: 296
<212> TYPE: DNA
<213> ORGANISM: Homo sapiens

<400> SEQUENCE: 18
caggtccagc tggtgcaatc tggggctgag gtgaagaagc ctgggtcctc ggtgaaggtc      60
tcctgcaagg cttctggagg caccttcagc agctatacta tcagctgggt gcgacaggcc    120
cctggacaag gccttgagtg gatgggaagg atcatcccta tccttggtac agcaaactac    180
gcacagaagt tccagggcag agtcacgatt accgcggaca atccacgag cacagcctac     240 atggagctga gcagcctgag atctgaggac acggccgtgt attactgtgc gagaga         296

<210> SEQ ID NO 19
<211> LENGTH: 98
<212> TYPE: PRT
<213> ORGANISM: Homo sapiens

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 20
<211> LENGTH: 296
<212> TYPE: DNA
<213> ORGANISM: Homo sapiens

<400> SEQUENCE: 20
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc    120
cctggacaag gccttgagtg gatgggaagg atcatcccta tccttggtat agcaaactac    180

```
gcacagaagt tccagggcag agtcacgatt accgcggaca aatccacgag cacagcctac    240
atggagctga gcagcctgag atctgaggac acggccgtgt attactgtgc gagaga        296
```

<210> SEQ ID NO 21
<211> LENGTH: 98
<212> TYPE: PRT
<213> ORGANISM: Homo sapiens

<400> SEQUENCE: 21

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 22
<211> LENGTH: 296
<212> TYPE: DNA
<213> ORGANISM: Homo sapiens

<400> SEQUENCE: 22

```
caggtccagc tggtgcagtc tggggctgag gtgaagaagc ctgggtcctc agtgaaggtc    60
tcctgcaagg cttctggagg cacctttagc agctatgcta tcagctgggt gcgacaggcc   120
cctggacaag gcttgagtg gatgggaggg atcatcccta tccttggtat agcaaactac    180
gcacagaagt tccagggcag agtcacgatt accgcggaca aatccacgag cacagcctac    240
atggagctga gcagcctgag atctgaggac acggccgtgt attactgtgc gagaga        296
```

<210> SEQ ID NO 23
<211> LENGTH: 98
<212> TYPE: PRT
<213> ORGANISM: Homo sapiens

<400> SEQUENCE: 23

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 24
<211> LENGTH: 296
<212> TYPE: DNA
<213> ORGANISM: Homo sapiens

<400> SEQUENCE: 24
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaagg atcatccsta tccttggtac agcaaactac     180
gcacagaagt tccagggcag agtcacgatt accgcggacg aatccacgag cacagcctac     240
atggagctga gcagcctgag atctgaggac acggccgtgt attactgtgc gagaga         296

<210> SEQ ID NO 25
<211> LENGTH: 296
<212> TYPE: DNA
<213> ORGANISM: Homo sapiens

<400> SEQUENCE: 25
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatccsta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaga         296

<210> SEQ ID NO 26
<211> LENGTH: 296
<212> TYPE: DNA
<213> ORGANISM: Homo sapiens

<400> SEQUENCE: 26
caggtccagc tggtgcagtc tggggctgag gtgaagaagc ctgggtcctc agtgaaggtc      60
tcctacaagg cttctggagg caccttcagc agctatgcta tcagctgggt gcgacaggcc     120
cctggacaag ggcttgagtg gatgggaggg atcatccsta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaga         296

<210> SEQ ID NO 27
<211> LENGTH: 296
<212> TYPE: DNA
<213> ORGANISM: homo sapiens;

<400> SEQUENCE: 27
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatccsta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaga         296

<210> SEQ ID NO 28
<211> LENGTH: 98
<212> TYPE: PRT
<213> ORGANISM: Homo sapiens

<400> SEQUENCE: 28

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 29
<211> LENGTH: 296
<212> TYPE: DNA
<213> ORGANISM: Homo sapiens

<400> SEQUENCE: 29

```
caggtccagc tggtgcaatc tggggctgag gtgaagaagc ctgggtcctc ggtgaaggtc    60
tcctgcaagg cttctggagg cacctccagc agctatacta tcagctgggt gcgacaggcc   120
cctggacaag ggcttgagtg gatgggaagg atcatcccta tccttggtat agcaaactac   180
gcacagaagt tccagggcag agtcacgatt accgcggaca atccacgag cacagcctac    240
atggagctga gcagcctgag atctgaggac acggccgtgt attactgtgc gagaga        296
```

<210> SEQ ID NO 30
<211> LENGTH: 274
<212> TYPE: DNA
<213> ORGANISM: Homo sapiens

<400> SEQUENCE: 30

```
caggtgcagc tggtgcagtc tggggctgag gtgaagaagc ctgggtcctc ggtgaaggtc    60
tcctgcaagg cttctggagg cacctccagc agctatgcta tcagctgggt gcgacaggcc   120
cctggacaag ggcttgagtg gatgggaggg atcatcccta tctttggtac agcaaactac   180
gcacagaagt tccagggcag agtcacgatt accgcggacg aatccacgag cacagcctac    240
atggagctga gcagcctgag atctgatgac acgg                                274
```

<210> SEQ ID NO 31
<211> LENGTH: 296
<212> TYPE: DNA
<213> ORGANISM: Homo sapiens

<400> SEQUENCE: 31

```
caggtccagc tggtgcagtc tggggctgag gtgaagaagc ctgggtcctc ggtgaaggtc    60
tcctgcaagg cttctggagg cacctccagc agctatgcta tcagctgggt gcgacaggcc   120
cctggacaag ggcttgagtg gatgggaagg atcatcccta tccttggtat agcaaactac   180
gcacagaagt tccagggcag agtcacgatt accgcggaca atccacgag cacagcctac    240
atggagctga gcagcctgag atctgaggac acggccgtgt attactgtgc gagaga        296
```

<210> SEQ ID NO 32
<211> LENGTH: 294
<212> TYPE: DNA

<213> ORGANISM: Homo sapiens

<400> SEQUENCE: 32

| | | | | | |
|---|---|---|---|---|---|
| caggtccagc | tggtgcagtc | tggggctgag | gtgaagaagc | ctgggtcctc | ggtgaaggtc | 60 |
| tcctgcaagg | cttctggagg | caccttcagc | agctatgcta | tcagctgggt | gcgacaggcc | 120 |
| cctggacaag | ggcttgagtg | gatgggaggg | atcatccta | tctttggtac | agcaaactac | 180 |
| gcacagaagt | tccagggcag | agtcacgatt | accacggacg | aatccacgag | cacagcctac | 240 |
| atggagctga | gcagcctgag | atctgaggac | acggccgtgt | attactgtgc | gaga | 294 |

<210> SEQ ID NO 33
<211> LENGTH: 296
<212> TYPE: DNA
<213> ORGANISM: Homo sapiens

<400> SEQUENCE: 33

| | | | | | |
|---|---|---|---|---|---|
| caggtgcagc | tggtgcagtc | tggggctgag | gtgaagaagc | ctgggtcctc | ggtgaaggtc | 60 |
| tcctgcaagg | cttctggagg | caccttcagc | agctatgcta | tcagctgggt | gcgacaggcc | 120 |
| cctggacaag | ggcttgagtg | gatgggaggg | atcatccta | tctttggtac | agcaaactac | 180 |
| gcacagaagt | tccagggcag | agtcacgatt | accgcggaca | aatccacgag | cacagcctac | 240 |
| atggagctga | gcagcctgag | atctgaggac | acggccgtgt | attactgtgc | gagaga | 296 |

<210> SEQ ID NO 34
<211> LENGTH: 233
<212> TYPE: DNA
<213> ORGANISM: Homo sapiens

<400> SEQUENCE: 34

| | | | | | |
|---|---|---|---|---|---|
| agaagcctgg | gtcctcggtg | aaggtctcct | gcaaggcttc | tggaggcacc | ttcagcagct | 60 |
| atgctatcag | ctgggtgcga | caggcccctg | gacaagggct | tgagtggatg | ggaaggatca | 120 |
| tccctatctt | tggtacagca | aactacgcac | agaagttcca | gggcagagtc | acgattaccg | 180 |
| cggacgaatc | cacgagcaca | gcctacatgg | agctgagcag | cctgagatct | gag | 233 |

<210> SEQ ID NO 35
<211> LENGTH: 296
<212> TYPE: DNA
<213> ORGANISM: Homo sapiens

<400> SEQUENCE: 35

| | | | | | |
|---|---|---|---|---|---|
| caggtccagc | tggtgcaatc | tggggctgag | gtgaagaagc | ctgggtcctc | ggtgaaggtc | 60 |
| tcctgcaagg | cttctggagg | caccttcagc | agctatacta | tcagctgggt | gcgacaggcc | 120 |
| cctggacaag | ggcttgagtg | gatgggaagg | atcatccta | tccttggtac | agcaaactac | 180 |
| gcacagaagt | tccagggcag | agtcacgatt | accgcggaca | aatccacgag | cacagcctac | 240 |
| atggagctga | gcagcctgag | atctgaggac | acggccgtgt | attactgtgc | gagaga | 296 |

<210> SEQ ID NO 36
<211> LENGTH: 296
<212> TYPE: DNA
<213> ORGANISM: Homo sapiens

<400> SEQUENCE: 36

| | | | | | |
|---|---|---|---|---|---|
| caggtgcagc | tggtgcagtc | tggggctgag | gtgaagaagc | ctgggtcctc | ggtgaaggtc | 60 |
| tcctgcaagg | cttctggagg | caccttcagc | agctatgcta | tcagctgggt | gcgacaggcc | 120 |
| cctggacaag | ggcttgagtg | gatgggaggg | atcatccta | tctttggtac | agcaaactac | 180 |

```
gcacagaagt tccagggcag agtcacgatt accgcggacg aatccacgag cacagcctac    240
atggagctga gcagcctgag atctgaggac acggccgtgt attactgtgc gagaga        296

<210> SEQ ID NO 37
<211> LENGTH: 296
<212> TYPE: DNA
<213> ORGANISM: Homo sapiens

<400> SEQUENCE: 37
caggtccagc tggtgcagtc tggggctgag gtgaagaagc ctgggtcctc agtgaaggtc    60
tcctgcaagg cttctggagg caccttcagc agctatgcta tcagctgggt gcgacaggcc   120
cctggacaag ggcttgagtg gatgggaggg atcatcccta tccttggtat agcaaactac   180
gcacagaagt tccagggcag agtcacgatt accgcggaca aatccacgag cacagcctac   240
atggagctga gcagcctgag atctgaggac acggccgtgt attactgtgc gagaga        296

<210> SEQ ID NO 38
<211> LENGTH: 296
<212> TYPE: DNA
<213> ORGANISM: Homo sapiens

<400> SEQUENCE: 38
caggtccagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag ggcttgagtg gatgggaagg atcatcccta tctctggtac agcaaactac   180
gcacagaagt tccagggcag agtcacgatt accgcggacg aatccacgag cacagcctac   240
atggagctga gcagcctgag atctgaggac acggccgtgt attactgtgc gagaga        296

<210> SEQ ID NO 39
<211> LENGTH: 296
<212> TYPE: DNA
<213> ORGANISM: Homo sapiens

<400> SEQUENCE: 39
caggtccagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag ggcttgagtg gatgggaggg atcatcccta tctttggtac agcaaactac   180
gcacagaagt tccagggcag agtcacgatt accgcggacg aatccacgag cacagcctac   240
atggagctga gcagcctgag atctgaggac acggccgtgt attactgtgc gagaga        296

<210> SEQ ID NO 40
<211> LENGTH: 296
<212> TYPE: DNA
<213> ORGANISM: Homo sapiens

<400> SEQUENCE: 40
caggcgcagc tggtgcagtc tggggctgag gtgaagaagc ctgggtcctc ggtgaaggtc    60
tcctacaagg cttctggagg caccttcagc agctatgcta tcagctgggt gcgacaggcc   120
cctggacaag ggcttgagtg gatgggaggg atcatcccta tctttggtac agcaaactac   180
gcacagaagt tccagggcag agtcacgatt accgcggacg aatccacgag cacagcctac   240
atggagctga gcagcctgag atctgaggac acggccgtgt attactgtgc gagaga        296

<210> SEQ ID NO 41
```

```
<211> LENGTH: 98
<212> TYPE: PRT
<213> ORGANISM: Homo sapiens

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Leu Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 42
<211> LENGTH: 91
<212> TYPE: PRT
<213> ORGANISM: Homo sapiens

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr
                85                  90

<210> SEQ ID NO 43
<211> LENGTH: 98
<212> TYPE: PRT
<213> ORGANISM: Homo sapiens

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 44
<211> LENGTH: 98
<212> TYPE: PRT
<213> ORGANISM: Homo sapiens

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 45
<211> LENGTH: 98
<212> TYPE: PRT
<213> ORGANISM: Homo sapiens

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 46
<211> LENGTH: 77
<212> TYPE: PRT
<213> ORGANISM: Homo sapiens

<400> SEQUENCE: 46

Lys Pro Gly Ser Ser Val Lys Val Ser Cys Lys Ala Ser Gly Gly Thr
1               5                   10                  15

Phe Ser Ser Tyr Ala Ile Ser Trp Val Arg Gln Ala Pro Gly Gln Gly
            20                  25                  30

Leu Glu Trp Met Gly Arg Ile Ile Pro Ile Phe Gly Thr Ala Asn Tyr
        35                  40                  45

Ala Gln Lys Phe Gln Gly Arg Val Thr Ile Thr Ala Asp Glu Ser Thr
    50                  55                  60

Ser Thr Ala Tyr Met Glu Leu Ser Ser Leu Arg Ser Glu
65                  70                  75

<210> SEQ ID NO 47
<211> LENGTH: 98
<212> TYPE: PRT
<213> ORGANISM: Homo sapiens

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 48
<211> LENGTH: 98
<212> TYPE: PRT
<213> ORGANISM: Homo sapiens

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 49
<211> LENGTH: 98
<212> TYPE: PRT
<213> ORGANISM: Homo sapiens

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg

<210> SEQ ID NO 50
<211> LENGTH: 98
<212> TYPE: PRT
<213> ORGANISM: Homo sapiens

<400> SEQUENCE: 50

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

MANIPULATION OF IMMUNOGLOBULIN GENE DIVERSITY AND MULTI-ANTIBODY THERAPEUTICS

CROSS REFERENCE

This application claims the benefit of U.S. provisional application 61/818,121 filed May 1, 2013, which is herein incorporated by reference.

The attached sequence listing is hereby incorporated by reference.

FIELD OF THE INVENTION

The present invention relates to the provision of antibodies with long HCDR3 lengths. The present invention is also directed to the provision of novel V, D and J pairings in immunoglobulin heavy and light chain loci. Novel, biased antibody diversities and potentially expanded diversities are provided. The invention also provides for novel and potentially expanded diversity or diversity that is biased towards variable gene usage common to antibodies useful for treating and/or preventing certain diseases or conditions, such as infectious diseases. This ability to bias the antibody repertoire also provides methods of simplifying the production of antibody mixtures, such as polyclonal antibody therapeutics useful for the treatment and/or prevention of infectious diseases where a polyclonal approach to target multiple pathogen antigens is desirable. To this end, the present invention also provides bispecific antibodies that are capable of binding to more than one antigen (eg, multiple infectious antigens expressed by the same pathogen), thus providing advantages (such as manufacturing, dosing and administration advantages) not possible with polyclonal antibody mixtures.

The present invention provides vertebrates and cells, such as transgenic mice or rats or transgenic mouse or rat cells. Furthermore, the invention relates to methods of using the vertebrates to isolate antibodies or nucleotide sequences encoding antibodies. Antibodies, nucleotide sequences, pharmaceutical compositions and uses are also provided by the invention.

BACKGROUND

The state of the art provides non-human vertebrates (eg, mice and rats) and cells comprising transgenic immunoglobulin loci, such loci comprising human variable (V), diversity (D) and/or joining (J) segments, and optionally human constant regions. Alternatively, endogenous constant regions of the host vertebrate (eg, mouse or rat constant regions) are provided in the transgenic loci. Methods of constructing such transgenic vertebrates and use of these to generate antibodies and nucleic acids thereof following antigen immunisation are known in the art, eg, see U.S. Pat. No. 7,501,552 (Medarex), U.S. Pat. No. 5,939,598 (Abgenix), U.S. Pat. No. 6,130,364 (Abgenix), WO02/066630 (Regeneron), WO2011004192 (Genome Research Limited), WO2009076464, WO2009143472 and WO2010039900 (Ablexis), the disclosures of which are explicitly incorporated herein. Such transgenic loci in the art include varying amounts of the human V(D)J repertoire.

Existing transgenic immunoglobulin loci tend to be based on a single human DNA source. The potential diversity of human antibody variable regions in non-human vertebrates bearing such transgenic loci is thus confined by the repertoire used.

It would be desirable to provide for novel and potentially expanded repertoire and diversity of human variable regions in transgenic immunoglobulin loci and non-human vertebrates harbouring these, as well as in antibodies produced following immunisation of such animals.

SUMMARY OF THE INVENTION

The present inventors have discovered, by way of construction of transgenic non-human vertebrates, immunisation, antibody heavy chain collection and deep bioinformatics analysis, how to rationally design for VH domains, heavy chains and antibodies having long HCDR3s. These are useful for addressing antigens (such as infectious disease pathogen antigens, receptors and enzyme clefts) where a longer CDR better addresses the target.

The present inventors also realised the possibility of providing combinations of V, D and J gene segments in new ways to provide synthetic gene segment combinations in immunoglobulin loci that are not found in nature or in state-of-the-art loci. The inventors realised the importance of this to provide for novel and potentially expanded repertoire and diversity of human variable regions in transgenic immunoglobulin loci and non-human vertebrates harbouring these, as well as in antibodies produced following immunisation of such animals. In one aspect, the inventors realised that it would be desirable to bias the novel repertoire for the production of antibodies having improved affinity and/or biophysical characteristics, and/or wherein the range of epitope specificities produced by means of such repertoire is novel, provides for antibodies to epitopes that have hitherto been intractable by prior transgenic immunoglobulin loci or difficult to address. For example, the inventors envisaged a specific application to bias the novel repertoire for the production of antibodies useful in the therapy and/or prevention of infectious disease.

To this end, in a first configuration of the invention, there is provided

A non-human vertebrate (optionally a mouse or a rat) or vertebrate cell whose genome comprises:

(a) An immunoglobulin heavy chain locus comprising one or more human V gene segments, one or more human D gene segments and one or more human J gene segments upstream of a constant region; optionally wherein the heavy chain locus is according to any configuration of the invention described below; and (b) An immunoglobulin light chain locus comprising either (i) one or more human VH gene segments and one or more human J gene segments upstream of a constant region (optionally a rearranged VHJLCL or VHJλCL, wherein the CL is Cλ or Cκ); or (ii) one or more human VL gene segments, one or more human D gene segments and one or more human JH gene segments upstream of a constant region (optionally a rearranged VLDJHCL or VλDJHCL, wherein the CL is Cλ or Cκ); or (iii) one or more human VL gene segments selected from the group consisting of: a VλII gene family member, VλVII 4A, VλII 2.1, VλVII 4A, a Vλ1 gene family member, a Vλ3gene family member, IGLV1S2, Vλ3-cML70, lalh2, lalyvl, la3h3, Kv325, a VκI gene family member, κI-15A (KL012), VκII family member, a VκI family member, a VκI gene family member, κI-15A (KL012), VκII A2 (optionally the A2a allele), Vκ A27 (Humkv325) and a gene segment at least 80% identical thereto, and one or more human JL gene segments upstream of a constant region;

Wherein the gene segments in the heavy chain locus are operably linked to the constant region thereof, and the gene segments in the light chain locus are operably linked to the constant region thereof, so that upon immunisation the mouse is capable of producing an antibody comprising heavy chains produced by recombination of the heavy chain locus and light chains produced by recombination of the light chain locus.

In one aspect, in (b)(i) the V gene segment repertoire of the light chain locus comprises or consists of one or more VH gene segments selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto; or in (b)(iii) the light chain locus V gene segment repertoire consists of one VL gene segment type (optionally and one or mutants thereof), wherein the VL gene segment is selected from said group of VL gene segments.

In a second configuration of the present invention, there is provided

A non-human vertebrate (optionally a mouse or a rat) or vertebrate cell whose genome comprises:

(a) An immunoglobulin heavy chain locus comprising one or more human V gene segments, one or more human D gene segments and one or more human J gene segments upstream of a constant region; and (b) (i) An unrearranged immunoglobulin light chain locus comprising one or more human VH gene segments and one or more human J gene segments upstream of a constant region, wherein each human VH gene segment is a human gene segment identical to (or mutant of) a human VH gene segment used to produce a rearranged VDJ encoding a heavy chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism); or (ii) An immunoglobulin light chain locus comprising a rearranged VDJ region or VDJ region upstream of a constant region, wherein the nucleotide sequence of the recombined region is identical to a nucleotide sequence produced by the recombination of a human 1 gene segment and optionally a human D gene segment with a human VH gene segment that is identical to (or mutant of) the human VH gene segment used to produce a rearranged VDJ encoding a heavy chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism);

(c) Wherein the gene segments in the heavy chain locus are operably linked to the constant region thereof, and the gene segments or VJ or VDJ in the light chain locus are operably linked to the constant region thereof, so that upon immunisation the mouse is capable of producing an antibody comprising heavy chains produced by recombination of the heavy chain locus and light chains derived from the light chain locus;

(d) Optionally when (b)(i) applies, each said VH gene segment in the light chain locus is selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto;

(e) Optionally when (b)(ii) applies, the nucleotide sequence of the recombined region is identical to a nucleotide sequence produced by the recombination of a human J gene segment and optionally a human D gene segment with a human VH gene segment selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto.

In one aspect, the V gene segment repertoire of the light chain locus comprises or consists of one human VH gene segment; optionally germline VH and one or more polymorphic variants thereof, eg, where each polymorphic variant differs from the germline VH nucleotide sequence by 1, 2, 3, 4, 5, 6, 7, 8, 9 or 10 positions. In one aspect, the V gene segment repertoire of the light chain locus comprises or consists of human VH1-69 gene segment; optionally germline VH1-69 and one or more polymorphic variants thereof, eg, where each polymorphic variant differs from the germline VH1-69 nucleotide sequence by 1, 2, 3, 4, 5, 6, 7, 8, 9 or 10 positions. An example of constructing an immunoglobulin locus comprising VH1-69 and polymorphic variants is given below. By using a particular gene segment (eg, one commonly found inhuman antibodies raised in humans against an infection or other condition) and one or more polymorphic variants thereof, it is possible to provide a repertoire of genes and yet still bias the antibody gene repertoire to a gene segment that is relevant to the disease (eg, an infectious disease, such as a bacterial or viral disease, eg, influenza). This provides a useful pool of genes from which to ultimately generate and isolate a lead antibody for a therapeutic/prophylactic against the disease in question. In an example, the polymorphic variants are natural variants seen in human beings or human populations. The skilled person will know of sources of human antibody gene sequences, such as IMGT (www.imgt.org), GenBank (www.ncbi.nlm.nih.gov/genbank) and the 1000 Genomes databases (www.1000genomes.org). Bioinformatics tools for database manipulation are also readily available and known to the skilled person, eg, as publicly available from the 1000 Genomes Project/EBI (www.1000genomes.org)

In another aspect, the genome of said vertebrate or cell is homozygous for light chain locus (b)(i) or (ii); optionally wherein:

the V gene segment repertoire of the light chain loci consists of one or more human VH gene segments selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto; or the recombined VJ or VDJ repertoire of the light chain loci consists of sequences identical to one or more nucleotide sequences produced by the recombination of a human VH gene segment selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto, with a human J gene segment and optionally a human D gene segment.

In another aspect, each immunoglobulin light chain locus of said vertebrate or cell is according to (b)(i) and comprises only a single human VH gene segment selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1110, VH4.11, 71-4, VH251, VH1-69 and a gene segment at least 80% identical thereto, optionally wherein the genome of the vertebrate or cell is homozygous for said light chain so that all light chain loci comprise the same, single human VH gene segment.

The invention provides a first method of isolating an antibody that binds a predetermined antigen, the method comprising
(a) providing a vertebrate (optionally a mouse or rat) according to any preceding configuration or aspect;
(b) immunising said vertebrate with said antigen (optionally wherein the antigen is an antigen of an infectious disease pathogen);
(c) removing B lymphocytes from the vertebrate and selecting one or more B lymphocytes expressing antibodies that bind to the antigen;
(d) optionally immortalising said selected B lymphocytes or progeny thereof, optionally by producing hybridomas therefrom; and
(e) isolating an antibody (eg, and IgG-type antibody) expressed by the B lymphocytes.

A second method is provided comprising carrying out the first method and the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

An aspect provides method of producing a polyclonal antibody mixture, the method comprising carrying out the first method by separately immunising first and second vertebrates (optionally first and second mice or first and second rats) with antigen and combining the anti-antigen antibodies isolated from each vertebrate (or mutants or derivatives of said antibodies) to produce a polyclonal antibody mixture; optionally wherein the following apply separately or in combination ((i) and (ii); or (i) and (iii)):
(i) the vertebrates are immunised with the same antigen or different antigens (optionally wherein the different antigens are expressed by the same pathogenic organism (or a family member thereof));
(ii) prior to immunisation the light chain loci of the vertebrates contain the identical VH gene repertoire (optionally a single VH gene) and optionally the identical 1 repertoire; optionally the light chain loci of the mammals are identical prior to immunisation;
(iii) prior to immunisation the light chain loci of the vertebrates contain the identical rearranged VJ or VDJ repertoire (optionally a single VJ or VDJ); optionally the light chain loci of the vertebrates are identical prior to immunisation.

An aspect provides method of producing a polyclonal antibody mixture, the method comprising carrying out the first method by immunising one or a plurality of vertebrates (optionally mice or rats) with first and second antigens and combining the anti-antigen antibodies isolated from each vertebrate (or mutants or derivatives of said antibodies) to produce a polyclonal antibody mixture; optionally wherein the following apply separately or in combination ((i) and (ii); or (i) and (iii)):
(i) the antigens are expressed by the same pathogenic organism (or a family member thereof));
(ii) prior to immunisation the light chain loci of the vertebrates contain the identical VH gene repertoire (optionally a single VH gene) and optionally the identical J repertoire; optionally the light chain loci of the mammals are identical prior to immunisation;
(iii) prior to immunisation the light chain loci of the vertebrates contain the identical rearranged VJ or VDJ repertoire (optionally a single VJ or VDJ); optionally the light chain loci of the vertebrates are identical prior to immunisation.

An aspect provides method of producing host cells capable of expressing a polyclonal antibody mixture, the method comprising, in the second method:—
(a) immunising one or a plurality of vertebrates (optionally mice or rats) with first and second antigens (optionally wherein the different antigens are expressed by the same pathogenic organism (or a family member thereof));
(b) isolating nucleic acid encoding first and second anti-antigen antibodies from B lymphocytes from said vertebrates;
(c) determining the nucleotide sequences of the heavy and light chain variable regions of the first antibody;
(d) determining the nucleotide sequence of the heavy variable region and optionally the light chain variable region of the second antibody;
(e) inserting the heavy chain variable region coding sequence of each antibody into a heavy chain expression vector; optionally wherein the constant region coding sequence of each heavy chain is exchanged for a nucleotide sequence that encodes a human or humanised constant region;
(f) inserting the light chain variable region coding sequence of the first antibody into a light chain expression vector; optionally wherein the constant region coding sequence of the light chain of the first antibody is exchanged for a nucleotide sequence that encodes a human or humanised constant region;
(g) optionally inserting the light chain variable region coding sequence of the second antibody into a light chain expression vector; optionally wherein the constant region coding sequence of the light chain of the second antibody is exchanged for a nucleotide sequence that encodes a human or humanised constant region; and
(h) introducing each expression vector into a host cell and co-expressing antibody chains in a mixture of said host cells to produce antibodies, each antibody comprising one or both of said heavy chain variable regions and a light chain; optionally wherein the expression vectors are introduced together into the same host cell (eg, a CHO or HEK293 cell) so that the cell is capable of expressing antibody light chains and heavy chains, such that the cell or a plurality of the host cells express antibodies, each comprising one or both of said heavy chain variable regions and a light chain;
(i) optionally:
prior to immunisation the light chain loci of the vertebrates contain the identical VH gene repertoire (optionally a single VH gene segment) and optionally the identical J repertoire (optionally a single J gene segment); optionally the light chain loci of the vertebrates are identical prior to immunisation; or
prior to immunisation the light chain loci of the vertebrates contain the identical rearranged VJ or VDJ repertoire (optionally a single VJ or VDJ); optionally the light chain loci of the vertebrates are identical prior to immunisation.

The invention also provides a method of producing a monoclonal or polyclonal antibody mixture, optionally for use in medicine, optionally for the treatment and/or prevention of an infectious disease, wherein optionally wherein each antibody binds an antigen of an infectious disease pathogen, preferably the same antigen. The invention also provides the use of an isolated, monoclonal or polyclonal antibody, or a mutant or derivative antibody thereof in the manufacture of a medicament for the treatment and/or prevention of an infectious disease, optionally wherein the infectious disease is a disease caused by a bacterial or viral pathogen.

The invention further provides an isolated antibody (eg, IgG-type antibody) obtainable or obtained by a method of the invention, or a mutant or derivative antibody thereof wherein (i) the isolated antibody comprises two copies of the heavy chain variable region of said first antibody paired with two copies of the light chain variable region of said first antibody; or (ii) the isolated antibody comprises two copies of the heavy chain variable region of said second antibody paired with two copies of the light chain variable region of said first antibody; or (iii) the isolated antibody is a bispecific antibody comprising one copy of the heavy chain variable region of said first antibody paired with a copy of the light chain variable region of the first antibody, and one copy of the heavy chain variable region of said the antibody paired with a copy of the light chain variable region of the first antibody, optionally wherein the bispecific antibody binds to said first and second antigens are expressed by the same pathogenic organism (or a family member thereof; optionally for use in medicine, optionally for the treatment and/or prevention of an infectious disease.

In an aspect, there is provided a nucleotide sequence encoding an antibody of the invention, optionally wherein the nucleotide sequence is part of a vector.

In an aspect, there is provided a pharmaceutical composition comprising the antibody or antibodies of the invention and a diluent, excipient or carrier.

In a third configuration of the invention, there is provided
A non-human vertebrate (optionally a mouse or a rat) or vertebrate cell whose genome comprises:
(a) An immunoglobulin heavy chain locus comprising either:—
(i) one or more human VL gene segments, one or more human D gene segments and one or more human J gene segments upstream of a constant region (optionally a rearranged VLDJHCH or VλDJHCH); or
(ii) one or more human VH gene segments selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical; one or more human D gene segments and one or more human JH gene segments upstream of a constant region; and
(b) An immunoglobulin light chain locus comprising one or more human V gene segments and one or more human J gene segments upstream of a constant region, optionally wherein the light chain locus is according to (b)(i) or (b)(ii) of the first configuration of the invention;

Wherein the gene segments in the heavy chain locus are operably linked to the constant region thereof, and the gene segments in the light chain locus are operably linked to the constant region thereof, so that upon immunisation the mouse is capable of producing an antibody comprising heavy chains produced by recombination of the heavy chain locus and light chains produced by recombination of the light chain locus.

In a fourth configuration of the invention, there is provided
A non-human vertebrate (optionally a mouse or a rat) or vertebrate cell whose genome comprises:
(a) (i) An unrearranged immunoglobulin heavy chain locus comprising one or more human VL gene segments, one or more human D gene segments and one or more JH gene segments upstream of a constant region, wherein each human VL gene segment is a human gene segment identical to (or mutant of) a human VL gene segment used to produce a rearranged VJ encoding a light chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism); or
(ii) An immunoglobulin heavy chain locus comprising a rearranged VJ region or VDJ region upstream of a constant region, wherein the nucleotide sequence of the recombined region is identical to a nucleotide sequence produced by the recombination of a human J gene segment and optionally a human D gene segment with a human VL gene segment that is identical to (or mutant of) the human VL gene segment used to produce a rearranged VJ encoding a light chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism);
(b) An immunoglobulin light chain locus comprising one or more human V gene segments and one or more human J gene segments upstream of a constant region; and
(c) Wherein the gene segments in the light chain locus are operably linked to the constant region thereof, and the gene segments or VJ or VDJ in the heavy chain locus are operably linked to the constant region thereof, so that upon immunisation the mouse is capable of producing an antibody comprising light chains produced by recombination of the light chain locus and heavy chains derived from the heavy chain locus;
(d) Optionally when (a)(i) applies, each said VL gene segment in the heavy chain locus is selected from the group consisting of a VL gene segment selected from the group consisting of a VλII gene family member, VλVII 4A, VλII 2.1, VλVII 4A, a Vλ1 gene family member, a Vλ3gene family member, IGLV1S2, Vλ3-cML70, lalh2, lalvl, la3h3, Kv325, a VκI gene family member, κI-15A (KL012), VκII family member, a VκIII family member, a VκI gene family member, κI-15A (KL012), VκII A2 (optionally the A2a allele), Vκ A27 (Humkv325) and a gene segment at least 80% identical thereto;

(e) Optionally when (a)(ii) applies, the nucleotide sequence of the recombined region is identical to a nucleotide sequence produced by the recombination of a human J gene segment and optionally a human D gene segment with a human VL gene segment selected from the group consisting of a VL gene segment selected from the group consisting of a MI gene family member, VλVII 4A, VλII 2.1, VλVII 4A, a Vλ1 gene family member, a Vλ3gene family member, IGLV1S2, Vλ3-cML70, lalh2, lalvl, la3h3, Kv325, a VκI gene family member, κI-15A (KL012), VκII family member, a VκIII family member, a VκI gene family member, κI-15A (KL012), VκII A2 (optionally the A2a allele), Vκ A27 (Humkv325) and a gene segment at least 80% identical thereto.

In one aspect of the fourth configuration of the invention, the genome of said vertebrate or cell is homozygous for heavy chain locus (a)(i) or (ii); optionally wherein:

the V gene segment repertoire of the heavy chain loci consists of one or more human VL gene segments selected from the group consisting of a VL gene segment selected from the group consisting of a VλII gene family member, VλVII 4A, VλII 2.1, VλVII 4A, a Vλ1 gene family member, a Vλ3gene family member, IGLV1S2, Vλ3-cML70, lalh2, lalyvl, la3h3, Kv325, a VκI gene family member, κI-15A (KL012), VκII family member, a VκIII family member, a VκI gene family member, κI-15A (KL012), VκII A2 (optionally the A2a allele), Vκ A27 (Humkv325) and a gene segment at least 80% identical thereto; or the recombined VJ or VDJ repertoire of the heavy chain loci consists of sequences identical to one or more nucleotide sequences produced by the recombination of a human VL gene segment selected from the group consisting of a VL gene segment selected from the group consisting of a VλII gene family member, VλVII 4A, VλII 2.1, VλVII 4A, a Vλ1 gene family member, a Vλ3gene family member, IGLV1S2, Vλ3-cML70, lalh2, lalyvl, la3h3, Kv325, a VκI gene family member, κI-15A (KL012), VκII family member, a VκIII family member, a VκI gene family member, Id-15A (KL012), VκII A2 (optionally the A2a allele), VκA27 (Humkv325) and a gene segment at least 80% identical thereto with a human J gene segment and optionally a human D gene segment.

The invention provides a monoclonal or polyclonal antibody composition prepared by immunisation of at least one vertebrate (eg, mouse or rat) according to any preceding configuration or aspect with an antigen, optionally wherein the antigen is an antigen of an infectious disease pathogen, optionally wherein the same antigen is used to immunise all the vertebrates; optionally wherein the antibody or antibodies are IgG-type.

The invention also provides an isolated chimaeric antibody for treating and/or preventing an infectious disease or condition, the antibody comprising a non-human vertebrate (optionally a mouse or rat) heavy chain constant regions and human variable regions that bind an antigen of an infectious disease pathogen, wherein the antibody is obtainable or obtained in a method comprising immunisation of a non-human vertebrate of the invention with said antigen.

The invention also provides an isolated human antibody for treating and/or preventing an infectious disease or condition, the antibody comprising human heavy chain constant regions and human variable regions that bind an antigen of an infectious disease pathogen, wherein the antibody is obtainable or obtained in a method comprising affinity maturation of antibody variable regions in vivo in a transgenic non-human vertebrate (eg, mouse or rat) when said variable regions are operably linked to heavy chain constant regions of said vertebrate (eg, mouse or rat heavy chain constant regions) by (a) immunisation of a vertebrate of the invention with said antigen, (b) isolation of nucleic acid encoding a chimaeric antibody according to the invention, (c) replacing the nucleotide sequences of the nucleic acid that encode the non-human vertebrate heavy chain constant regions with nucleotide sequence encoding human heavy chain constant regions to produce nucleic acid encoding a human antibody; (d) expressing the human antibody in vitro (optionally from CHO or HEK293 cells harbouring the human nucleic acid) and (e) isolating the human antibody (optionally with further affinity maturation of the antibody and/or producing a derivative thereof).

An aspect provides a mixture of first and second human antibodies, each antibody being capable of binding to an antigen of an infectious disease pathogen (optionally wherein the first antibody binds a first antigen and the second antibody binds a second antigen, said antigens being from the same pathogen; or wherein the antigens are the same). In an embodiment, a common light chain is used which enables simplified manufacture of the antibody mixture. Thus, there is provided in the mixture, the light chain amino acid sequence of the first antibody that is identical to the light chain amino acid sequence of the second antibody, or has up to 15 amino acid changes therefrom.

The invention further provides a host cell comprising one or more expression vectors encoding 3 or more first and second antibody heavy and light chains.

In a fifth configuration of the invention, there is provided

A synthetic immunoglobulin locus comprising one or more variable and 0.1 gene segments (and optionally one or more D gene segments) operably linked 5' of a constant region, wherein the locus comprises a 5' to 3' V(D)J arrangement selected from the group consisting of immunoglobulin locus can be constructed with one or more of the following arrangements (5' to 3'):—

(a) [V (heavy, lambda or kappa)]-[two-turn RSS]-[one-turn RSS]-[D]-[JH], wherein said RSSs are in an opposite orientation;
(b) [VH]-[D]-[two-turn RSS]-[one-turn RSS]-[J lambda], wherein said RSSs are in an opposite orientation;
(c) [VH]-[D]-[one-turn RSS]-[two-turn RSS]-[J kappa], wherein said RSSs are in an opposite orientation;
(d) [VH or V kappa]-[two-turn RSS]-[one-turn RSS]-[J lambda], wherein said RSSs are in an opposite orientation;
(e) [V kappa]-[one-turn RSS]-[two-turn RSS]-[JH or J lambda], wherein said RSSs are in an opposite orientation;
(f) [V (heavy, lambda or kappa)]-[one-turn RSS]-[two-turn RSS]-[D]-[JH], wherein said RSSs are in an opposite orientation;
(g) [VH]-[D]-[one-turn RSS]-[two-turn RSS]-[J lambda], wherein said RSSs are in an opposite orientation;
(h) [VH]-[D]-[two-turn RSS]-[one-turn RSS]-[J kappa], wherein said RSSs are in an opposite orientation;

(i) [VH or V kappa]-[one-turn RSS]-[two-turn RSS]-[J lambda], wherein said RSSs are in an opposite orientation;

(j) [V kappa]-[two-turn RSS]-[one-turn RSS]-[JH or J lambda], wherein said RSSs are in an opposite orientation.

In a sixth configuration, the invention also provides means for generating VH domains, heavy chains and antibodies having a long HCDR3 length. In this context, the invention provides:—

A non-human vertebrate (eg, a mouse or a rat) or a non-human vertebrate cell (eg, a mouse cell or a rat cell) whose genome comprises a human immunoglobulin D gene segment repertoire that is biased to the human D2 and/or D3 family or biased to one, more or all human D gene segments selected from the group D1-26, D2-2, D3-9, D3-10, D3-22, D4-17, D6-13 and D6-19.

A non-human vertebrate (eg, a mouse or a rat) or a non-human vertebrate cell (eg, a mouse cell or a rat cell), optionally according to any preceding claim, whose genome comprises a human immunoglobulin VH gene segment repertoire that is biased to one, more or all of gene segments selected from the group VH1-2, VH1-3, VH1-8, VH1-18, VH5-51, VH1-69, VH2-5, VH3-7, VH3-9, VH3-11, VH3-13, VH3-20, VH3-21, VH3-23, VH4-4, VH6-1 and VH7-4-1.

A non-human vertebrate (eg, a mouse or a rat) or a non-human vertebrate cell (eg, a mouse cell or a rat cell) whose genome comprises a human immunoglobulin JH gene segment repertoire that is biased to human JH6.

A monoclonal or polyclonal antibody composition or a population of antibody-producing cells for producing such composition, wherein the composition or population is prepared by immunising at least one vertebrate according to any preceding claim with an antigen, wherein the antibody or antibodies have human heavy chain variable regions comprising non-human vertebrate AID-pattern somatic hypermutations, (eg, mouse or rat AID-pattern mutations) when compared to corresponding human germline V, D and J sequences and/or non-human (eg, mouse or rat) terminal deoxynucleotidyl transferase (TdT)-pattern junctional mutations when compared to corresponding human germline V, D and J sequences; wherein the composition comprises at least one antigen-specific antibody having a HCDR3 length of at least 20 amino acids (according to IMGT).

A repertoire of antibody heavy chains (eg, provided by antibodies) comprising one or more heavy chains whose variable domain HCDR3 has a length of at least 20 amino acids (according to IMGT) and derived from the recombination of a human VH, D and JH, wherein
the VH is selected from the group
VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01 and
the D is selected from the group
D2-2*02, D3-9*01, D3-10*01 and D3-22*01, or
D2-2*02, D3-9*01 and D3-10*01, or
D3-9*01 and D3-10*01, or
D1-26, D2-2, D3-9, D3-10, D3-22, D4-17, D6-13 and D6-19, or
D1-26*01, D2-2*02, D3-9*01, D3-10*01, D3-22*01, D4-17*01, D6-13*01 and D6-19*01, or
D2-2, D3-9, D3-10, D3-22, D4-17, D6-13 and D6-19, or
D2-2*02, D3-9*01, D3-10*01, D3-22*01, D4-17*01, D6-13*01 and D6-19*01, or
D1-26, D2-2, D3-10 and 06-19, or
D2-2, D3-9 and D3-10;
and optionally the JH is JH6 (eg, JH6*02);
Wherein
(a) the heavy chain variable domain has been produced in vivo in a non-human vertebrate (eg, a mouse or a rat); and/or
(b) the heavy chain variable domain comprises non-human vertebrate AID-pattern somatic hypermutations, (eg, mouse or rat AID-pattern mutations) when compared to corresponding human germline V, D and J sequences and/or non-human (eg, mouse or rat) terminal deoxynucleotidyl transferase (TdT)-pattern junctional mutations when compared to corresponding human germline V, D and J sequences.

BRIEF DESCRIPTION OF THE FIGURES

FIGS. 5A-5D: Alignment of 13 IGHV1-69 alleles showing the variable (V) coding region only. Nucleotides that differ from VH1-69 allele *01 are indicated at the appropriate position whereas identical nucleotides are marked with a dash. Where nucleotide changes result in amino acid differences, the encoded amino acid is shown above the corresponding triplet. Boxed regions correspond to CDR1, CDR2 and CDR3 as indicated.

SEQ ID NO:28 and SEQ ID NO:27 denote the amino acid sequence and nucleic acid sequence, respectively, displayed for L22582, IGHV1-69*01, hv1051.

SEQ ID NO:41 and SEQ ID NO:29 denote the amino acid sequence and nucleic acid sequence, respectively, displayed for Z27506, IGHV1-69*02, yIGH6(YAC7).

SEQ ID NO:42 and SEQ ID NO:30 denote the amino acid sequence and nucleic acid sequence, respectively, displayed for X92340, IGHV1-69*03, 57GTA8.

SEQ ID NO:43 and SEQ ID NO:31 denote the amino acid sequence and nucleic acid sequence, respectively, displayed for M83132, IGHV1-69*04, hv1263.

SEQ ID NO:44 and SEQ ID NO:32 denote the amino acid sequence and nucleic acid sequence, respectively, displayed for K67905, IGHV1-69*05, RR.VH1.2.

SEQ ID NO:45 and SEQ ID NO:33 denote the amino acid sequence and nucleic acid sequence, respectively, displayed for L22583, IGHV1-69*06, hv1051K.

SEQ ID NO:46 and SEQ ID NO:34 denote the amino acid sequence and nucleic acid sequence, respectively, displayed for Z29978, IGHV1-69*07, DA-2.

SEQ ID NO:47 and SEQ ID NO:35 denote the amino acid sequence and nucleic acid sequence, respectively, displayed for Z14309, IGHV1-69*08.

SEQ ID NO:48 and SEQ ID NO:36 denote the amino acid sequence and nucleic acid sequence, respectively, displayed for Z14307, IGHV1-69*09.

SEQ ID NO:49 and SEQ ID NO:37 denote the amino acid sequence and nucleic acid sequence, respectively, displayed for Z14300, IGHV1-69*10.

SEQ ID NO:50 and SEQ ID NO:38 denote the amino acid sequence and nucleic acid sequence, respectively, displayed for Z14296, IGHV1-69*11.

SEQ ID NO:39 denotes the nucleic acid sequence displayed for Z14301, IGHV1-69*12.

SEQ ID NO:40 denotes the nucleic acid sequence displayed for Z14214, IGHV1-69*13.

Figure 6:
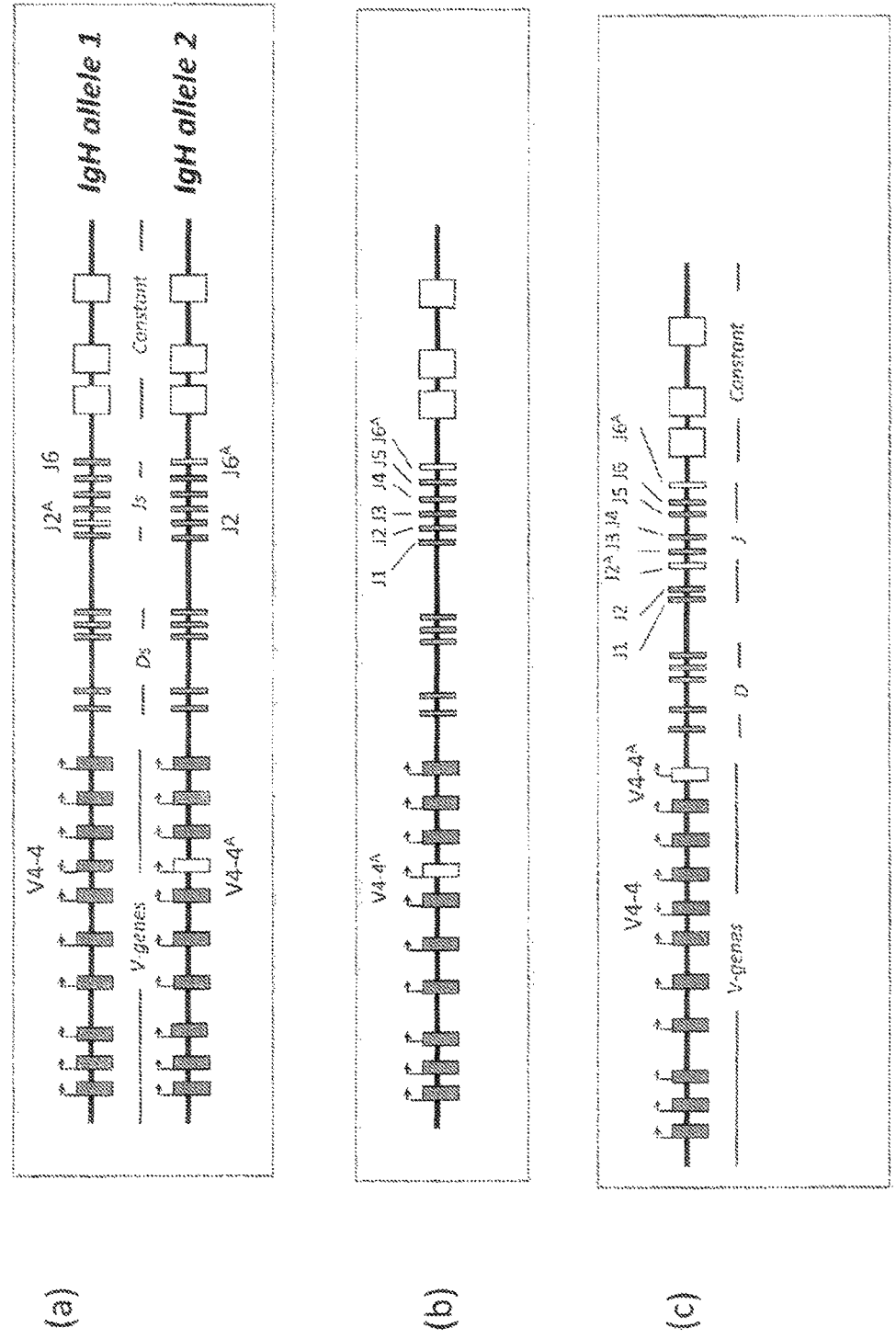

FIG. 6: RSS structure and recombination schematic.

DETAILED DESCRIPTION OF THE INVENTION

A source for human V, D and J gene segments is Bacterial Artificial Chromosomes (RPCI-11 BACs) obtained from Roswell Park Cancer Institute (RPCI)/Invitrogen. See //bacpac.chori.org/hmale11.htm, which describes the BACs as follows: —

"RPCI-11 Human Male BAC Library

The RPCI-11 Human Male BAC Library (Osoegawa et al., 2001) was constructed using improved cloning techniques (Osoegawa et al., 1998) developed by Kazutoyo Osoegawa. The library was generated by Kazutoyo Osoegawa. Construction was funded by a grant from the National Human Genome Research Institute (NHGRI, NIH) (#1R01RG01165-03). This library was generated according to the new NHGR1/DOE "Guidance on Human Subjects in Large-Scale DNA Sequencing . . . .

"Male blood was obtained via a double-blind selection protocol. Male blood DNA was isolated from one randomly chosen donor (out of 10 male donors)".

Osoegawa K, Mammoser A G, Wu C, Frengen E, Zeng C, Catanese J J, de Jong P J; Genome Res. 2001 March; 11(3):483-96; "A bacterial artificial chromosome library for sequencing the complete human genome";

Osoegawa, K., Woon, P. Y., Zhao, B., Frengen, E., Tateno, M., Catanese, J J, and de Jong, P. J. (1998); "An Improved Approach for Construction of Bacterial Artificial Chromosome Libraries"; Genomics 52, 1-8.

As a source of antibody gene segment sequences, the skilled person will also be aware of the following available databases and resources (including updates thereof):—

1.1. The Kabat Database (G. Johnson and T. T. Wu, 2002; http://www.kabatdatabase.com). Created by E. A. Kabat and T. T. Wu in 1966, the Kabat database publishes aligned sequences of antibodies, T-cell receptors, major histocompatibility complex (MHC) class I and II molecules, and other proteins of immunological interest. A searchable interface is provided by the SeqhuntII tool, and a range of utilities is available for sequence alignment, sequence subgroup classification, and the generation of variability plots. See also Kabat, E. A., Wu, T. T., Perry, H., Gottesman, K., and Foeller, C. (1991) *Sequences of Proteins of Immunological Interest,* 5th ed., NIH Publication No. 91-3242, Bethesda, Md., which is incorporated herein by reference, in particular with reference to human gene segments for use in the present invention.

1.2. KabatMan (A. C. R. Martin, 2002; http://www.bioinf.org.uk/abs/simkab.html). This is a web interface to make simple queries to the Kabat sequence database.

1.3. IMGT, the International ImMunoGeneTics Information System®; M.-P. Lefranc, 2002; online at imgt.cines.fr. IMGT is an integrated information system that specializes in antibodies, T cell receptors, and MHC molecules of all vertebrate species. It provides a common portal to standardized data that include nucleotide and protein sequences, oligonucleotide primers, gene maps, genetic 5 polymorphisms, specificities, and two-dimensional (2D) and three-dimensional (3D) structures. IMGT includes three sequence databases (IMGT/LIGM-DB, IMGT/MHC-DB, IMGT/PRIMERDB), one genome database (IMGT/GENE-DB), one 3D structure database (IMGT/3Dstructure-DB), and a range of web resources ("IMGT Marie-Paule page") and interactive tools.

1.4 V-BASE (I. M. Tomlinson, 2002; online at mrc.cpe.cam.ac.uk/base. V-BASE is a comprehensive directory of all human antibody germline variable region sequences compiled from more than one thousand published sequences. It includes a version of the alignment software DNAPLOT (developed by Hans-Helmar Althaus and Werner Muller) that allows the assignment of rearranged antibody V genes to their closest germline gene segments.

1.5. Antibodies—Structure and Sequence (A. C. R. Martin, 2002; online at bioinforg.uk/abs. This page summarizes useful information on antibody structure and sequence. It provides a query interface to the Kabat antibody sequence data, general information on antibodies, crystal structures, and links to other antibody-related information. It also distributes an automated summary of all antibody structures deposited in the Protein Databank (PDB). Of particular interest is a thorough description and comparison of the various numbering schemes for antibody variable regions.

1.6. AAAAA-AHo's Amazing Atlas of Antibody Anatomy (A. Honegger, 2001; online at unizh.ch/-antibody. This resource includes tools for structural analysis, modeling, and engineering. It adopts a unifying scheme for comprehensive structural alignment of antibody and T-cell-receptor sequences, and includes Excel macros for antibody analysis and graphical representation.

1.7. WAM—Web Antibody Modeling (N. Whitelegg and A. R. Rees, 2001; online at antibody.bath.ac.uk. Hosted by the Centre for Protein Analysis and Design at the University of Bath, United Kingdom. Based on the AbM package (formerly marketed by Oxford Molecular) to construct 3D models of antibody Fv sequences using a combination of established theoretical methods, this site also includes the latest antibody structural information.

1.8. Mike's Immunoglobulin Structure/Function Page (M. R. Clark, 2001; http://www.path.cam.ac.uk/~mrc7/mikeimages.html) These pages provide educational materials on immunoglobulin structure and function, and are illustrated by many colour images, models, and animations. Additional information is available on antibody humanization and Mike Clark's Therapeutic Antibody Human Homology Project, which aims to correlate clinical efficacy and anti-immunoglobulin responses with variable region sequences of therapeutic antibodies.

1.9. The Antibody Resource Page (The Antibody Resource Page, 2000; http://www.antibodyresource.com). This site describes itself as the "complete guide to antibody research and suppliers." Links to amino acid sequencing tools, nucleotide antibody sequencing tools, and hybridoma/cell-culture databases are provided.

1.9. Humanization bY Design (J. Saldanha, 2000; http://people.cryst.bbk.ac.uk/~ubcq07s). This resource provides an overview on antibody humanization technology. The most useful feature is a searchable database (by sequence and text) of more than 40 published humanized antibodies including information on design issues, framework choice, framework back-mutations, and binding affinity of the humanized constructs.

See also Antibody Engineering Methods and Protocols, Ed. Benny K C Lo, Methods in Molecular Biology™, Human Press. Also at http://www.blogsua.com/pdf/antibody-engineering-methods-and-protocolsantibody-engineering-methods-and-protocols.pdf In one embodiment throughout the present text, "germline" refers to the canonical germline gene segment sequence.

The present invention is directed to the provision of novel V, D and J pairings in immunoglobulin heavy and light chain loci. Novel, biased antibody diversities and potentially expanded diversities are provided. One aspect of the invention exploits the natural pairing of compatible recombination signal sequences (RSSs) during antibody V(D)J recombination in vivo, and this aspect of the invention provides new, synthetic combinations of V, D and J gene segments using the observation of RSS compatibility.

Another aspect of the invention is based on the observation of V, D and J usage bias in naturally-occurring human antibodies raised against infectious disease pathogens. The invention is useful for manipulating the antibody gene diversity in transgenic non-human animals, thus providing for novel and potentially expanded diversity or diversity that is biased towards variable gene usage common to antibodies useful for treating and/or preventing certain diseases or conditions, such as infectious diseases. This ability to bias the antibody repertoire also provides methods of simplifying the production of antibody mixtures, such as polyclonal antibody therapeutics useful for the treatment and/or prevention of infectious diseases where a polyclonal approach to target multiple pathogen antigens is desirable. To this end, the present invention also provides bispecific antibodies that are capable of binding to more than one antigen (eg, multiple infectious antigens expressed by the same pathogen), thus providing advantages (such as manufacturing, dosing and administration advantages) not possible with polyclonal antibody mixtures.

The present invention provides vertebrates and cells, such as transgenic mice or rats or transgenic mouse or rat cells. Furthermore, the invention relates to methods of using the vertebrates to isolate antibodies or nucleotide sequences encoding antibodies. Antibodies, nucleotide sequences, pharmaceutical compositions and uses are also provided by the invention.

To this End, the Present Invention Provides, in a First Configuration

A non-human vertebrate (optionally a mouse or a rat) or vertebrate cell whose genome comprises:
(a) An immunoglobulin heavy chain locus comprising one or more human V gene segments (optionally a plurality of VH), one or more human D gene segments and one or more human J gene segments upstream of a constant region; optionally wherein the heavy chain locus is according to (a) of the second configuration described below; and
(b) An immunoglobulin light chain locus comprising either
  (i) one or more human VH gene segments and one or more human J gene segments upstream of a constant region (optionally a rearranged $V_H J_L C_L$ or $V_H J_\lambda C_L$, wherein the $C_L$ is $C_\lambda$ or $C_\kappa$); or
  (ii) one or more human VL gene segments, one or more human D gene segments and one or more human $J_H$ gene segments upstream of a constant region (optionally a rearranged $V_L DJ_H C_L$ or $V_\lambda DJ_H C_L$, wherein the $C_L$ is $C_\lambda$ or $C_\kappa$); or
  (iii) one or more human VL gene segments selected from the group consisting of: a $V_\lambda II$ gene family member, $V_\lambda VII$ 4A, $V_{\lambda II}$ 2.1, $V_\lambda VII$ 4A, a $V_\lambda 1$ gene family member, a $V_\lambda 3$ gene family member, IGLV1S2, $V_\lambda 3$-cML70, lalh2, lalyvl, la3h3, Kv325, a VκI gene family member, id-15A (KL012), $V_\kappa II$ family member, a $V_\kappa III$ family member, a VκI gene family member, κI-15A (KL012), $V_\kappa II$ A2 (optionally the A2a allele), $V_\kappa$ A27 (Humkv325) and a gene segment at least 80% identical thereto, and one or more human $J_L$ gene segments upstream of a constant region; optionally the one or more VL gene segments are selected from List A1, A2, A1.1, A1.2, A2.1, A2.2, A2.3 or A2.4 below.

Wherein the gene segments in the heavy chain locus are operably linked to the constant region thereof, and the gene segments in the light chain locus are operably linked to the constant region thereof, so that upon immunisation the mouse is capable of producing an antibody comprising heavy chains produced by recombination of the heavy chain locus and light chains produced by recombination of the light chain locus.

This configuration of the invention, thus, provides for the possibility of novel, synthetic antibody and gene repertoires in a transgenic non-human vertebrate, such as a mouse or rat. Such new repertoires are desirable, since they provide for the possibility of a novel pool of antibodies from which lead antibodies can be selected following immunisation of the vertebrate with a predetermined antigen. This, therefore, provides for a pool from which antibodies with desirable characteristics can be isolated, for example, antibodies with relatively high affinity for specific target antigen binding. It is desirable to isolate high affinity antibodies directly from the immunised vertebrate, since this can provide for an antibody lead that is potentially useful as a therapeutic and/or prophylactic medicament without the need for further extensive affinity maturation (eg, by in vitro antibody display such as ribosome display or phage display). Modification of the effector portions of the antibody can be made as desired (eg, humanisation of the constant region), without the need to manipulate the sequences of the variable regions. Alternatively, or additionally, the pool of antibodies may allow for selection of a lead antibody with desirable biophysical characteristics and/or epitope specificity. The latter may be important for finding lead antibodies against epitopes that have not previously raised therapeutic and/or prophylactic antibodies or epitopes that are difficult to reach by antibodies generated by antibody gene diversities generated by prior non-human vertebrates bearing transgenic immunoglobulin loci, eg, those based on the single human genome represented by the RPCI-11 BACs.

The cells of the invention (according to any aspect or configuration) is, for example, a B-cell, hybridoma or a stem cell, optionally an embryonic stem cell or haematopoietic stem cell. In one aspect the ES cell is derived from the mouse C57BL/6N, C57BL/6J, 129S5 or 129Sv strain. In one aspect the non-human vertebrate is a rodent, suitably a mouse, and cells of the invention, are rodent cells or ES cells, suitably mouse ES cells. The ES cells of the present invention can be used to generate animals using techniques well known in the art, which comprise injection of the ES cell into a blastocyst followed by implantation of chimaeric blastocystys into females to produce offspring which can be bred and selected for homozygous recombinants having the required insertion. In one aspect the invention relates to a transgenic animal comprised of ES cell-derived tissue and host embryo derived tissue. In one aspect the invention relates to genetically-altered subsequent generation animals, which include animals having a homozygous recombinants for the VDJ and/or VJ regions.

Vertebrates bearing one or more light chain loci according to (b)(i) and (ii) provide for novel and potentially expanded antibody and gene repertoires by exploiting synthetic, non-naturally-occurring, combinations of immunoglobulin gene segments (V, D, J, C). In this respect, the present inventors have realised the desirability and possibility of providing for antibody and gene repertoires that mix heavy chain gene segments with those of light chain loci. This is based on observations of the inventors: Firstly, nature suggests the possibility of functional antibodies having VH-VH or VL-VL pairings (as opposed to more classical VH-VL pairings). For example, reference is made to heavy chain antibodies of Camelidae which produce antibodies with paired VH domains and is devoid of light chain VL domains (eg, see Nature. 1993 Jun. 3; 363(6428):446-8; Naturally occurring antibodies devoid of light chains; Hamers-Casterman C, Atarhouch T, Muyldermans S, Robinson G, Hamers C, Songa E B, Bendahman N, Hamers R). These antibodies function to specifically bind antigen, such antibodies being found in the blood of such Camelidae (eg, llamas, camels, alpacas). Such antibodies with VH pairs can also be synthetically produced to provide therapeutic and prophylactic medicaments (eg, see WO1994004678, WO2004041862, WO2004041863). Transgenic mice also can produce such heavy chain antibodies and the in vivo production of the antibodies allows the mouse's immune system to select for VH-VH pairings, sometimes selecting for such pairings in which mutations have been introduced in vivo by the mouse to accommodate the pairing (WO2010109165A2). Thus, the inventors realised that the adoption of an in vivo antibody production system (rather than an in vitro system such as phage or ribosome display of antibodies) is desirable to accommodate the synthetic immunoglobulin gene segment combinations that are now contemplated by the present invention.

A second observation of the present inventors lies in the architecture of naturally-occurring immunoglobulin loci, and in particular the arrangement of recombination signal sequences (RSSs) that mediate V(D)J recombination in vivo (see, eg, Cell. 2002 April; 109 Suppl:S45-55. The mechanism and regulation of chromosomal V(D)J recombination; Bassing C H, Swat W, Alt F W, the disclosure of which is incorporated herein by reference). As illustrated in FIG. 6, two types of RSS element have been identified: a one-turn RSS (12-RSS) and a two-turn RSS (23-RSS). In natural VJ recombination in the lambda light chain locus, recombination if effected between a two-turn RSS that lies 3' of a V lambda and a one-turn RSS that lies 5' of a J lambda, the RSSs being in opposite orientation. In natural VJ recombination in the kappa light chain locus, recombination if effected between a one-turn RSS that lies 3' of a V kappa and a two-turn RSS that lies 5' of a J kappa, the RSSs being in opposite orientation. In natural VD recombination in the heavy chain locus, recombination if effected between a two-turn RSS that lies 3' of a VH and a one-turn RSS that lies 5' of a D, the RSSs being in opposite orientation. In natural DJ recombination in the heavy chain locus, recombination if effected between a one-turn RSS that lies 3' of a D and a two-turn RSS that lies 5' of a JH, the RSSs being in opposite orientation. Thus, generally a two-turn RSS is compatible with a one-turn RSS in the opposite orientation. The inventors realised that they could use this observation in constructing transgenic immunoglobulin loci such that a 5' gene segment can recombine with a 3' gene segment (eg, a V with a J; or a V with a D) when there is provided a two-turn RSS and a one-turn RSS in the opposite orientation, with each RSS adjacent a respective one of the gene segments. Thus, the inventors realised in one embodiment that an immunoglobulin locus can be constructed with one or more of the following arrangements (5' to 3'):—

(k) [V (heavy, lambda or kappa)]-[two-turn RSS]-[one-turn RSS]-[D]-[JH], wherein said RSSs are in an opposite orientation;

(l) [VH]-[D]-[two-turn RSS]-[one-turn RSS]-[J lambda], wherein said RSSs are in an opposite orientation;

(m) [VH]-[D]-[one-turn RSS]-[two-turn RSS]-[J kappa], wherein said RSSs are in an opposite orientation;

(n) [VH or V kappa]-[two-turn RSS]-[one-turn RSS]-[J lambda], wherein said RSSs are in an opposite orientation;

(o) [V kappa]-[one-turn RSS]-[two-turn RSS]-[JH or J lambda], wherein said RSSs are in an opposite orientation;

(p) [V (heavy, lambda or kappa)]-[one-turn RSS]-[two-turn RSS]-[D]-[JH], wherein said RSSs are in an opposite orientation;

(q) [VH]-[D]-[one-turn RSS]-[two-turn RSS]-[J lambda], wherein said RSSs are in an opposite orientation;

(r) [VH]-[D]-[two-turn RSS]-[one-turn RSS]-[1 kappa], wherein said RSSs are in an opposite orientation;

(s) [VH or V kappa]-[one-turn RSS]-[two-turn RSS]-[J lambda], wherein said RSSs are in an opposite orientation;

(t) [V kappa]-[two-turn RSS]-[one-turn RSS]-[JH or J lambda], wherein said RSSs are in an opposite orientation.

The skilled person will realise that standard molecular biology techniques can be used to provide vectors comprising synthetic combinations of RSS with V, D or J for use in this aspect of the invention, such that the vectors can be used to build a transgenic immunoglobulin locus (eg, using homologous recombination and/or recombinase mediated cassette exchange as known in the art, eg, see U.S. Pat. No. 7,501,552 (Medarex), U.S. Pat. No. 5,939,598 (Abgenix), U.S. Pat. No. 6,130,364 (Abgenix), WO02/066630 (Regeneron), WO2011004192 (Genome Research Limited), WO2009076464, WO2009143472 and WO2010039900 (Ablexis), the disclosures of which are explicitly incorporated herein. For example, such synthetic combinations with RSS and gene segments can be made using standard recombineering techniques in *E coli* to construct BAC vectors harbouring the synthetic combination prior to insertion in embryonic stem cells using homologous recombination or RMCE (eg, using cre/lox site-specific recombination). Details of recombineering can be found online at www.genebridges.com and in EP1034260 and EP1204740 the disclosures of which are explicitly incorporated herein.

In one embodiment of (b)(i), all of the light chain locus V gene segments are human VH gene segments (optionally with one or more human V lambda gene segments).

In one embodiment of (b)(i), the constant region is a mouse, rat or human CL, eg, Cλ. In one embodiment, the J and constant regions are provided by one or more human JλCλ.

Although having utility generally to any antigen and disease setting, vertebrates bearing one or more light chain loci according to (b)(iii) are useful, in particular, for generating antibody leads against infectious disease pathogens. In this respect, the present inventors have realised the desirability and possibility of providing for antibody and gene repertoires that are biased to immunoglobulin gene segments commonly found in natural antibody reactions of humans to infectious disease pathogens. The inventors realised that it would be desirable to provide for vertebrates, cells, methods etc for the production of therapeutic and/or prophylactic antibodies based on natural human immune responses to antigens, such as antigens of infectious disease pathogens. In this respect, the literature observes frequently used immunoglobulin gene segments to raise anti-infective responses in humans (Table 1).

TABLE 1

Immunoglobulin Gene Usage in Human Antibody Responses to Infectious Disease Pathogens

| GENE | ANTIGEN | ORGANISM | REFERENCES [Human Ab Source] |
|---|---|---|---|
| BACTERIAL PATHOGENS | | | |
| KAPPA V GENES | | | |
| Vκ II germline gene A2 + JK3<br>Vκ II family gene + JK4<br>94% identical to the A27<br>(Humkv325) germ line gene<br>a VκI gene family member; κI-15A (KL012)<br>LAMBDA V GENES<br>Four Vλ VII family members that are 96-98% identical to each other<br>Vλ II family members (82, 89 and 91% homologous to Vλ2.1 gene) + VHIII segments closely homologous to germline gene 9.1<br>V$_\lambda$VII 4A<br>All with Jλ homologous to germline Jλ2 and Jλ3<br>VH GENES<br>VH 96% identical to the VH germ line gene segment DP77 (V3-21)<br>LSG6.1, LSG12.1, V$_H$III VH26, V$_H$III 9.1<br>VH and VL COMBINATIONS<br>V$_H$III 9.1 + V$_\lambda$VII 4A<br>V$_H$III 9.1 + V$_\lambda$II 2.1<br>V$_H$III 9.1 + V$_\kappa$II A2<br>V$_H$III VH26 + V$_\lambda$II 2.1<br>V$_H$III 9.1; V$_H$III H11; V$_H$III VH26<br>κI 15A<br>Vλ2.1 | Haemophilus influenzae type b polysaccharide (Hib PS) | Haemophilus influenzae | 1. Lonberg, Nat Biotech 2005; [human PBMCs]<br>2. Adderson et al, J Clin Invest 1992; [Human PBLs]<br>3. Chung et al, J Immunol 1993<br>4. Nadel et al, J Immunol 1998<br>5. Feeney et al, J Clin Invest 1996<br>6. Lucas et al, Infect Immun 1994; [Human PBLs]<br>7. Adderson et al, J Clin Invest 1993; [Human PBLs]<br>8. Granoff et al, J Clin Invest 1993; [human PBLs]<br>9. Azmi et al, Infect Immun 1994; [human tonsil cells] |
| | Polysaccharide capsule of E coli K1 | E coli K1 | |
| | Meningococcal B polysaccharide; Poly[α(2→8)-N-acetylneuraminic acid | Neisseria meningitidis Group B | 9. Azmi et al, Infect Immun 1994 |

TABLE 1-continued

Immunoglobulin Gene Usage in Human Antibody Responses to Infectious Disease Pathogens

| GENE | ANTIGEN | ORGANISM | REFERENCES [Human Ab Source] |
|---|---|---|---|
| VIRAL PATHOGENS | | | |
| VHIII or VHIV family member | HSV 120-kD glycoprotein | Herpes family virus *Herpes simplex virus* (HSV); HSV-1; HSV-2 | 10. Huang et al, J Clin Invest 1992; [human tonsils] |
| Vλl or Vλ3 member | | | |
| VH26 + Dk1 + JH6 with IGLV1S2 + Jλ2 | 116-, 105-, 64-kD glycoproteins of VZV | Varicella zoster virus (VZV) | |
| VH4.18 | | | |
| VH2-1 (VH3) + D region Dxp1 + JH5 with Vλ3 cML70 + Jλ3 | | | |
| VH1GRR + JH3 + Dn4r or D2r with IGLV1S2 + Jλ2 | | | |
| For VZV Abs: ha3h2 (VH3) with Ialh2 (Vλ); or ha1c1 (VH1) with Ialv1 (Vλ1) | | | |
| For VZV Abs: ha4h3 (VH4) with Ia3h3 (Vλ3) | | | |
| Hv1051 (VH) | | *Cytomegalovirus* (CMV) | 10. Huang et al, J Clin Invest 1992; |
| Kv325 (Vk) | | | |
| 71-2 (VH) | | HIV | 10. Huang et al, J Clin Invest 1992; |
| Hv1f10 (VH) | | | 11. Wang & Palese, Science 2011 |
| VH4.11 | | | |
| 71-4 (VH) | | | |
| VH251 | | | |
| VH1-69 | Haemagglutinin (HA) | Influenza virus, eg, Group 1 and/or Group 2 Influenza A virus; eg, H1N1, H2N2, or H3N2 or H7N2 or H7N7 influenza virus | 12. Ekiert et al, Science 2009 |
| VH1-69 | | | 13. Throsby et al, PLoS One 2008 |
| | | | 14. Sui et al, Nat Struct Mol Biol 2009 |
| | | | 15. Ekiert et al, Science 2011 |

REFERENCES

1. Nat. Biotechnol. 2005 September; 23(9):1117-25; Human antibodies from transgenic animals; Lonberg N.
2. J Clin Invest. 1992 March; 89(3):729-38; Immunoglobulin light chain variable region gene sequences for human antibodies to *Haemophilus influenzae* type b capsular polysaccharide are dominated by a limited number of V kappa and V lambda segments and VJ combinations; Adderson E E, Shackelford P G, Insel R A, Quinn A, Wilson P M, Carroll W L
3. J. Immunol. 1993 Oct. 15; 151(8):4352-61; Clonal characterization of the human IgG antibody repertoire to *Haemophilus influenzae* type b polysaccharide. V. In vivo expression of individual antibody clones is dependent on Ig CH haplotypes and the categories of antigen; Chung G H, Scott M G, Kim K H, Kearney J, Siber G R, Ambrosino D M, Nahm M H.
4. J. Immunol. 1998 Dec. 1; 161(11):6068-73; Decreased frequency of rearrangement due to the synergistic effect of nucleotide changes in the heptamer and nonamer of the recombination signal sequence of the V kappa gene A2b, which is associated with increased susceptibility of Navajos to *Haemophilus influenzae* type b disease; Nadel B, Tang A, Lugo G, Love V, Escuro G, Feeney A J.
5. J Clin Invest. 1996 May 15; 97(10):2277-82; A defective Vkappa A2 allele in Navajos which may play a role in increased susceptibility to *haemophilus influenzae* type b disease; Feeney A J, Atkinson M J, Cowan M J, Escuro G, Lugo G.
6. Infect Immun. 1994 September; 62(9):3873-80; Variable region sequences of a protective human monoclonal antibody specific for the *Haemophilus influenzae* type b capsular polysaccharide; Lucas A H, Larrick J W, Reason D C.
7. J Clin Invest. 1993 June; 91(6):2734-43; Restricted immunoglobulin VH usage and VDJ combinations in the human response to *Haemophilus influenzae* type b capsular polysaccharide. Nucleotide sequences of monospecific anti-*Haemophilus* antibodies and polyspecific antibodies cross-reacting with self antigens; Adderson E E, Shackelford P G, Quinn A, Wilson P M, Cunningham M W, Insel R A, Carroll W L.
8. J Clin Invest. 1993 March; 91(3):788-96; Variable region expression in the antibody responses of infants vaccinated with *Haemophilus influenzae* type b polysaccharide-protein conjugates. Description of a new lambda light chain-associated idiotype and the relation between idiotype expression, avidity, and vaccine formulation. The Collaborative Vaccine Study Group; Granoff D M, Shackelford P G, Holmes S J, Lucas A H.
9. Infect Immun. 1994 May; 62(5):1776-86; Variable region sequences and idiotypic expression of a protective human immunoglobulin M antibody to capsular polysaccharides of *Neisseria meningitidis* group B and *Escherichia coli* K1; Azmi F H, Lucas A H, Raff H V, Granoff D M.
10. J Clin Invest. 1992 December; 90(6):2197-208; Sequence analyses of three immunoglobulin G anti-virus antibodies reveal their utilization of autoantibody-related immunoglobulin Vh genes, but not V lambda genes; Huang D F, Olee T, Masuho Y, Matsumoto Y, Carson D A, Chen P P.
11. Science. 2011 Aug. 12; 333(6044):834-5, Biochemistry. Catching a moving target, Wang T T, Palese P
12. Science. 2009 Apr. 10; 324(5924):246-51. Epub 2009 Feb. 26; Antibody recognition of a highly conserved influenza virus epitope; Ekiert D C, Bhabha G, Elsliger M A, Friesen R H, Jongeneelen M, Throsby M, Goudsmit J, Wilson I A.
13. PLoS One. 2008; 3(12):e3942. Epub 2008 Dec. 16; Heterosubtypic neutralizing monoclonal antibodies cross-protective against H5N1 and H1N1 recovered from human IgM+ memory B cells; Throsby M, van den Brink E, Jongeneelen M, Poon L L, Alard P, Cornelissen L, Bakker A, Cox F, van Deventer E, Guan Y, Cinatl J, ter Meulen J, Lasters I, Carsetti R, Peiris M, de Kruif J, Goudsmit J.
14. Nat Struct Mol Biol. 2009 March; 16(3):265-73. Epub 2009 Feb. 22, Structural and functional bases for broad-spectrum neutralization of avian and human influenza A viruses, Sui J, Hwang W C, Perez S, Wei G, Aird D, Chen L M, Santelli E, Stec B, Cadwell G, Ali M, Wan H, Murakami A, Yammanuru A, Han T, Cox N J, Bankston L A, Donis R O, Liddington R C, Marasco W A.
15. Science. 2011 Aug. 12; 333(6044):843-50. Epub 2011 Jul. 7, A highly conserved neutralizing epitope on group 2 influenza A viruses, Ekiert D C, Friesen R H, Bhabha G, Kwaks T, Jongeneelen M, Yu W, Ophorst C, Cox F, Korse H J, Brandenburg B, Vogels R, Brakenhoff J P, Kompier R, Koldijk M H, Cornelissen L A, Poon L L, Peiris M, Koudstaal W, Wilson I A, Goudsmit J.

In one embodiment, in (b)(i) the J gene segments of the light chain locus are $J_\lambda$ gene segments and optionally the constant region of the light chain locus is a lambda constant region; or in (b)(ii) the VL is a $V_\lambda$ and optionally the constant region of the light chain locus is a lambda constant region. Alternatively, the constant region is C kappa.

In one embodiment, in (b)(i) the V gene segment repertoire of the light chain locus comprises or consists of one or more VH gene segments selected from the group consisting of: a $V_H$III gene family member (optionally, a VHIIIa or VHIIIb family member), a $V_H$IV gene family member, $V_H$III 9.1 (VH3-15), $V_H$III VH26 (VH3-23), $V_H$3-21, LSG6.1, LSG12.1, DP77 (V3-21), $V_H$ H11, VH1GRR, ha3h2, $V_H$III-VH2-1, VH4.18, ha4h3, Hv1051, 71-2, Hv1f10, VH4.11, 71-4, VH251, VH1-69 and a gene segment at least 80% identical thereto. These gene segments are useful because they expand the repertoire in vivo to VH gene segments that are found in natural human immune responses to antigens, such as antigens of infectious disease pathogens. This is useful, for example, when the vertebrate is immunised with an antigen of an infectious disease pathogen, for generation and isolation of an antibody for treating and/or preventing a disease or condition mediated by said pathogen. In one example, in (b)(i) the V gene segment repertoire of the light chain locus comprises or consists of only VH gene segment selected from the group consisting of: a $V_H$III gene family member (optionally, a VHIIIa or VHIIIb family member), a $V_H$IV gene family member, $V_H$III 9.1 (VH3-15), $V_H$III VH26 (VH3-23), $V_H$3-21, LSG6.1, LSG12.1, DP77 (V3-21), $V_H$ H11, VH1GRR, ha3h2, $V_H$I-ha1c1, $V_H$III-VH2-1, VH4.18, ha4h3, Hv1051, 71-2, Hv1f10, VH4.11, 71-4, VH251, VH1-69 and a gene segment at least 80% identical thereto. This is useful to bias the immune response of the vertebrate (and thus resultant lead antibodies) to a predetermined gene segment, eg, one known to be commonly used in natural human immune responses to antigens, such as antigens of infectious disease pathogens. For example, VH1-69 is commonly used to produce antibodies in humans against Influenza virus (see Table 1); it is possible, therefore, to confine the single VH segment to VH1-69 in embodiment (b)(i) of the invention.

In one embodiment, in (b)(iii) the light chain locus V gene segment repertoire consists of only one (optionally only two, three or four) VL gene segment type (optionally and one or mutants thereof), wherein the VL gene segment is selected from said group of VL gene segments. This is useful to bias the immune response of the vertebrate (and thus resultant lead antibodies) to a predetermined gene segment, eg, one known to be commonly used in natural human immune responses to antigens, such as antigens of infectious disease pathogens.

In one embodiment, in (a) said constant region is a heavy chain endogenous non-human vertebrate (optionally host mouse or rat) constant region and/or in (b) said constant region is a light chain endogenous non-human vertebrate (optionally host mouse or rat) constant region.

In one embodiment in any configuration of the invention, the genome has been modified to prevent or reduce the expression of fully-endogenous antibody. Examples of suitable techniques for doing this can be found in PCT/GB2010/051122, U.S. Pat. No. 7,501,552, U.S. Pat. No. 6,673,986, U.S. Pat. No. 6,130,364, WO2009/076464, EP1399559 and U.S. Pat. No. 6,586,251, the disclosures of which are incorporated herein by reference. In one embodiment, the non-human vertebrate VDJ region of the endogenous heavy chain immunoglobulin locus, and optionally VJ region of the endogenous light chain immunoglobulin loci (lambda and/or kappa loci), have been inactivated. For example, all or part of the non-human vertebrate VDJ region is inactivated by inversion in the endogenous heavy chain immunoglobulin locus of the mammal, optionally with the inverted region being moved upstream or downstream of the endogenous Ig locus (see, eg, WO2011004192, the disclosure of which is incorporated herein by reference). For example, all or part of the non-human vertebrate VJ region is inactivated by inversion in the endogenous kappa chain immunoglobulin locus of the mammal, optionally with the inverted region being moved upstream or downstream of the endogenous Ig locus. For example, all or part of the non-human vertebrate VJ region is inactivated by inversion in the endogenous lambda chain immunoglobulin locus of the mammal, optionally with the inverted region being moved upstream or downstream of the endogenous Ig locus. In one embodiment the endogenous heavy chain locus is inactivated in this way as is one or both of the endogenous kappa and lambda loci.

Additionally or alternatively, the vertebrate has been generated in a genetic background which prevents the production of mature host B and T lymphocytes, optionally a RAG-1-deficient and/or RAG-2 deficient background. See U.S. Pat. No. 5,859,301 for techniques of generating RAG-1 deficient animals.

Thus, in one embodiment of any configuration or aspect of the invention herein, endogenous heavy and light chain expression has been inactivated.

In a Second Configuration of the Invention, there is Provided

A non-human vertebrate (optionally a mouse or a rat) or vertebrate cell whose genome comprises:
(a) An immunoglobulin heavy chain locus comprising one or more human V gene segments (eg, a plurality of VH), one or more human D gene segments and one or more human J gene segments upstream of a constant region; and
(b)
  (i) An unrearranged immunoglobulin light chain locus comprising one or more human VH gene segments and one or more human J gene segments upstream of a constant region, wherein each human VH gene segment is a human gene segment identical to (or mutant of, eg, having up to 15 or 10 nucleotide changes from the human gene segment) a human VH gene segment (eg, a germline VH gene segment; eg, a gene segment selected from List A1, A2, A1.1, A1.2, A2.1, A2.2, A2.3 or A2.4 below.) used to produce a rearranged VDJ encoding a heavy chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism); or
  (ii) An immunoglobulin light chain locus comprising a rearranged VJ region or VDJ region upstream of a constant region, wherein the nucleotide sequence of the recombined region is identical to a nucleotide sequence produced by the recombination of a human J gene segment and optionally a human D gene segment with a human VH gene segment that is identical to (or mutant of; eg, having up to 15 or 10 nucleotide changes from the human gene segment)) the human VH gene segment (eg, germline VH gene segment; eg, a gene segment selected from List A1, A2, A1.1, A1.2, A2.1, A2.2, A2.3 or A2.4 below.) used to produce a rearranged VDJ encoding a heavy chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism);
(c) Wherein the gene segments in the heavy chain locus are operably linked to the constant region thereof, and the gene segments or VJ or VDJ in the light chain locus are operably linked to the constant region thereof, so that upon immunisation the mouse is capable of producing an antibody comprising heavy chains produced by recombination of the heavy chain locus and light chains derived from the light chain locus;
(d) Optionally when (b)(i) applies, each said VH gene segment in the light chain locus is selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto; optionally each VH gene segment is selected from List A1, A2, A1.1, A1.2, A2.1, A2.2, A2.3 or A2.4 below.
(e) Optionally when (b)(ii) applies, the nucleotide sequence of the recombined region is identical to a nucleotide sequence produced by the recombination of a human J gene segment and optionally a human D gene segment with a human VH gene segment selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto; optionally each VH gene segment is selected from List A1, A2, A1.1, A1.2, A2.1, A2.2, A2.3 or A2.4 below.

In one embodiment, the antigen is an antigen expressed by a bacterial or viral infectious disease pathogen, eg, any of the pathogens listed in Table 1. For example, the antigen is an antigen selected from the antigens listed in Table 1.

In one embodiment of any aspect, configuration or embodiment of the invention herein, the "human individual harbouring said organism" is a patient that has natural resistance to the pathogen and produces antibodies that bind to the pathogen or an antigen expressed thereby.

In one embodiment of the second configuration, the J gene segments of the light chain locus are $J_\lambda$ gene segments and optionally the constant region of the light chain locus is a lambda constant region. Alternatively, the constant region is C kappa.

In one embodiment of the second configuration, the V gene segment repertoire of the light chain locus comprises or consists of one or more VH gene segments selected from the group consisting of: a $V_H$III gene family member (optionally, a VHIIIa or VHIIIb family member), a $V_H$IV gene family member, $V_H$III 9.1 (VH3-15), $V_H$III VH26 (VH3-23), $V_H$3-21, LSG6.1, LSG12.1, DP77 (V3-21), $V_H$ H11, VH1GRR, ha3h2, $V_H$I-ha1c1, $V_H$III-VH2-1, VH4.18, ha4h3, Hv1051, 71-2, Hv1f10, VH4.11, 71-4, VH251, VH1-69 and a gene segment at least 80% identical thereto. These gene segments are useful because they expand the repertoire in vivo to VH gene segments that are found in natural human immune responses to antigens, such as antigens of infectious disease pathogens. This is useful, for example, when the vertebrate is immunised with an antigen of an infectious disease pathogen, for generation and isolation of an antibody for treating and/or preventing a disease or condition mediated by said pathogen. In one example, in (b)(i) the V gene segment repertoire of the light chain locus comprises or consists of only VH gene segment selected from the group consisting of: a $V_H$III gene family member (optionally, a VHIIIa or VHIIIb family member), a $V_H$IV gene family member, $V_H$III 9.1 (VH3-15), $V_H$III VH26 (VH3-23), $V_H$3-21, LSG6.1, LSG12.1, DP77 (V3-21), $V_H$ H11, VH1GRR, ha3h2, $V_H$I-ha1c1, $V_H$III-VH2-1, VH4.18, ha4h3, Hv1051, 71-2, Hv1f10, VH4.11, 71-4, VH251, VH1-69 and a gene segment at least 80% identical thereto. This is useful to bias the immune response of the vertebrate (and thus resultant lead antibodies) to a predetermined gene segment, eg, one known to be commonly used in natural human immune responses to antigens, such as antigens of infectious disease pathogens. For example, VH1-69 is commonly used to produce antibodies in humans against Influenza virus (see Table 1); it is possible, therefore, to confine the single VH segment to VH1-69 in embodiment (b)(i) of the invention.

In one embodiment of the second configuration, in (a) said constant region is a heavy chain endogenous non-human vertebrate (optionally host mouse or rat) constant region.

In one embodiment of the second configuration, in (b) said constant region is a light chain endogenous non-human vertebrate (optionally host mouse or rat) constant region.

In one embodiment of the second configuration, the genome of said vertebrate or cell is homozygous for light chain locus (b)(i) or (ii); optionally wherein:

the V gene segment repertoire of the light chain loci consists of one or more human VH gene segments selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VH1-ha1c1, VHIII-VH2-1, VH4.18, ha4h3, Hv1051, 71-2, Hv1f10, VH4.11, 71-4, VH251, VH1-69 and a gene segment at least 80% identical thereto; or the recombed VJ or VDJ repertoire of the light chain loci consists of sequences identical to one or more nucleotide sequences produced by the recombination of a human VH gene segment selected from the group consisting of: a VHIII gene family member (optionally, a VHIIIa or VHIIIb family member), a VHIV gene family member, VHIII 9.1 (VH3-15), VHII VH26 (VH3-23), VH3-21, LSG6.1, LSG12.1, DP77 (V3-21), VH H11, VH1GRR, ha3h2, VH1-ha1c1, VHIII-VH2-1, VH4.18, ha4h3, Hv1051, 71-2, Hv1f10, VH4.11, 71-4, VH251, VH1-69 and a gene segment at least 80% identical thereto, with a human J gene segment and optionally a human D gene segment. In one embodiment, all of the light chain locus V gene segments are from this group.

In one embodiment of the second configuration, endogenous heavy and light chain expression has been inactivated, and wherein light chain loci according to the second configuration are the only functional light chain loci in the genome of the vertebrate or cell.

In one embodiment of the second configuration, each immunoglobulin light chain locus of said vertebrate or cell is according to (b)(i) and comprises only a single human VH gene segment selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto, optionally wherein the genome of the vertebrate or cell is homozygous for said light chain so that all light chain loci comprise the same, single human VH gene segment. In this embodiment (and generally in other embodiments, configurations and aspects of the invention), confinement of heavy and/or light chain locus architecture is useful for biasing or controlling the antibody and gene repertoire, eg, to mirror human immune responses as mentioned above. Provision of a single light or heavy chain variable (and optionally D and/or J) gene segment (or only this with closely related mutants thereof)—or confinement in embodiments below to a single rearranged V(D)J region or single heavy or light chain—is advantageous for simplifying the expression and production of therapeutic/prophylactic antibodies since this restricts the number of antibody species produced during downstream manufacture. A common heavy or light chain is advantageous to enable co-expression of a plurality (eg, two, three or more) different antibodies in the same expression medium, for example from the same host cell. See, eg, EP1523496 (Merus BV) and WO2011097603 (Regeneron Pharmaceuticals, Inc).

In one embodiment of the second configuration, each immunoglobulin light chain locus of said vertebrate or cell is according to (b)(ii) and comprises only a single rearranged VJ or VDJ region, optionally wherein the genome of the vertebrate or cell is homozygous for said light chain so that all light chain loci comprise the same, single rearranged VJ or VDJ region.

In one embodiment of the second configuration, each immunoglobulin light chain locus further comprises a VH gene segment or rearranged region that is a mutant (eg, having up to 15 or 10 nucleotide changes from the VH gene segment) respectively of said selected human VH gene segment or rearranged region, optionally wherein the genome of the vertebrate or cell is homozygous for said light chain mutant VH gene segment or rearranged region.

In one embodiment of the second configuration, each immunoglobulin light chain locus comprises only two or three human VH gene segments selected from said group, optionally wherein the genome of the vertebrate or cell is homozygous for said two or three light chain human VH gene segments.

In one embodiment of the second configuration, each immunoglobulin light chain locus comprises only two or three of said rearranged VJ or VDJ regions, optionally wherein the genome of the vertebrate or cell is homozygous for said two or three light chain rearranged VJ or VDJ regions.

The invention provides a monoclonal or polyclonal antibody composition prepared by immunisation of at least one vertebrate (eg, mouse or rat) according to any configuration, aspect or embodiment of the invention, optionally wherein the antigen is an antigen of an infectious disease pathogen (eg, a bacterial or viral pathogen antigen or an antigen listed in Table 1), optionally wherein the same antigen is used to immunise all the vertebrates; optionally wherein the antibody or antibodies are IgG-type (eg, IgG1).

The invention provides a first method of isolating an antibody that binds a predetermined antigen (eg, a bacterial or viral pathogen antigen or an antigen listed in Table 1), the method comprising
(a) providing a vertebrate (optionally a mouse or rat) according to according to any configuration, aspect or embodiment of the invention;
(b) immunising (eg, using a standard prime-boost method) said vertebrate with said antigen (optionally wherein the antigen is an antigen of an infectious disease pathogen);
(c) removing B lymphocytes from the vertebrate and selecting one or more B lymphocytes expressing antibodies that bind to the antigen;
(d) optionally immortalising said selected B lymphocytes or progeny thereof, optionally by producing hybridomas therefrom; and
(e) isolating an antibody (eg, and IgG-type antibody) expressed by the B lymphocytes.

In a first embodiment of the first method of the invention, the method comprises the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host. The skilled person will be aware of standard molecular biology techniques to do this. For example, see Harlow, E. & Lane, D. 1998, 5$^{th}$ edition, Antibodies: A Laboratory Manual, Cold Spring Harbor Lab. Press, Plainview, N.Y.; and Pasqualini and Arap, Proceedings of the National Academy of Sciences (2004) 101:257-259 for standard immunisation. Joining of the variable regions of an antibody to a human constant region can be effected by techniques readily available in the art, such as using conventional recombinant DNA and RNA technology as will be apparent to the skilled person. See e.g. Sambrook, J and Russell, D. (2001, 3'd edition) Molecular Cloning: A Laboratory Manual (Cold Spring Harbor Lab. Press, Plainview, N.Y.).

In one embodiment of the first method of the invention, the method comprises further making a mutant or derivative of the antibody.

A method of producing a polyclonal antibody mixture is provided, the method comprising carrying out the first method of the invention by separately immunising first and second vertebrates (optionally first and second mice or first and second rats) with antigen and combining the anti-antigen antibodies isolated from each vertebrate (or mutants or derivatives of said antibodies) to produce a polyclonal antibody mixture; optionally wherein the following apply separately or in combination ((i) and (ii); or (i) and (iii)):
(i) the vertebrates are immunised with the same antigen or different antigens (optionally wherein the different antigens are expressed by the same pathogenic organism (or by family members or different strains of the organism));
(ii) prior to immunisation the light chain loci of the vertebrates contain the identical VH gene repertoire (optionally a single VH gene) and optionally the identical J repertoire; optionally the light chain loci of the mammals are identical prior to immunisation;
(iii) prior to immunisation the light chain loci of the vertebrates contain the identical rearranged VJ or VDJ repertoire (optionally a single VJ or VDJ); optionally the light chain loci of the vertebrates are identical prior to immunisation.

A method of producing a polyclonal antibody mixture is provided, the method comprising carrying out the first method of the invention by immunising one or a plurality of vertebrates (optionally mice or rats) with first and second antigens and combining the anti-antigen antibodies isolated from each vertebrate (or mutants or derivatives of said antibodies) to produce a polyclonal antibody mixture; optionally wherein the following apply separately or in combination ((i) and (ii); or (i) and (iii)):
(i) the antigens are expressed by the same pathogenic organism (or by family members or different strains of the organism));
(ii) prior to immunisation the light chain loci of the vertebrates contain the identical VH gene repertoire (optionally a single VH gene) and optionally the identical J repertoire; optionally the light chain loci of the mammals are identical prior to immunisation;
(iii) prior to immunisation the light chain loci of the vertebrates contain the identical rearranged VJ or VDJ repertoire (optionally a single VJ or VDJ); optionally the light chain loci of the vertebrates are identical prior to immunisation.

The Invention Provides a Second Method:

A method of producing host cells (eg, Chinese Hamster Ovary (CHO) or HEK293 cells) capable of expressing a polyclonal antibody mixture is provided, the method comprising, in a method according to said first embodiment of the first method of the invention:—
(a) immunising one or a plurality of vertebrates (optionally mice or rats) with first and second antigens (optionally wherein the different antigens are expressed by the same pathogenic organism (or a family member thereof));
(b) isolating nucleic acid encoding first and second anti-antigen antibodies from B lymphocytes from said vertebrates;
(c) determining the nucleotide sequences of the heavy and light chain variable regions (optionally the entire heavy and/or light chain sequences) of the first antibody;
(d) determining the nucleotide sequence of the heavy variable region and optionally the light chain variable region of the second antibody;
(e) inserting the heavy chain variable region coding sequence of each antibody into a heavy chain expression vector; optionally wherein the constant region coding sequence of each heavy chain is exchanged for a nucleotide sequence that encodes a human or humanised constant region;

(f) inserting the light chain variable region coding sequence of the first antibody into a light chain expression vector; optionally wherein the constant region coding sequence of the light chain of the first antibody is exchanged for a nucleotide sequence that encodes a human or humanised constant region;

(g) optionally inserting the light chain variable region coding sequence of the second antibody into a light chain expression vector; optionally wherein the constant region coding sequence of the light chain of the second antibody is exchanged for a nucleotide sequence that encodes a human or humanised constant region; and (h) introducing each expression vector into a host cell and co-expressing antibody chains in a mixture of said host cells to produce antibodies, each antibody comprising one or both of said heavy chain variable regions and a light chain; optionally wherein the expression vectors are introduced together into the same host cell (eg, a CHO or HEK293 cell) so that the cell is capable of expressing antibody light chains and heavy chains, such that the cell or a plurality of the host cells express antibodies (eg, two, three, four or more different antibodies), each comprising one or both of said heavy chain variable regions and a light chain;

(i) optionally:
prior to immunisation the light chain loci of the vertebrates contain the identical VH gene repertoire (optionally a single VH gene segment) and optionally the identical J repertoire (optionally a single J gene segment); optionally the light chain loci of the vertebrates are identical prior to immunisation; or
prior to immunisation the light chain loci of the vertebrates contain the identical rearranged VJ or VDJ repertoire (optionally a single VJ or VDJ); optionally the light chain loci of the vertebrates are identical prior to immunisation.

(j) optionally:
producing a monoclonal or polyclonal antibody mixture, by expressing a monoclonal antibody or polyclonal mixture of said antibodies; optionally followed by isolating an antibody comprising the heavy chain variable region of the first and/or second antibodies.

The invention also provides a monoclonal or polyclonal antibody mixture so produced or a derivative antibody or mixture thereof, eg, where one or more constant region has been changed (eg, replaced with a different constant region such as a human constant region; or mutated to enhance or ablate Fc effector function). (optionally the entire heavy and/or light chain sequences)

In any of the methods of the invention, optionally each vertebrate used for immunisation is provided by (a) isolating from a human blood or tissue (eg, B lymphocytes (PBLs), peripheral blood mononuclear cells (PBMCs), bone marrow, spleen, tonsil or lymph node) sample a B lymphocyte that expresses an antibody that binds a predetermined antigen (eg, an antigen expressed by an infectious disease pathogen; optionally wherein said serum or tissue was from a human individual suffering, susceptible to, or recovered from, a disease or condition caused or mediated by an organism harbouring or secreting said antigen; or from a human individual harbouring said organism);

(b) determining which human germline VH gene segment was recombined in the human to produce the nucleotide sequence of said B lymphocyte that encodes the heavy chain variable region of the antibody;

(c) constructing a transgenic vertebrate wherein said human germline VH gene segment is provided in a light chain locus thereof according the first or second configuration of the invention; and (d) providing said transgenic vertebrate for immunisation in the first method of the invention.

The term "Human blood" herein includes a human blood product minus one or more non-B lymphocyte cellular populations, provided that the product retains antibody-producing cells, eg, PBLs.

In an embodiment of the first method of the invention, each vertebrate used for immunisation is provided by (a) isolating from a human blood or tissue (eg, B lymphocytes, PBMCs, bone marrow, spleen, tonsil or lymph node) sample a B lymphocyte that expresses an antibody that binds a predetermined antigen (eg, an antigen expressed by an infectious disease pathogen; optionally wherein said serum or tissue was from a human individual suffering, susceptible to, or recovered from, a disease or condition caused or mediated by an organism harbouring or secreting said antigen; or from a human individual harbouring said organism);

(b) determining a nucleotide sequence of said B lymphocyte that encodes a rearranged VDJ or VJ region of the antibody;

(c) constructing a transgenic vertebrate wherein said rearranged VDJ or VJ region is provided in a light chain locus thereof according to the first or second configuration of the invention; and (d) providing said transgenic vertebrate for immunisation in the first method of the invention.

Common Light Chain Antibodies & Bispecifics (eg, to Two Pathogen Antigens for Infectious Diseases)

The invention provides an isolated antibody (eg, IgG-type, such as IgG1-type, antibody) obtainable or obtained by the second method of the invention (including step (j), or a mutant or derivative antibody thereof wherein (i) the isolated antibody comprises two copies of the heavy chain variable region of said first antibody paired with two copies of the light chain variable region of said first antibody; or (ii) the isolated antibody comprises two copies of the heavy chain variable region of said second antibody paired with two copies of the light chain variable region of said first antibody; or (iii) the isolated antibody is a bispecific antibody comprising one copy of the heavy chain variable region of said first antibody paired with a copy of the light chain variable region of the first antibody, and one copy of the heavy chain variable region of said the antibody paired with a copy of the light chain variable region of the first antibody, optionally wherein the bispecific antibody binds to said first and second antigens; optionally for use in medicine, optionally for the treatment and/or prevention of an infectious disease.

In an aspect of the invention, there is provided a monoclonal or polyclonal antibody mixture (eg, IgG-type antibody or antibodies), wherein the monoclonal antibody or mixture is according to any configuration, aspect, embodiment or example of the invention, or a mutant or derivative antibody thereof optionally for use in medicine, optionally for the treatment and/or prevention of an infectious disease, wherein optionally wherein each antibody binds an antigen of an infectious disease pathogen, preferably the same antigen.

In an aspect of the invention, there is provided the use of an isolated, monoclonal or polyclonal antibody according to any configuration, aspect, embodiment or example of the invention, or a mutant or derivative antibody thereof in the manufacture of a medicament for the treatment and/or prevention of an infectious disease, optionally wherein the infectious disease is a disease caused by a bacterial or viral pathogen.

An example of a mutant antibody is one that bears up to 15 or 10 amino acid mutations in its variable regions relative to an isolated antibody (eg, IgG-type, such as IgG1-type, antibody) obtainable or obtained by the second method of the invention (including step (j). An example of a derivative is one that has been modified to replace a constant region with a different constant region such as a human constant region; or mutated to enhance or ablate Fc effector function.

Examples of infectious diseases are diseases caused or mediated by a bacterial or viral pathogen, eg, a pathogen listed in Table 1. Examples of antigens are those listed in Table 1.

For example, the infectious disease is selected from the group consisting of a disease caused by a pathogen selected from the group consisting of *Haemophilus influenza*, *E. coli*, *Neisseria meningitidis*, a herpes family virus, cytomegalovirus (CMV), HIV and influenza virus.

The invention further provides a nucleotide sequence encoding an antibody according to any configuration, aspect, embodiment or example of the invention, optionally wherein the nucleotide sequence is part of a vector.

The invention further provides a pharmaceutical composition comprising the antibody or antibodies of any configuration, aspect, embodiment or example of the invention and a diluent, excipient or carrier.

In a Third Configuration of the Invention, there is Provided

A non-human vertebrate (optionally a mouse or a rat) or vertebrate cell whose genome comprises:
(a) An immunoglobulin heavy chain locus comprising either:—
  (i) one or more human VL gene segments, one or more human D gene segments and one or more human J gene segments upstream of a constant region (optionally a rearranged $V_L DJ_H C_H$ or $V_\lambda DJ_H C_H$); or
  (ii) one or more human VH gene segments selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical; one or more human D gene segments and one or more human $J_H$ gene segments upstream of a constant region; optionally each VH gene segment (and optionally each D) is selected from List A1, A2, A1.1, A1.2, A2.1, A2.2, A2.3 or A2.4 below; and
(b) An immunoglobulin light chain locus comprising one or more human V gene segments (eg, a plurality of VL) and one or more human J gene segments upstream of a constant region, optionally wherein the light chain locus is according to (b)(i) or (b)(ii) of the first configuration of the invention;

Wherein the gene segments in the heavy chain locus are operably linked to the constant region thereof, and the gene segments in the light chain locus are operably linked to the constant region thereof, so that upon immunisation the mouse is capable of producing an antibody comprising heavy chains produced by recombination of the heavy chain locus and light chains produced by recombination of the light chain locus.

In one example, in (a)(i) all of the heavy chain locus V gene segments are human VL gene segments.

In one embodiment of the third configuration, the V gene segment repertoire of the light chain locus comprises or consists of one or more VL gene segments selected from the group consisting of a $V_\lambda II$ gene family member, $V_\lambda VII$ 4A, $V_\lambda II$ 2.1, $V_\lambda VII$ 4A, a $V_\lambda 1$ gene family member, a $V_\lambda 3$ gene family member, IGLV1S2, $V_\lambda 3$-cML70, 1alh2, 1alyv1, 1a3h3, Kv325, a VκI gene family member, κI-15A (KL012), $V_\kappa II$ family member, a $V_\kappa III$ family member, a $V_\kappa I$ gene family member, κI-15A (KL012), $V_\kappa II$ A2 (optionally the A2a allele), $V_\kappa$ A27 (Humkv325) and a gene segment at least 80% identical thereto; optionally each VL gene segment is selected from List A1, A2, A1.1, A1.2, A2.1, A2.2, A2.3 or A2.4 below; and/or wherein or in (a)(ii) the heavy chain locus V gene segment repertoire consists of only one (or two, three or four) VH gene segment type (optionally and one or mutants thereof), wherein the VH gene segment is selected from said group of VH gene segments. This is useful to bias the immune response of the vertebrate (and thus resultant lead antibodies) to a predetermined gene segment, eg, one known to be commonly used in natural human immune responses to antigens, such as antigens of infectious disease pathogens.

In one embodiment of the third configuration, in (a) said constant region is a heavy chain endogenous non-human vertebrate (optionally host mouse or rat) constant region and/or in (b) said constant region is a light chain endogenous non-human vertebrate (optionally host mouse or rat) constant region.

In one embodiment of the third configuration, endogenous heavy and light chain expression has been inactivated.

A Fourth Configuration of the Present Invention Provides

A non-human vertebrate (optionally a mouse or a rat) or vertebrate cell whose genome comprises:
(a)
  (i) An unrearranged immunoglobulin heavy chain locus comprising one or more human VL gene segments, one or more human D gene segments and one or more $J_H$ gene segments upstream of a constant region, wherein each human VL gene segment is a human gene segment identical to (or mutant of, eg, having up to 15 or 10 nucleotide changes from the human gene segment) a human VL gene segment (eg, a germline VL gene segment; eg, a VL gene segment selected from List A1, A2, A1.1, A1.2, A2.1, A2.2, A2.3 or A2.4 below) used to produce a rearranged VJ encoding a light chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism); or
  (ii) An immunoglobulin heavy chain locus comprising a rearranged VJ region or VD) region upstream of a constant region, wherein the nucleotide sequence of the recombined region is identical to a nucleotide sequence produced by the recombination of a human J gene segment and optionally a human D gene segment with a human gene segment identical to (or mutant of, eg, having up to 15 or 10 nucleotide changes from the human gene segment) a human VL gene segment (eg, a germline VL gene segment; eg, a VL gene segment selected from List A1, A2, A1.1, A1.2, A2.1, A2.2, A2.3 or A2.4 below) used to produce a rearranged VJ encoding a light chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism);

(b) An immunoglobulin light chain locus comprising one or more human V gene segments (eg, a plurality of VL) and one or more human J gene segments upstream of a constant region; and (c) Wherein the gene segments in the light chain locus are operably linked to the constant region thereof, and the gene segments or VJ or VDJ in the heavy chain locus are operably linked to the constant region thereof, so that upon immunisation the mouse is capable of producing an antibody comprising light chains produced by recombination of the light chain locus and heavy chains derived from the heavy chain locus;

(d) Optionally when (a)(i) applies, each said VL gene segment in the heavy chain locus is selected from the group consisting of a VL gene segment selected from the group consisting of a VλII gene family member, VλVII 4A, VλII 2.1, VλVII 4A, a Vλ1 gene family member, a Vλ3gene family member, IGLV1S2, Vλ3-cML70, lalh2, lalvl, la3h3, Kv325, a VκI gene family member, κI-15A (KL012), VκII family member, a VκIII family member, a V$_κ$I gene family member, κI-15A (KL012), VκII A2 (optionally the A2a allele), VκA27 (Humkv325) and a gene segment at least 80% identical thereto; optionally each VL gene segment is selected from List A1, A2, A1.1, A1.2, A2.1, A2.2, A2.3 or A2.4 below;

(e) Optionally when (a)(ii) applies, the nucleotide sequence of the recombined region is identical to a nucleotide sequence produced by the recombination of a human J gene segment and optionally a human D gene segment with a human. VL gene segment selected from the group consisting of a VλII gene family member, VλVII 4A, VλII 2.1, VλVII 4A, a Vλ1 gene family member, a Vλ3gene family member, IGLV1S2, Vλ3-cML70, lalh2, lalyvl, la3h3, Kv325, a VκI gene family member, κI-15A (KL012), VκII family member, a VκIII family member, a VκI gene family member, κI-15A (KL012), VκII A2 (optionally the A2a allele), VκA27 (Humkv325) and a gene segment at least 80% identical thereto.

The group of VL gene segments is useful to bias the immune response of the vertebrate (and thus resultant lead antibodies) to a predetermined gene segment, eg, one known to be commonly used in natural human immune responses to antigens, such as antigens of infectious disease pathogens.

In an embodiment of the fourth configuration, the VL gene segments of the heavy chain locus are V$_λ$ gene segments.

In an embodiment of the fourth configuration, in (a) said constant region is a heavy chain endogenous non-human vertebrate (optionally host mouse or rat) constant region.

In an embodiment of the fourth configuration, in (b) said constant region is a light chain endogenous non-human vertebrate (optionally host mouse or rat) constant region.

In an embodiment of the fourth configuration, the genome of said vertebrate or cell is homozygous for heavy chain locus (a)(i) or (ii); optionally wherein:

the V gene segment repertoire of the heavy chain loci consists of one or more (or consists only of) human VL gene segments selected from the group consisting of a VL gene segment selected from the group consisting of a V$_λ$II gene family member, V$_λ$VII 4A, V$_λ$II 2.1, V$_λ$VII 4A, a V$_λ$1 gene family member, a V$_λ$3gene family member, IGLV1S2, V$_λ$3-cML70, lalh2, lalyvl, la3h3, Kv325, a VκI gene family member, κI-15A (KL012), V$_κ$II family member, a V$_κ$III family member, a VκI gene family member, κI-15A (KL012), V$_κ$II A2 (optionally the A2a allele), V$_κ$ A27 (Humkv325) and a gene segment at least 80% identical thereto; or the recombined VJ or VDJ repertoire of the heavy chain loci consists of sequences identical to one or more nucleotide sequences produced by the recombination of a human VL gene segment selected from the group consisting of a VL gene segment selected from the group consisting of a VλII gene family member, VλVII 4A, VλII 2.1, VλVII 4A, a Vλ1 gene family member, a Vλ3gene family member, IGLV1S2, Vλ3-cML70, lalh2, lalyvl, la3h3, Kv325, a VκI gene family member, id-15A (KL012), VκII family member, a VκIII family member, a VκI gene family member, κI-15A (KL012), VκII A2 (optionally the A2a allele), VκA27 (Humkv325) and a gene segment at least 80% identical thereto with a human J gene segment and optionally a human D gene segment.

In an embodiment of the fourth configuration, endogenous heavy and light chain expression has been inactivated, and wherein heavy chain loci according to the fourth configuration are the only functional heavy chain loci in the genome of the vertebrate or cell.

In an embodiment of the fourth configuration, each immunoglobulin heavy chain locus of said vertebrate or cell is according to (a)(i) and comprises only a single human VL gene segment selected from the group consisting of a VL gene segment selected from the group consisting of a VλII gene family member, VλVII 4A, VλII 2.1, VλVII 4A, a Vλ1 gene family member, a Vλ3gene family member, IGLV1S2, Vλ3-cML70, lalh2, lalyvl, la3h3, Kv325, a VκI gene family member, κI-15A (KL012), VκII family member, a VκIII family member, a VκI gene family member, κI-15A (KL012), VκII A2 (optionally the Ata allele), VκA27 (Humkv325) and a gene segment at least 80% identical thereto, optionally wherein the genome of the vertebrate or cell is homozygous for said heavy chain so that all heavy chain loci comprise the same, single human VL gene segment.

In an embodiment of the fourth configuration, each immunoglobulin heavy chain locus of said vertebrate or cell is according to (a)(ii) and comprises only a single rearranged VJ or VDJ region, optionally wherein the genome of the vertebrate or cell is homozygous for said heavy chain so that all heavy chain loci comprise the same, single rearranged V1 or Val region.

In an embodiment of the fourth configuration, each immunoglobulin heavy chain locus further comprises a VL gene segment or rearranged region that is a mutant respectively of said selected human VL gene segment or rearranged region, optionally wherein the genome of the vertebrate or cell is homozygous for said light chain mutant VL gene segment or rearranged region.

In all configurations, aspects, examples and embodiments of the invention, where a "mutant" is mentioned, this includes a mutant sequence that is identical to a reference sequence (eg, reference VH, VL, VJ or VDJ) but with 1, 2, 3, 4, 5, 6, 7, 8, 9 or 10 nucleotide or amino acid changes therefrom.

In an embodiment of the fourth configuration, each immunoglobulin heavy chain locus comprises only two or three human VL gene segments selected from said group, optionally wherein the genome of the vertebrate or cell is homozygous for said two or three heavy chain human VL gene segments.

In an embodiment of the fourth configuration, each immunoglobulin heavy chain locus comprises only two or three of said rearranged VJ or VDJ regions, optionally wherein the genome of the vertebrate or cell is homozygous for said two or three heavy chain rearranged VJ or VDJ regions.

The invention provides a monoclonal or polyclonal antibody composition prepared by immunisation of at least one vertebrate (eg, mouse or rat) according to the third or fourth embodiment of the invention with an antigen, optionally wherein the antigen is an antigen of an infectious disease pathogen, optionally wherein the same antigen is used to immunise all the vertebrates; optionally wherein the antibody or antibodies are IgG-type.

The invention provides a third method: A method of isolating an antibody (eg, IgG-type, such as IgG1) that binds a predetermined antigen, the method comprising
(a) providing a vertebrate (optionally a mouse or rat) according to the third or fourth embodiment of the invention;
(b) immunising (eg, using standard prime-boost) said vertebrate with said antigen (optionally wherein the antigen is an antigen of an infectious disease pathogen);
(c) removing B lymphocytes from the vertebrate and selecting one or more B lymphocytes expressing antibodies that bind to the antigen;
(d) optionally immortalising said selected B lymphocytes or progeny thereof, optionally by producing hybridomas therefrom; and
(e) isolating an antibody (eg, and IgG-type antibody) expressed by the B lymphocytes;
(f) Optionally, the third method comprises the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

Optionally, the third method further comprises making a mutant or derivative of the antibody.

The Invention Provides a Fourth Method:

A method of producing a polyclonal antibody mixture, the method comprising carrying out the third method by separately immunising first and second vertebrates (optionally first and second mice or first and second rats) with antigen (eg, any antigen disclosed herein) and combining the anti-antigen antibodies isolated from each vertebrate (or mutants or derivatives of said antibodies) to produce a polyclonal antibody mixture; optionally wherein the following apply separately or in combination ((i) and (ii); or (i) and (iii)):
(i) the vertebrates are immunised with the same antigen or different antigens (optionally wherein the different antigens are expressed by the same pathogenic organism (or different family members thereof or different strains of the organism));
(ii) prior to immunisation the heavy chain loci of the vertebrates contain the identical VL gene repertoire (optionally a single VL gene) and optionally the identical D and/or J repertoire; optionally the heavy chain loci of the mammals are identical prior to immunisation;
(iii) prior to immunisation the heavy chain loci of the vertebrates contain the identical rearranged VJ or VDJ repertoire (optionally a single VJ or VDJ); optionally the heavy chain loci of the vertebrates are identical prior to immunisation.

The Invention Provides a Fifth Method:

A method of producing a polyclonal antibody mixture, the method comprising carrying out the third method by immunising one or a plurality of vertebrates (optionally mice or rats) with first and second antigens and combining the anti-antigen antibodies isolated from each vertebrate (or mutants or derivatives of said antibodies) to produce a polyclonal antibody mixture; optionally wherein the following apply separately or in combination ((i) and (ii); or (i) and (iii)):
(i) the antigens are expressed by the same pathogenic organism (or different family members thereof or different strains of the organism);
(ii) prior to immunisation the heavy chain loci of the vertebrates contain the identical VL gene repertoire (optionally a single VL gene) and optionally the identical D and/or J repertoire; optionally the heavy chain loci of the mammals are identical prior to immunisation;
(iii) prior to immunisation the heavy chain loci of the vertebrates contain the identical rearranged VJ or VDJ repertoire (optionally a single VJ or VDJ); optionally the heavy chain loci of the vertebrates are identical prior to immunisation.

The Invention Provides a Sixth Method:

A method of producing host cells capable of expressing a polyclonal antibody mixture, the method comprising, in the third method wherein step (f) is carried out:—
(a) immunising one or a plurality of vertebrates (optionally mice or rats) with first and second antigens (optionally wherein the different antigens are expressed by the same pathogenic organism (or a family member thereof));
(b) isolating nucleic acid encoding first and second anti-antigen antibodies from B lymphocytes from said vertebrates;
(c) determining the nucleotide sequences of the heavy and light chain variable regions (optionally the entire heavy and/or light chain sequences) of the first antibody;
(d) determining the nucleotide sequence of the light variable region and optionally the heavy chain variable region of the second antibody;
(e) inserting the light chain variable region coding sequence of each antibody into a light chain expression vector; optionally wherein the constant region coding sequence of each light chain is exchanged for a nucleotide sequence that encodes a human or humanised constant region;
(f) inserting the heavy chain variable region coding sequence of the first antibody into a heavy chain expression vector; optionally wherein the constant region coding sequence of the heavy chain of the first antibody is exchanged for a nucleotide sequence that encodes a human or humanised constant region;
(g) optionally inserting the heavy chain variable region coding sequence of the second antibody into a heavy chain expression vector; optionally wherein the constant region coding sequence of the heavy chain of the second antibody is exchanged for a nucleotide sequence that encodes a human or humanised constant region; and
(h) introducing each expression vector into a host cell and co-expressing antibody chains in a mixture of said host cells to produce antibodies, each antibody comprising one or both of said light chain variable regions and a heavy chain; optionally wherein the expression vectors are introduced together into the same host cell (eg, a CHO or HEK293 cell) so that the cell is capable of expressing antibody light chains and heavy chains, such that the cell or a plurality of the host cells express antibodies (eg, two, three or four different antibodies), each comprising one or both of said light chain variable regions and a heavy chain;

(i) optionally:

prior to immunisation the heavy chain loci of the vertebrates contain the identical VL gene repertoire (optionally a single VL gene segment) and optionally the identical D and/or J repertoire (optionally a single D and J gene segment); optionally the heavy chain loci of the vertebrates are identical prior to immunisation; or prior to immunisation the heavy chain loci of the vertebrates contain the identical rearranged VJ or VDJ repertoire (optionally a single VJ or VDJ); optionally the heavy chain loci of the vertebrates are identical prior to immunisation.

The invention also provides a monoclonal or polyclonal antibody mixture so produced or a derivative antibody or mixture thereof, eg, where one or more constant region has been changed (eg, replaced with a different constant region such as a human constant region; or mutated to enhance or ablate Fc effector function).

The Invention Provides a Seventh Method:

A method of producing a monoclonal antibody or polyclonal antibody mixture, the method comprising carrying out the sixth method and expressing a monoclonal antibody or polyclonal mixture of said antibodies; optionally followed by isolating an antibody comprising the light chain variable region of the first and/or second antibodies.

Optionally, each vertebrate used for immunisation is provided by (a) isolating from a human blood or tissue (eg, B lymphocytes, PBMCs, bone marrow, spleen, tonsil or lymph node) sample a B lymphocyte that expresses an antibody that binds a predetermined antigen (eg, an antigen expressed by an infectious disease pathogen; optionally wherein said serum or tissue was from a human individual suffering, susceptible to, or recovered from, a disease or condition caused or mediated by an organism harbouring or secreting said antigen; or from a human individual harbouring said organism);

(b) determining which human germline VL gene segment was recombined in the human to produce the nucleotide sequence of said B lymphocyte that encodes the light chain variable region of the antibody;

(c) constructing a transgenic vertebrate wherein said human germline VL gene segment is provided in a heavy chain locus thereof according to the third or fourth configuration of the invention; and (d) providing said transgenic vertebrate for immunisation in the fourth, fifth or sixth method of the invention.

In another embodiment, each vertebrate used for immunisation is provided by (a) isolating from a human blood or tissue (eg, B lymphocytes, PBMCs, bone marrow, spleen, tonsil or lymph node) sample a B lymphocyte that expresses an antibody that binds a predetermined antigen (eg, an antigen expressed by an infectious disease pathogen; optionally wherein said serum or tissue was from a human individual suffering, susceptible to, or recovered from, a disease or condition caused or mediated by an organism harbouring or secreting said antigen; or from a human individual harbouring said organism);

(b) determining a nucleotide sequence of said B lymphocyte that encodes a rearranged VDJ or VJ region of the antibody;

(c) constructing a transgenic vertebrate wherein said rearranged VDJ or VJ region is provided in a heavy chain locus thereof according to the third or fourth configuration of the invention; and (d) providing said transgenic vertebrate for immunisation in the method of the fourth, fifth or sixth method of the invention.

Common Heavy Chain Antibodies & Bispecifics (eg, to Two Pathogen Antigens for Infectious Diseases)

The invention provides an isolated antibody (eg, IgG-type antibody) obtainable or obtained by the seventh method, or a mutant or derivative antibody thereof wherein (i) the isolated antibody comprises two copies of the heavy chain variable region of said first antibody paired with two copies of the light chain variable region of said first antibody; or (ii) the isolated antibody comprises two copies of the heavy chain variable region of said second antibody paired with two copies of the light chain variable region of said first antibody; or (iii) the isolated antibody is a bispecific antibody comprising one copy of the heavy chain variable region of said first antibody paired with a copy of the light chain variable region of the first antibody, and one copy of the heavy chain variable region of said the antibody paired with a copy of the light chain variable region of the first antibody, optionally wherein the bispecific antibody binds to said first and second antigens described above; optionally for use in medicine, optionally for the treatment and/or prevention of an infectious disease.

The invention provides a monoclonal or polyclonal antibody mixture (eg, IgG-type antibody or antibodies), wherein the monoclonal antibody or mixture comprises or consists of antibodies produced by the fourth, fifth, sixth or seventh method, or a mutant or derivative antibody thereof optionally for use in medicine, optionally for the treatment and/or prevention of an infectious disease, wherein optionally wherein each antibody binds an antigen of an infectious disease pathogen, preferably the same antigen.

The following embodiments relate to antibodies, host cells, nucleic acids and compositions and apply to such elements obtained or obtainable by any previous configuration or method of the invention:—

The invention provides an isolated chimaeric antibody for treating and/or preventing an infectious disease or condition, the antibody comprising a non-human vertebrate (optionally a mouse or rat) heavy chain constant regions and human variable regions that bind an antigen of an infectious disease pathogen, wherein the antibody is obtainable or obtained in a method comprising immunisation of a vertebrate according to of any one of the first to seventh methods of the invention with said antigen. The antigen is, for example, any antigen mentioned above. The disease or condition is, for example, any disease or condition mentioned above.

The invention provides an isolated human antibody for treating and/or preventing an infectious disease or condition, the antibody comprising human heavy chain constant regions and human variable regions that bind an antigen of an infectious disease pathogen, wherein the antibody is obtainable or obtained in a method comprising affinity maturation of antibody variable regions in vivo in a transgenic non-human vertebrate (eg, mouse or rat) when said variable regions are operably linked to heavy chain constant regions of said vertebrate (eg, mouse or rat heavy chain constant regions) by (a) immunisation of a vertebrate of any configuration of the invention with said antigen, (b) isolation of nucleic acid encoding a chimaeric antibody as described above, (c) replacing the nucleotide sequences of the nucleic acid that encode the non-human vertebrate heavy chain constant regions with nucleotide sequence encoding human heavy chain constant regions to produce nucleic acid encoding a human antibody; (d) expressing the human antibody in vitro (optionally from CHO or HEK293 cells harbouring the human nucleic acid) and (e) isolating the human antibody (optionally with further affinity maturation of the antibody and/or producing a derivative thereof). The invention provides a mixture of first and second such human antibodies (an optionally also third and optionally fourth antibodies), each antibody being capable of binding to an antigen of an infectious disease pathogen (optionally wherein the first antibody binds a first antigen and the second antibody binds a second antigen, said antigens being from the same pathogen; or wherein the antigens are the same). Optionally, the light chain amino acid sequence of the first antibody is identical to the light chain amino acid sequence of the second antibody, or has up to 15 amino acid changes therefrom. The advantages of such a common (or closely-related) chain are explained above, and include relative ease of manufacture.

The antigen is, for example, any antigen mentioned above. The disease or condition is, for example, any disease or condition mentioned above. The pathogen is, for example, any pathogen mentioned above.

The invention provides an antibody comprising human variable domains that bind a predetermined antigen (eg, an antigen expressed by a bacterial or viral pathogen), wherein the variable domain sequences are encoded by rearranged VDJ and VJ regions, each of the VDJ and/or VJ being a hybrid region produced by the in vivo rearrangement of human heavy and light chain variable region gene segments (V and J and optionally D segments); optionally wherein the antibody comprises human constant regions.

The invention provides a method of producing an isolated human antibody for treating and/or preventing an infectious disease or condition, the antibody comprising human heavy chain constant regions and human variable regions that bind an antigen of an infectious disease pathogen, wherein the method comprises affinity maturing antibody variable regions in vivo in a transgenic non-human vertebrate (eg, mouse or rat) when said variable regions are operably linked to heavy chain constant regions of said vertebrate (eg, mouse or rat heavy chain constant regions) by (a) immunisation of a vertebrate of any configuration of the invention with said antigen, (b) isolation of nucleic acid encoding a chimaeric antibody as described above, (c) replacing the nucleotide sequences of the nucleic acid that encode the non-human vertebrate heavy chain constant regions with nucleotide sequence encoding human heavy chain constant regions to produce nucleic acid encoding a human antibody; (d) expressing the human antibody in vitro (optionally from CHO or HEK293 cells harbouring the human nucleic acid) and (e) isolating the human antibody (optionally with further affinity maturation of the antibody and/or producing a derivative thereof). The antigen is, for example, any antigen mentioned above. The disease or condition is, for example, any disease or condition mentioned above. The pathogen is, for example, any pathogen mentioned above.

The invention provides the use of any isolated, monoclonal or polyclonal antibody or mixture of the invention as described above, in the manufacture of a medicament for the treatment and/or prevention of an infectious disease, optionally wherein the infectious disease is a disease caused by a bacterial or viral pathogen. The disease or condition is, for example, any disease or condition mentioned above. The pathogen is, for example, any pathogen mentioned above. For example, the infectious disease is selected from the group consisting of a disease caused by a pathogen selected from the group consisting of *Haemophilus influenza, E. coli, Neisseria meningitidis*, a herpes family virus, cytomegalovirus (CMV), HIV and influenza virus.

The invention provides first and second nucleotide sequences (eg, DNA, RNA, mRNA, cDNA) encoding the heavy and light chains of an antibody according to any configuration, aspect, example or embodiment of the invention or at least the variable regions thereof, optionally wherein each nucleotide sequence is part of a vector.

The invention provides a host cell comprising one or more expression vectors encoding the heavy chains of the first and second antibodies mentioned above, and the light chain of the first antibody mentioned above (and optionally also the light chain of the second antibody). Again, reference is made to the discussion above about the advantages of having a common antibody chain for the production of antibody mixtures.

The invention provides a pharmaceutical composition comprising the antibody or antibodies of any configuration, aspect, example or embodiment of the invention and a diluent, excipient or carrier; optionally wherein the composition is provided in a container connected to an IV needle or syringe or in an IV bag. The skilled person will know standard diluents, excipients and carriers suitable for pharmaceutical application.

Throughout this description, where it is mentioned "at least 80% identical", there is contemplated in the alternative one of the following identities: at least 85%, 90, 95, 96, 97, 98 or 99 identical and the disclosure herein contemplates that one or more of these identities may be recited in a claim herein in place of "at least 80% identical".

Tailoring V(D)J Incorporation into Immunoglobin Loci for the Generation of Antibodies Against Infectious Disease In the various configurations, aspects, embodiments and examples above, the invention provides the skilled addressee with the possibility of choosing immunoglobulin gene segments in a way that tailors or biases the repertoire for application to generating antibodies to treat and/or prevent infectious diseases. The inventors have categorised the following groups of gene segments for use in the invention according to the desired application of resultant antibodies.

List A:
Immunoglobulin Gene Segments for Antibodies that Bind an Antigen Expressed by a Pathogen
(a) a VL gene segment selected from the group consisting of a $V_\lambda II$ gene family member, $V_\lambda VII$ 4A, $V_\lambda II$ 2.1, $V_\lambda VII$ 4A, a $V_\lambda 1$ gene family member, a $V_\lambda 3$ gene family member, IGLV1S2, $V_\lambda 3$-cML70, lalh2, lalyvl, la3h3, Kv325, a VκI gene family member, κI-15A (KL012), $V_\kappa II$ family member, a $V_\kappa III$ family member, a VκI gene family member, κI-15A (KL012), $V_\kappa II$ A2 (optionally the A2a allele), $V_\kappa$ A27 (Humkv325) and a gene segment at least 80% identical thereto.
(b) a $V_\lambda$ gene segment selected from a $V_\lambda II$ gene family member, $V_\lambda VII$ 4A, $V_\lambda II$ 2.1, $V_\lambda VII$ 4A, a $V_\lambda 1$ gene family member, a $V_\lambda 3$ gene family member, IGLV1S2, $V_\lambda 3$-cML70, lalh2, lalyvl, la3h3 and a gene segment at least 80% identical thereto.
(c) a $V_\kappa$ gene segment selected from Kv325, a VκI gene family member, κI-15A (KL012), $V_\kappa II$ family member, a $V_\kappa III$ family member, a VκI gene family member, κI-15A (KL012), $V_\kappa$II A2 (optionally the A2a allele), $V_\kappa$ A27 (Humkv325) and a gene segment at least 80% identical thereto.

(d) a $V_H$ gene segment a $V_H$III gene family member (optionally, a VHIIIa or VHIIIb family member), a $V_H$IV gene family member, $V_H$III 9.1 (VH3-15), $V_H$III VH26 (VH3-23), $V_H$3-21, LSG6.1, LSG12.1, DP77 (V3-21), $V_H$ H11, VH1GRR, ha3h2, $V_H$I-ha1c1, $V_H$III-VH2-1, VH4.18, ha4h3, Hv1051, 71-2, Hv1f10, VH4.11, 71-4, VH251, VH1-69 and a gene segment at least 80% identical thereto.

(e) a $J_\lambda$ gene segment selected from $J_\lambda2$, $J_\lambda3$ and a gene segment at least 80% identical thereto.

(f) a D gene segment selected from Dk1, Dxp'1, Dn4r, D2r and a gene segment at least 80% identical thereto.

List A1:
Immunoglobulin Gene Segments for Antibodies that Bind an Antigen Expressed by a Bacterial Pathogen (a) a $V_\lambda$ gene segment selected from a $V_\lambda$II gene family member, $V_\lambda$VII 4A, $V_\lambda$II 2.1, $V_\lambda$VII 4A and a gene segment at least 80% identical thereto.

(b) a $V_\kappa$ gene segment selected from a V$\kappa$I gene family member, $\kappa$I-15A (KL012), $V_\kappa$II family member, a $V_\kappa$III family member, a V$\kappa$I gene family member, $\kappa$I-15A (KL012), $V_\kappa$II A2 (optionally the Ata allele), $V_\kappa$ A27 (Humkv325) and a gene segment at least 80% identical thereto.

(c) a $V_H$ gene segment a VH3 gene family member (optionally, a VHIIIa or VHIIIb family member), $V_H$III 9.1 (VH3-15), $V_H$III VH26 (VH3-23), $V_H$3-21, LSG6.1, LSG12.1, DP77 (V3-21), $V_H$ H11 and a gene segment at least 80% identical thereto.

(d) a $J_\lambda$ gene segment selected from $J_\lambda2$, $J_\lambda3$ and a gene segment at least 80% identical thereto.

(e) a $J_\lambda$ gene segment selected from $J_H2$, $J_\lambda3$, $J_H4$ and a gene segment at least 80% identical thereto.

List A1.1:
Immunoglobulin Gene Segments for Antibodies that Bind an Antigen Expressed by *H. influenza*

(a) a $V_\lambda$ gene segment selected from a $V_\lambda$II gene family member, $V_\lambda$VII 4A, $V_\lambda$II 2.1, $V_\lambda$VII 4A and a gene segment at least 80% identical thereto.

(b) a $V_\kappa$ gene segment selected from a $V_\kappa$II family member, a $V_\kappa$III family member, a V$\kappa$I gene family member, $\kappa$I-15A (KL012), $V_\kappa$II A2 (optionally the Ata allele), $V_\kappa$ A27 (Humkv325) and a gene segment at least 80% identical thereto.

(c) a $V_H$ gene segment a VH3 gene family member (optionally, a VHIIIb family member), $V_H$III 9.1 (VH3-15), $V_H$III VH26 (VH3-23), $V_H$3-21, LSG6.1, LSG12.1, DP77 (V3-21) and a gene segment at least 80% identical thereto.

(d) a $J_\lambda$ gene segment selected from $J_\lambda2$, $J_\lambda3$ and a gene segment at least 80% identical thereto.

List A1.2:
Immunoglobulin Gene Segments for Antibodies that Bind an Antigen Expressed by *E. Coli* or *Neisseria meningitidis*

(a) a VH gene segment a VH3 gene family member (optionally a VHIIIa or VHIIIb member), $V_H$III 9.1 (VH3-15), $V_H$ H11, $V_H$III VH26 (VH3-23) a gene segment at least 80% identical thereto, eg, $V_H$III 9.1+$J_H$3; or $V_H$H11+$J_H$4; or $V_H$III VH26+$J_H$2.

(b) a $V_\kappa$ gene segment selected from a V$\kappa$I gene family member, $\kappa$I-15A (KL012) and a gene segment at least 80% identical thereto.

(c) a $V_\lambda$ gene segment selected from a $V_\lambda$II gene family member, $V_\lambda$II 2.1 and a gene segment at least 80% identical thereto.

(d) a JH gene segment selected from $J_H2$, $J_H3$, $J_R4$ and a gene segment at least 80% identical thereto.

A2:
Immunoglobulin Gene Segments for Antibodies that Bind an Antigen Expressed by a Viral Pathogen (a) a $V_H$ gene segment selected from a $V_H$III gene family member, a $V_H$IV gene family member, $V_H$III-VH26 (VH3-23), VH1GRR, ha3h2, $V_H$I-ha1c1, $V_H$III-VH2-1, VH4.18, ha4h3, Hv1051, 71-2, Hv1f10, VH4.11, 71-4, VH251, VH1-69 and a gene segment at least 80% identical thereto.

(b) a $V_\lambda$ gene segment selected from a $V_\lambda1$ gene family member, a $V_\lambda3$gene family member, IGLV1S2, $V_\lambda$3-cML70, lalh2, lalyvl, la3h3 and a gene segment at least 80% identical thereto.

(c) a Vk gene segment selected from Kv325 and a gene segment at least 80% identical thereto.

(d) a $J_H$ gene segment selected from $J_H3$, $J_H5$, $J_H6$ and a gene segment at least 80% identical thereto.

(e) a D gene segment selected from Dk1, Dxp'1, Dn4r, D2r and a gene segment at least 80% identical thereto.

(f) a JA gene segment selected from $J_\lambda2$, $J_\lambda3$ and a gene segment at least 80% identical thereto.

A2.1:
Immunoglobulin Gene Segments for Antibodies that Bind an Antigen Expressed by Herpes Virus Family (eg, VZV or HSV)

(a) a $V_H$ gene segment selected from a $V_H$III gene family member, a $V_H$IV gene family member, $V_H$III-VH26 (VH3-23), VH1GRR, ha3h2, $V_H$I-ha1c1, $V_H$III-VH2-1, VH4.18, ha4h3, and a gene segment at least 80% identical thereto.

(b) a $V_\lambda$ gene segment selected from a $V_\lambda1$ gene family member, a $V_\lambda3$gene family member, IGLV1S2, $V_\lambda$3-cML70, lalh2, lalyvl, la3h3 and a gene segment at least 80% identical thereto.

(c) a JH gene segment selected from $J_H3$, $J_H5$, $J_H6$ and a gene segment at least 80% identical thereto.

(d) a D gene segment selected from Dk1, Dxp'1, Dn4r, D2r and a gene segment at least 80% identical thereto.

(e) a $J_\lambda$ gene segment selected from $J_\lambda2$, $J_\lambda3$ and a gene segment at least 80% identical thereto.

A2.2:
Immunoglobulin Gene Segments for Antibodies that Bind an Antigen Expressed by CMV (a) a $V_H$ gene segment selected from Hv1051 and a gene segment at least 80% identical thereto.

(b) a Vk gene segment selected from Kv325 and a gene segment at least 80% identical thereto.

A2.3:
Immunoglobulin Gene Segments for Antibodies that Bind an Antigen Expressed by HIV (a) a $V_H$ gene segment selected from 71-2, Hv1f10, VH4.11, 71-4, VH251, VH1-69 and a gene segment at least 80% identical thereto.

A2.4:
Immunoglobulin Gene Segments for Antibodies that Bind an Antigen Expressed by Influenza Virus (a) a $V_H$ gene segment selected from VH1-69 and a gene segment at least 80% identical thereto.

Thus,

Where one wishes to generate an antibody or antibody mixture to treat and/or prevent an infectious disease, one or more V, D and/or or all J gene segments used in any configuration, aspect, method, example or embodiment of the invention can be selected from List A1. Thus, for example in (a) of the first configuration of the invention, the recited heavy chain V gene segment is selected from the VH gene segments in List A, optionally with a D in that list.

Where one wishes to generate an antibody or antibody mixture to treat and/or prevent an infectious disease caused or mediated by a bacterial pathogen, one or more or all V, D and/or J gene segments used in any configuration, aspect, method, example or embodiment of the invention can be selected from List A1.

Where one wishes to generate an antibody or antibody mixture to treat and/or prevent an infectious disease caused or mediated by a viral pathogen, one or more or all V, D and/or J gene segments used in any configuration, aspect, method, example or embodiment of the invention can be selected from List A2.

Where one wishes to generate an antibody or antibody mixture to treat and/or prevent an infectious disease caused or mediated by H. influenza, one or more or all V, D and/or J gene segments used in any configuration, aspect, method, example or embodiment of the invention can be selected from List A1.1.

Where one wishes to generate an antibody or antibody mixture to treat and/or prevent an infectious disease caused or mediated by E. Coli or Neisseria meningitidis, one or more or all V, D and/or J gene segments used in any configuration, aspect, method, example or embodiment of the invention can be selected from List A1.2.

Where one wishes to generate an antibody or antibody mixture to treat and/or prevent an infectious disease caused or mediated by Herpes Virus Family (eg, VZV or HSV), one or more or all V, D and/or J gene segments used in any configuration, aspect, method, example or embodiment of the invention can be selected from List A2.1.

Where one wishes to generate an antibody or antibody mixture to treat and/or prevent an infectious disease caused or mediated by CMV, one or more or all V, D and/or J gene segments used in any configuration, aspect, method, example or embodiment of the invention can be selected from List A2.2.

Where one wishes to generate an antibody or antibody mixture to treat and/or prevent an infectious disease caused or mediated by HIV, one or more or all V, D and/or J gene segments used in any configuration, aspect, method, example or embodiment of the invention can be selected from List A2.3.

Where one wishes to generate an antibody or antibody mixture to treat and/or prevent an infectious disease caused or mediated by Influenza Virus, one or more or all V, D and/or 1 gene segments used in any configuration, aspect, method, example or embodiment of the invention can be selected from List A2.4.

Optionally each VH segment in the locus of the invention is selected from List A1, A2, A1.1, A1.2, A2.1, A2.2, A2.3 or A2.4.

Optionally each VL segment in the locus of the invention is selected from List A1, A2, A1.1, A1.2, A2.1, A2.2, A2.3 or A2.4

Optionally each D segment in the locus of the invention is selected from List A1, A2, A1.1, A1.2, A2.1, A2.2, A2.3 or A2.4.

Optionally each $J_L$ segment in the locus of the invention is selected from List A1, A2, A1.1, A1.2, A2.1, A2.2, A2.3 or A2.4.

Long HCDR3 Binding Sites & Tailoring Gene Segments to Pathogens & Other Antigens This aspect of the invention relates to the development of vertebrates, cells, methods and antibodies with relatively long HCDR3 binding sites. There is also provided embodiments in which genomes and antibodies are tailored in terms of their gene segments usage to address infectious disease pathogen antigens or other antigens which are advantageously addressed with a longer HCDR3 length for binding or neutralisation. Antibodies may be raised in the vertebrates by immunisation with a non-pathogen target antigen, eg, an antigen bearing an epitope in a cleft requiring a long CDR for contact, or an antigen from a pathogen that causes or is implicated in harmful human disease or conditions. Examples are bacterial or viral pathogens and the target antigen may be a bacterial cell-surface antigen or a viral surface-exposed antigen (eg, coat protein). Additionally or alternatively, the antigen may be an antigen that is released (eg, secreted) from a pathogenic bacterium or virus. The invention is not limited to addressing pathogen antigens, but is also useful for addressing other antigens where a long CDR3 would be useful for binding (eg, an enzyme active site or receptor cleft).

Figure 1:
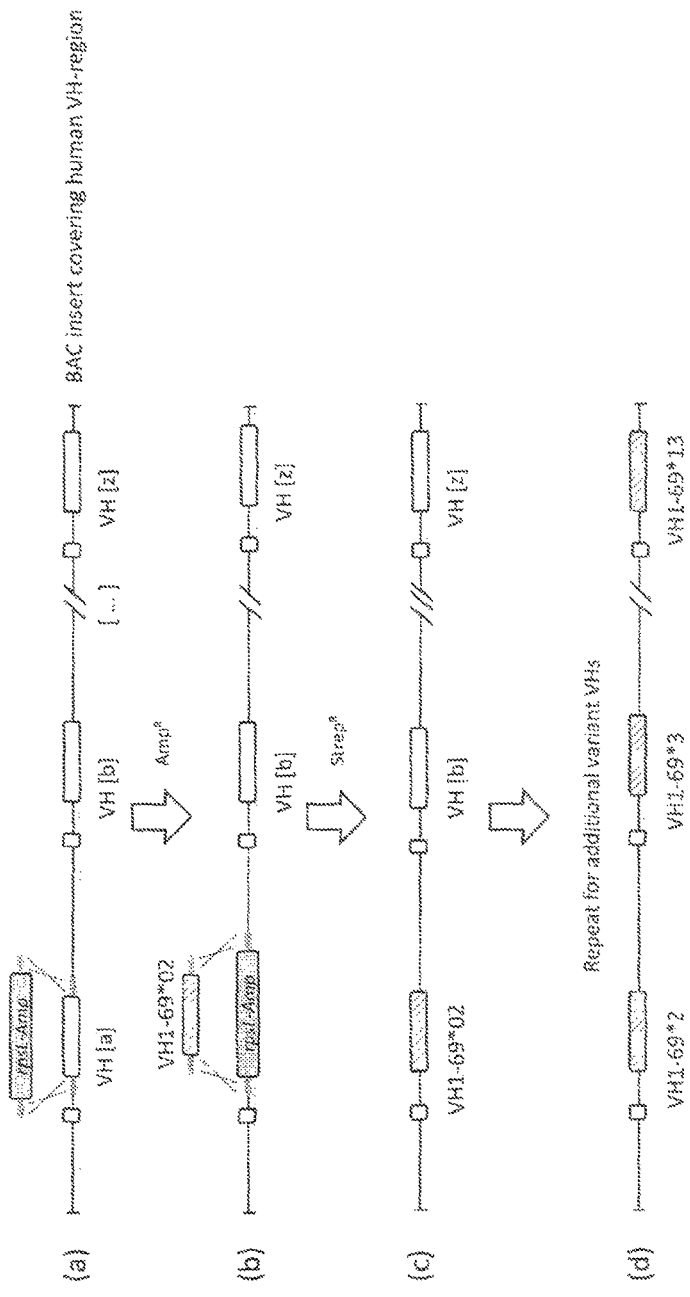
FIGS. 1 to 3: Schematic illustrating a protocol for producing recombineered BAC vectors to add V gene segments into a mouse genome.
Figure 2:
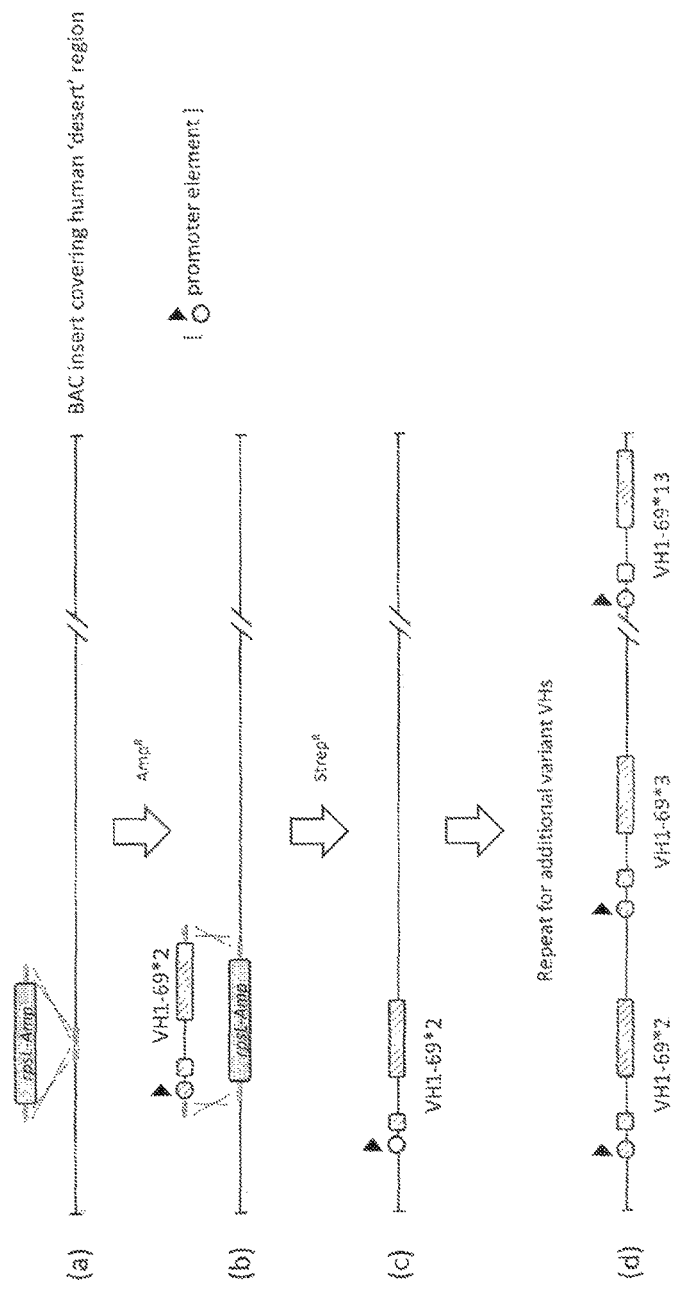

Antibodies with long HCDR3 (at least 20 amino acids according to IMGT nomenclature) have been shown to effectively neutralise a variety of pathogens including HIV, Influenza virus, malaria and Africa trypanosomes. Reference is also made to naturally-occurring Camelid (eg, llama or camel) heavy chain-only antibodies which bear long HCDR3s for reaching relatively inaccessible epitopes (see, eg, EP0937140). Long HCDR3s can form unique stable subdomains with extended loop structure that towers above the antibody surface to confer fine specificity. In some cases, the long HCDR3 itself is sufficient for epitope binding and neutralization (Liu, L et al; Journal of Virology. 2011. 85: 8467-8476, incorporated herein by reference). The unique structure of the long HCDR3 allows it to bind to cognate epitopes within inaccessible structure or extensive glycosylation on a pathogen surface. In human peripheral blood, there is around 3.5% of naïve B antibodies or 1.9% of memory B IgG antibodies containing the HCDR3s with lengths of more than 24 amino acids (Briney, B S et al, referenced given below) (FIG. 1 of Briney, B S et al). The usage analysis indicates that these antibodies have the preference to use human VH1-69, D2-2, D3-3, D2-15 and JH6 segments (FIGS. 2-5 of Briney, B S et al). There are around 20% of all HCDR3 length antibodies using JH6. However, in those antibodies with more than 24 amino acids of HCDR3, there are 70% using JH6 (FIG. 2 of Briney, B S et al). Human VH5-51 is also commonly used for anti-HIV antibodies (see Gorny et al, PLoS One. 2011; 6(12):e27780. Epub 2011 Dec. 2.

Human anti-V3 HIV-1 monoclonal antibodies encoded by the VH5-51/VL lambda genes define a conserved antigenic structure, incorporated herein by reference).

Supplementing these observations, the inventors have found (see examples) that other selected human heavy chain variable region gene segments (V, D, J) recombine in transgenic non-human vertebrates to produce long HCDR3 (at least 20 amino acids).

Thus, as explained further in the examples, the inventors constructed transgenic IgH loci in ES cells, wherein the loci purposely included selected human heavy chain variable region gene segments (V, D, J) that recombine to produce long HCDR3 (at least 20 amino acids). From the ES cells, the inventors generated transgenic non-human vertebrates (both naïve and immunised with a range of different target antigen types—disease pathogen and human antigenic species), isolated antibodies and heavy chain sequences based on the selected gene segments as well as B-cells expressing these and made hybridomas expressing antigen-specific antibodies that are based on the selected gene segments.

There is a need in the art for genetically modified non-human animals that prefer to make human antibodies that have long HCDR3s, as well as antibodies that can be selected from such animals wherein the antibodies can address target epitopes more easily accessed by long HCDR3s. Long CDRH3 is also useful for penetrating highly glycan-covered epitope sites (eg, virus epitopes or any glycoprotein targets, eg, see Nature. 2011 Dec. 14; 480 (7377):324-5. doi: 10.1038/480324a; Vaccinology: "A sweet cleft in HIV's armour", Sattentau Q J, incorporated herein by reference), and the target antigen can comprise such a target epitope.

The present invention provides vertebrates that can artificially simulate those naturally-occurring human long HCDR3 antibodies, and can provide antibody, heavy chain and variable domain repertoires from which can be selected an antibody, heavy chain or variable domain having a long HCDR3 (eg, having a HCDR3 length of 20, 21, 22, 23, 24, 25, 26, 27, 28, 29, 30 or more amino acids (according to IMGT). The invention provides for the combination of human VH, D and J gene repertoires upstream of non-human vertebrate (eg, mouse or rat, eg, endogenous mouse or rat) constant region in heavy chain loci comprised by the vertebrate genomes. This enables the recombination, maturation and selection of the human gene segments in the context of endogenous or other non-vertebrate constant regions which enhances the development of good sized antibody, heavy chain and variable domain repertoires from which to select long HCDR3-type binding sites. Thus, in an example of any configuration of the invention, the human gene segments are provided in a heavy chain locus upstream of a non-human vertebrate (eg, endogenous) constant region. Similarly any antibody of the invention comprises human variable domains and non-human vertebrate (eg, endogenous) domains. The latter can be replaced by human constant domains after selection and isolation.

For example, the following antibodies of the invention are contemplated (eg, produced in a vertebrate of this aspect of the invention by a method disclosed herein) or a copy or derivative of an antibody so produced:—

An isolated, synthetic or recombinant antibody comprising human heavy chain variable domains having a HCDR3 length of 20, 21, 22, 23, 24, 25, 26, 27, 28, 29, 30 or more amino acids (according to IMGT), the heavy chain variable domains being derived from the recombination of a human VH gene segment selected from a VH group disclosed herein with a human D gene segment and a human JH gene segment (optionally a JH6), wherein the antibody binds a target antigen; wherein the heavy chain variable domains have non-human vertebrate AID-pattern somatic hypermutations, (eg, mouse or rat AID-pattern mutations) when compared to corresponding human germline V, D and J sequences and/or non-human (eg, mouse or rat) terminal deoxynucleotidyl transferase (TdT)-pattern junctional mutations when compared to corresponding human germline V, D and J sequences. In an example, the antibody of the invention has a HCDR3 length of 20, 21, 22, 23, 24, 25, 26, 27, 28, 29 or 30 amino acids (according to IMGT). In an example, the antigen is an antigen of a pathogen that causes or is implicated in a human infectious disease or condition, eg, a pathogen listed in Table 1. In an example, the antibody specifically binds an active site or cleft of an antigen (eg, an enzyme active site or receptor cleft). This can be determined, eg, using standard X-ray crystallography of a complex of the antibody (or heavy chain or VH domain) with the cognate antigen, as is known to the skilled person.

Mouse AID-pattern somatic hypermutations and/or mouse dTd-pattern mutations can be provided, for example, wherein VH domain is produced in a mouse comprising mouse AID and/or mouse TdT (eg, endogenous AID or TdT). See also Annu. Rev. Biochem. 2007. 76:1-22; Javier M. Di Noia and Michael S, Neuberger, "Molecular Mechanisms of Antibody Somatic Hypermutation" (in particular FIG. 1 and associated discussion on AID hotspots in mouse); and Curr Opin Immunol. 1995 April; 7(2):248-54, "Somatic hypermutation", Neuberger M S and Milstein C (in particular, discussion on hotspots in mouse), the disclosures of which are incorporated herein by reference. Such mice can be made using corresponding mouse ES cell technology.

In an example, the antibody specifically binds to a HIV antigen. Several naturally-occurring human antibodies are known to be neutralising of HIV and have rather long HCDR3 lengths (20 amino acids or more according to IMGT; see Breden et al, PLoS One. 2011 Mar. 30; 6(3): e16857; "Comparison of antibody repertoires produced by HIV-1 infection, other chronic and acute infections, and systemic autoimmune disease" (incorporated herein by reference)—VH1-69 preferred for long HCDR3). See also PLoS One. 2012; 7(5):e36750. Epub 2012 May 9; "Human peripheral blood antibodies with long HCDR3s are established primarily at original recombination using a limited subset of germline genes"; Briney B S e al (incorporated herein by reference). Thus, it is desirable to provide antibodies of the invention that have similarly long HCDR3 lengths. The antibody of the invention is, in one example, provided for treating and/or preventing HIV infection, eg, chronic. HIV infection, in a human. The invention also provides a method of treating and/or preventing HIV infection, eg, chronic HIV infection, in a human, the method comprising administering a pharmaceutically acceptable dose of the antibody of the invention. The dose can be split into one or more administration aliquots, eg, administered over a time course according to a medically-determined regimen, as the skilled person will be able to determine.

In an example, the antibody specifically binds to *Hemophilus influenza* type b polysaccharide. The antibody of the invention is, in one example, provided for treating and/or preventing *Hemophilus influenza* infection, eg, chronic *Hemophilus influenza* infection, in a human. The invention also provides a method of treating and/or preventing *Hemophilus influenza* infection, eg, chronic *Hemophilus influenza* infection, in a human, the method comprising administering a pharmaceutically acceptable dose of the antibody of the invention. The dose can be split into one or more administration aliquots, eg, administered over a time course according to a medically-determined regimen, as the skilled person will be able to determine.

In an example, the antibody specifically binds to a rotavirus antigen (eg, protein 6 or 7). The antibody of the invention is, in one example, provided for treating and/or preventing rotavirus infection, eg, chronic rotavirus infection, in a human. The invention also provides a method of treating and/or preventing rotavirus infection, eg, chronic rotavirus infection, in a human, the method comprising administering a pharmaceutically acceptable dose of the antibody of the invention. The dose can be split into one or more administration aliquots, eg, administered over a time course according to a medically-determined regimen, as the skilled person will be able to determine.

In an example, the antibody specifically binds to a cytomegalovirus antigen (eg, cytomegalovirus gB antigen). The antibody of the invention is, in one example, provided for treating and/or preventing cytomegalovirus infection, eg, chronic cytomegalovirus infection, in a human. The invention also provides a method of treating and/or preventing cytomegalovirus infection, eg, chronic cytomegalovirus infection, in a human, the method comprising administering a pharmaceutically acceptable dose of the antibody of the invention. The dose can be split into one or more administration aliquots, eg, administered over a time course according to a medically-determined regimen, as the skilled person will be able to determine.

The invention also provides a vertebrate or cell for expressing such an antibody; thus the invention provides a non-human vertebrate (eg, a mouse or a rat) or a non-human vertebrate cell (eg, a mouse cell or a rat cell) whose genome comprises a human immunoglobulin VH gene segment repertoire that is biased to one, more or all human VH gene segments selected from a VH group disclosed herein.

The Invention Also Provides a method of isolating an antibody that binds a HIV antigen, *Hemophilus influenza* type b polysaccharide, cytomegalovirus antigen or rotavirus antigen, the method comprising (a) providing the human VH biased vertebrate of the invention;

(b) immunising said vertebrate with said HIV antigen, *Hemophilus influenza* type b polysaccharide, cytomegalovirus antigen or rotavirus antigen;

(c) removing B lymphocytes from the vertebrate and selecting one or more B lymphocytes expressing antibodies that bind to the antigen;

(d) optionally immortalising said selected B lymphocytes or progeny thereof, optionally by producing hybridomas therefrom; and (e) isolating an antibody (eg, and IgG-type antibody) expressed by the B lymphocytes, wherein the antibody has a HCDR3 length of 20 amino acids or more.

Optionally, the method further comprises the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

Optionally, the method further comprises making a copy, mutant or derivative (eg, humanised version) of the antibody produced by the method.

This aspect of the invention also provides

A pharmaceutical composition comprising the anti-HIV antibody, for treating and/or preventing HIV in a human (eg, an infant human).

A pharmaceutical composition comprising the anti-*Hemophilus influenza* type b polysaccharide antibody, for treating and/or preventing *Haemophilus influenza* in a human (eg, an infant human).

A pharmaceutical composition comprising the anti-rotavirus antibody, for treating and/or preventing rotavirus in a human (eg, an infant human).

A pharmaceutical composition comprising the anti-cytomegalovirus antibody, for treating and/or preventing cytomegalovirus in a human (eg, an infant human).

The invention also provides a method of generating such an antibody (eg, any one of embodiments (i) et seq above) by immunising a vertebrate of the invention with the target antigen and isolating the antibody from the vertebrate, optionally also making a copy or derivative of the antibody. In a further step, a B-cell capable of expressing the antibody is isolated from the vertebrate. In a further step, a nucleic acid encoding the antibody (or a VH domain thereof) is isolated from the vertebrate (eg, a nucleic acid PCR cloned from a B-cell isolated from the vertebrate).

In an example, the antibody of the invention is a neutralising antibody. In an example, the antibody of the invention has a HCDR3 length of 20, 21, 22, 23, 24, 25, 26, 27, 28, 29, 30 or more amino acids (according to IMGT). In an example, the antibody of the invention has a HCDR3 length of 20, 21, 22, 23, 24, 25, 26, 27, 28, 29 or 30 amino acids (according to IMGT). In an example, the antibody of the invention is isolated from a non-human vertebrate (eg, a mouse or a rat), for example a vertebrate of the invention; or the antibody is a copy or derivative (eg, humanised version) thereof. In an example, the antibody of the invention has non-human vertebrate constant regions (eg, mouse or rat constant regions); these may be replaced using standard recombinant DNA technology with human constant regions, so the invention also provides for human versions of the antibodies recited above, wherein the human antibody comprises human variable and constant regions, wherein the variable regions bind the antigen. In an example, the antibody of the has lambda-type human light chain variable domains. In another example, the antibody of the invention has kappa-type human light chain variable domains.

Antibody competition can be determined, for example, by ELISA or surface plasmon resonance (SPR; eg, by competition Biacore™ or Proteon) as is standard.

The invention also provides the following embodiments (recited below as numbered clauses):—

D Bias

1. A non-human vertebrate (eg, a mouse or a rat) or a non-human vertebrate cell (eg, a mouse cell or a rat cell) whose genome comprises a human immunoglobulin D gene segment repertoire that is biased to the human D2 and/or D3 family or biased to one, more or all human D gene segments selected from the group D1-26, D2-2, D3-9, D3-10, D3-22, D4-17, D6-13 and D6-19.

For example, the repertoire consists of only human D gene segments from the D2 and/or D3 family.

Optionally the repertoire is biased to one or more of human D2-2, D2-15, D3-3, D3-9, D3-10 and D3-22, or the repertoire consists of one, more or all of these D gene segments. These produce long HCDR3 lengths (eg, see Table 2 and references cited herein).

For example, the repertoire is biased to one or more of human of D2-2*02, D3-9*01, D3-10*01 and D3-22*01, or the repertoire consists of one, more or all of these D gene segments.

For example, the repertoire is biased to one or more of human D2-2*02, D3-9*01 and D3-10*01, or the repertoire consists of one, more or all of these D gene segments.

For example, the repertoire is biased to D3-9*01 and D3-10*01, or consists of one, more or all of these D gene segments.

Optionally the repertoire consists of one, more or all of human D1-26, D2-2, D3-9, D3-10, D3-22, D4-17, D6-13 and D6-19. These produce long HCDR3 lengths (eg, see Table 2).

Optionally the repertoire is biased to one or more of human D1-26*01, D2-2*02, D3-9*01, D3-10*01, D3-22*01, D4-17*01, D6-13*01 and D6-19*01, or the repertoire consists of one, more or all of these D gene segments.

Optionally the repertoire is biased to one or more of human D2-2, D3-9, D3-10, D3-22, D4-17, D6-13 and D6-19, or the repertoire consists of one, more or all of these D gene segments. Optionally the repertoire is biased to one or more of human D2-2*02, D3-9*01, D3-10*01, D3-22*01, D4-17*01, D6-13*01 and D6-19*01, or the repertoire consists of one, more or all of these D gene segments. These produce long HCDR3 lengths in naïve repertoires (eg, see Table 2).

Optionally the repertoire is biased to one or more of human D1-26, D2-2, D3-10 and D6-19, or the repertoire consists of one, more or all of these D gene segments. Optionally the repertoire is biased to one or more of human D1-26*01, D2-2*02, D3-10*01 and D6-19*01, or the repertoire consists of one, more or all of these D gene segments. These produce long HCDR3 lengths in immunised repertoires (eg, see Table 2).

Optionally the repertoire is biased to one or more of human D2-2, D3-9 and D3-10, or the repertoire consists of one, more or all of these D gene segments. Optionally the repertoire is biased to one or more of human D2-2*02, D3-9*01 and D3-10*01, or the repertoire consists of one, more or all of these D gene segments. These produce long HCDR3 lengths in antigen-specific repertoires (eg, see Table 2).

IMGT nomenclature is used for all gene segments.

Throughout this text, Genbank is a reference to Genbank release number 185.0 or 191.0; the 1000 Genomes database is Phase 1, release v3, 16 Mar. 2012; the Ensembl database is assembly GRCh37.p8 (Oct. 4, 2012); the IMGT database is available at www.imgt.org. The sequences of all VH gene segments explicitly mentioned herein are disclosed herein in their entirety (for possible inclusion in clauses in conjunction with any aspect of the invention as clauseed), such sequences being those in the IMGT and 1000 Genomes databases.

In one embodiment, the genome comprises an IgH locus comprising a targeted insertion of said human D gene segments. In an example, the IgH locus comprises (in 5' to 3' order) one or more human VH gene segments, said D gene segment repertoire, one or more human JH gene segments and a constant region (eg, wherein the constant region is a human constant region or a non-human (eg, endogenous, eg, mouse or rat) constant region).

In another embodiment, the genome comprises said human D gene segments randomly inserted therein. This can be effected, eg, by incorporating human DNA borne by YACS into the genome of ES cells (followed optionally by generation of a non-human vertebrate therefrom, as is standard).

Optionally, the human D gene segment repertoire further comprises no more than 5 additional human D gene segments, for example, the repertoire includes 1, 2, 3, 4 or 5 additional human D gene segments.

2. The vertebrate or cell of clause 1, wherein the D gene segment repertoire consists of or substantially consists of one, two or three human gene segments selected from the group D1-26, D2-2, D3-9, D3-10, D3-22, D4-17, D6-13 and D6-19.

3. The vertebrate or cell of clause 1 or 2, wherein the genome comprises an unrearranged immunoglobulin heavy chain locus comprising (in 5' to 3' order) human VH, D and JH gene segments and said human D gene segments recited in clause 1 are spaced from the VH gene segment(s) by no more than four other D gene segments (eg, by no D gene segments). This provides for bias wherein proximal D gene segments (those more 3', ie, closer to the constant region) are likely to be more frequently used than those segments from distal (ie, 5' or further away from the constant region).

4. The vertebrate or cell of any preceding clause, wherein the genome comprises an unrearranged immunoglobulin heavy chain locus comprising said human D gene segments and there are no other D gene segments in the locus between said human D gene segments.

This is another way of biasing the repertoire of D gene segments. Thus, the desired Ds are provided in tandem, aimed to promote use in recombination.

5. The vertebrate or cell of any preceding clause, wherein the genome comprises three or more copies of a human D gene segment selected from D1-26, D2-2, D2-15, D3-3, D3-9, D3-10, D3-22, D4-17, D6-13 and D6-19.

For example, the genome comprises three or more copies of a human D gene segment selected from D1-26, D2-2, D3-9, D3-10, D3-22, D4-17, D6-13 and D6-19.

This is another way of biasing the repertoire of D gene segments.

6. The vertebrate or cell of clause 5, wherein the genome comprises first and second human D gene segments selected from D1-26, D2-2, D2-15, D3-3, D3-9, D3-10, D3-22, D4-17, D6-13 and D6-19 when the first D gene segment is present as three or more copies and wherein the second D gene segment is present as three or more copies.

For example, the first and second gene segments are selected from D1-26, D2-2, D3-9, D3-10, D3-22, D4-17, D6-13 and D6-19.

The various gene segment biasing techniques described herein can be performed using conventional DNA manipulation in the construction of transgenic vertebrates or cells of the invention, which techniques (eg, recombineering and recombinant DNA technology) will be known to the skilled person. For example, BACs can be constructed using these techniques in which the desired combination of human gene segments is provided, and these BACs can be introduced into ES cells for incorporation of the human gene segments into the genomes thereof (eg, by targeted insertion into Ig loci). The ES cells can be used to generate transgenic vertebrates as is standard and cells (eg, B-cells) can be isolated from these wherein the genome is as per the invention.

In one embodiment, the biased D gene segment(s) are selected from the IMGT database of variants or the 1000 Genomes database.

7. The vertebrate or cell of any preceding clause, wherein the D gene segments are selected from D2-2*02, D3-9*01, D3-10*01 and D3-22*01, or selected from D1-26*01, D2-2*02, D3-9*01, D3-10*01, D3-22*01, D4-17*01, D6-13*01 and D6-19*01.

VH Bias

8. A non-human vertebrate (eg, a mouse or a rat) or a non-human vertebrate cell (eg, a mouse cell or a rat cell), optionally according to any preceding clause, whose genome comprises a human immunoglobulin VH gene segment repertoire that is biased to one, more or all of gene segments selected from the group VH1-2, VH1-3, VH1-8, VH1-18, VH5-51, VH1-69, VH2-5, VH3-7, VH3-9, VH3-11, VH3-13, VH3-20, VH3-21, VH3-23, VH4-4, VH6-1 and VH7-4-1.

These produce long HCDR3 lengths (see Table 2 and references cited herein).

For example, the VH repertoire is biased to one, more or all of VH1-2, VH1-3, VH1-8, VH1-18, VH2-5, VH3-7, VH3-9, VH3-11, VH3-13, VH3-20, VH3-21, VH3-23, VH4-4, VH6-1 and VH7-4-1. These produce long HCDR3 lengths (see Table 2), or the repertoire consists of one, more or all of these VH gene segments. For example, the VH repertoire is biased to one, more or all of VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01, or the repertoire consists of one, more or all of these VH gene segments.

For example, the VH repertoire is biased to one, more or all of VH1-2*02, VH1-8*01, VH1-18*01, VH1-3*01, VH2-5*10, VH3-7*01, VH3-9*01, VH3-13*01, VH3-21*03, VH3-23*04, VH4-4*02, VH6-1*01 and VH7-4-1*01, or the repertoire consists of one, more or all of these VH gene segments. These produce long HCDR3 lengths in naïve repertoires (see Table 2).

For example, the VH repertoire is biased to one, more or all of VH4-4*02, VH3-11*01 and VH3-7*01, or the repertoire consists of one, more or all of these VH gene segments. These produce long HCDR3 lengths in immunised repertoires (see Table 2).

For example, the VH repertoire is biased to one, more or all of VH1-3*01, VH1-8*01, VH3-7*01, VH3-9*01, VH3-11*01 and VH4-4*02, or the repertoire consists of one, more or all of these VH gene segments. These produce long HCDR3 lengths in antigen-specific repertoires (see Table 2).

Optionally, the human VH gene segment repertoire further comprises no more than 5 additional human VH gene segments, for example, the repertoire includes 1, 2, 3, 4 or 5 additional human VH gene segments.

In one embodiment, the genome comprises an IgH locus comprising a targeted insertion of said human VH gene segments. In an example, the IgH locus comprises (in 5' to 3' order) said VH gene segment repertoire, one or more human D gene segments, one or more human JH gene segments and a constant region (eg, wherein the constant region is a human constant region or a non-human (eg, endogenous, eg, mouse or rat) constant region).

In another embodiment, the genome comprises said human VH gene segments randomly inserted therein. This can be effected, eg, by incorporating human DNA borne by YACS into the genome of ES cells (followed optionally by generation of a non-human vertebrate therefrom, as is standard).

9. The vertebrate or cell of clause 8, wherein the VH gene segment repertoire substantially consists of or substantially consists of one, two or three human gene segments selected from VH1-2, VH1-3, VH1-8, VH1-18, VH5-51, VH1-69, VH2-5, VH3-7, VH3-9, VH3-11, VH3-13, VH3-20, VH3-21, VH3-23, VH4-4, VH6-1 and VH7-4-1.

For example, the VH gene segment repertoire substantially consists of or substantially consists of one, two or three human gene segments selected from the group consisting of VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01.

10. The vertebrate or cell of clause 8 or 9, wherein the genome comprises an unrearranged immunoglobulin heavy chain locus comprising (in 5' to 3' order) human VH, D and JH gene segments and said human VH gene segments are spaced from the D gene segment(s) by no more than four other VH gene segments (eg, by no VH gene segments).

This provides for bias wherein proximal VH gene segments (those more 3', ie, closer to the constant region) are likely to be more frequently used than those segments from distal (ie, 5' or further away from the constant region).

11. The vertebrate or cell of any one of clauses 8 to 10, wherein the genome comprises an unrearranged immunoglobulin heavy chain locus comprising said human VH gene segments and there are no other VH gene segments in the locus between said human VH gene segments.

This is another way of biasing the repertoire of VH gene segments.

12. The vertebrate or cell of any one of clauses 8 to 11, wherein the genome comprises three or more copies of a human VH gene segment selected from the group consisting of VH1-2, VH1-3, VH1-8, VH1-18, VH5-51, VH1-69, VH2-5, VH3-7, VH3-9, VH3-11, VH3-13, VH3-20, VH3-21, VH3-23, VH4-4, VH6-1 and VH7-4-1.

For example, the genome comprises three or more copies of a human VH gene segment selected from the group consisting of VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01.

This is another way of biasing the repertoire of VH gene segments.

13. The vertebrate or cell of clause 12, wherein the genome comprises first and second human VH gene segments selected from the group consisting of VH1-2, VH1-3, VH1-8, VH1-18, VH5-51, VH1-69, VH2-5, VH3-7, VH3-9, VH3-11, VH3-13, VH3-20, VH3-21, VH3-23, VH4-4, VH6-1 and VH7-4-1 when the first VH gene segment is present as three or more copies and wherein the second VH gene segment is present as three or more copies.

For example, the genome comprises first and second human VH gene segments selected from the group consisting of VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01 when the first VH gene segment is present as three or more copies and wherein the second VH gene segment is present as three or more copies.

In an embodiment, all or substantially all of VH gene segments are present as three or more copies each.

The various gene segment biasing techniques described herein can be performed using conventional DNA manipulation in the construction of transgenic vertebrates or cells of the invention, which techniques (eg, recombineering and recombinant DNA technology) will be known to the skilled person. For example, BACs can be constructed using these techniques in which the desired combination of human gene segments is provided, and these BACs can be introduced into ES cells for incorporation of the human gene segments into the genomes thereof (eg, by targeted insertion into Ig loci). The ES cells can be used to generate transgenic vertebrates as is standard and cells (eg, B-cells) can be isolated from these wherein the genome is as per the invention.

In one embodiment, the biased D gene segment(s) are selected from the IMGT database of variants or the 1000 Genomes database.

14. The vertebrate or cell of any one of clauses 8 to 13, wherein the VH gene segments are selected from the group consisting of VH1-2*02, VH1-3*01, VH1-8*01, VH1-18*01, VH2-5*10, VH3-7*01, VH3-9*01, VH3-

11*01, VH3-13*01, VH3-21*03, VH3-23*04, VH4-4*02, VH6-1*01 and VH7-4-1*01.

In an embodiment, the genome comprises a human immunoglobulin VH gene segment repertoire that is biased to VH1-69.

In an embodiment, the human immunoglobulin VH gene segment repertoire substantially consists of one or more human VH1-69 gene segments.

The gene segments are provided in one or more immunoglobulin loci. For example, the gene segment repertoire (D and/or VH) is provided in both IgH loci (ie, in a homozygous state).

15. The vertebrate or cell of any one of clauses 8 to 16, comprising an immunoglobulin heavy chain locus comprising two or more copies of a VH gene segment selected from said group.

Thus, at least one of said copies is closer to the constant region of the locus than the germline distance in a human from a human constant region. The aim is to provide by bias by providing more than one copy on the same locus. Also as at least one of the copies is closer (more proximal to) the constant region and J-C intron (which includes regulatory elements such as the Emu enhancer region), this may favour use of the gene segment, thus contributing to the desired bias.

Optionally, the genome is homozygous for the heavy chain locus.

Optionally the two or more copies of gene segments are identical (eg, all VH1-69*01, using IMGT nomenclature). In another example, copies are variants of each other, eg, naturally-occurring human variants. Alternatively, synthetic variants may be used with or without a naturally-occurring variant.

In any embodiment of the invention, the vertebrate is naïve or immunised with a target antigen.

16. The vertebrate or cell of any clause, wherein the genome comprises a human JH gene segment repertoire consisting of one or more human JH6 gene segments.

This biases the JH repertoire for the production of long HCDR3, since this is the longest naturally-occurring human JH gene segment type and is commonly found in naturally-occurring human antibodies having long HCDR3.

For example, the repertoire comprises two or more different JH6 variants. In an example, the repertoire comprises two or more JH6*02 variants (IMGT nomenclature).

17. The vertebrate or cell of any preceding clause, wherein the genome comprises a human immunoglobulin JH gene segment repertoire that is biased to JH6, optionally JH6*02.

18. The vertebrate or cell of clause 17, wherein the JH gene segment repertoire consists or substantially consists of three or more human JH6 gene segments.

19. The vertebrate or cell of any preceding clause, wherein the sequence of each of said human gene segments is a human germline gene segment sequence.

20. The vertebrate or cell of any preceding clause, wherein one, more or all of the selected gene segments are present in the genome as two or more copies, the copies being variants of each other.

Thus, one, more or all of the human V, D and JH gene segments of said genome is present in two or more variant versions, such as naturally-occurring human variants, eg, variants found in the 1000 Genomes database and/or IMGT database. In another example, one or more of the variants may be a synthetic variant.

21. The vertebrate or cell of any preceding clause, wherein said human gene segments are provided by homozygous immunoglobulin heavy chain loci.

In an example, no other (non-human) active heavy chain VH, D or JH gene segments are present in heavy chain loci of the genome. Additionally, in an example no active non-human light chain VL or JL gene segments are present in the genome.

This is useful for ensuring that endogenous (non-human) variable region expression is inactivated. Thus, all heavy chains produced by the vertebrate or cell will have human variable regions, which is useful for producing drugs for administration to humans.

22. A non-human vertebrate (eg, a mouse or a rat) or a non-human vertebrate cell (eg, a mouse cell or a rat cell) whose genome comprises a human immunoglobulin VH gene segment repertoire, one or more human D gene segments and one or more human JH gene segments, wherein the VH repertoire does not comprise one, more or all VH gene segments selected from the group VH1-2, VH1-3, VH1-8, VH1-18, VH5-51, VH1-69, VH2-5, VH3-7, VH3-9, VH3-11, VH3-13, VH3-20, VH3-21, VH3-23, VH4-4, VH6-1 and VH7-4-1.

23. A non-human vertebrate (eg, a mouse or a rat) or a non-human vertebrate cell (eg, a mouse cell or a rat cell) whose genome comprises a human immunoglobulin D gene segment repertoire, one or more human VH gene segments and one or more human JH gene segments, wherein the D repertoire does not comprise one, more or all D gene segments selected from the group D1-26, D2-2, D3-9, D3-10, D3-22, D4-17, D6-13 and D6-19.

In instances it has been observed in that the art that certain human gene usage may dominate the immune response to infectious disease pathogen antigens or other antigens. While this may yield many specific antibodies, typically these may not be neutralising and thus the immune response is relatively ineffective. This may happen, for example, where the antigen is a decoy antigen expressed by the pathogen. The present embodiments of the invention where specific gene segments are omitted are useful for avoiding dominance of certain human gene segments, such as those omitted from the genome. In this way, the genome human gene segment repertoire is biased away from the dominance and this enables better use and sampling of the remaining human gene segment sequence space, thereby providing the chance of producing antibodies that may not be normally raised in a natural setting. Antigen specific antibodies can be selected from vertebrates and cells with such genomes. In some examples, this may yield neutralising antibodies.

It is advantageous to include a plurality of different human VH gene segments, making up the human VH gene segment repertoire. This provides for good diversities of rearranged human variable regions from which to select leads. It is possible, for example, to include an otherwise complete, functional repertoire of human VH gene segments. To this end, the human VH gene segment repertoire comprises, in one example, a plurality of human VH gene segments, eg, at least 7, 10, 15, 20, 15, 30, 35, 40 or 45 different human VH gene segments. This can be achieved, for example, using BACs harbouring stretches of unrearranged human variable region DNA comprising VH gene segments—homologous recombination and/or sRMCE being used to insert several stretches of such DNA from serial BACs into an endogenous heavy chain locus upstream of the constant region thereof in the genome of a non-human vertebrate ES cell (eg, mouse or rat ES cell), followed by development of one or more progeny vertebrates from such cells (and optional breeding to homozygosity of the heavy chain locus). In one embodiment, human DNA is inserted that includes a first human VH (eg, VH1-69 and/or VH1-2) and flanking VH gene segments upstream and downstream of these. In a second ES cell genomic manipulation, the first VH is deleted from the genome, eg, using standard homolgous recombination techniques as is known in the art. In this way, one or more VH gene segments usually upstream and/or downstream of the deleted gene segment(s) in a wild-type human germline genome are retained so that they can be available to contribute to the subsequent rearranged human V region repertoire that is used for selection of leads. In another example, the initial insertion of human DNA is made using stretches of DNA that already omit the first VH (eg, by deleting such stretches using recombineering of BACs in *E. coli*, as is known in the art). Similar techniques can be used (with appropriate BACs) for the omission of human D and/or J gene segments.

Thus, in an embodiment, VH gene segments that normally are upstream and/or downstream of the omitted human VH gene segments (or omitted D or J as per other embodiments) in a wild-type germline human genome are included in the vertebrate or cell of the invention. For example, the human VH gene segment repertoire of the genome in the invention does not comprise VH1-69, but does comprise one, two, three or four human VH gene segments selected from VH2-10, VH3-72, VH3-73 and VH3-74. These are gene segments that are immediately upstream of VH1-69 in a wild-type human germline heavy chain locus (see IMGT). For example, additionally or alternatively the human VH gene segment repertoire of the genome in the invention does not comprise VH1-69, but does comprise one, two, three, four or more (or all of) human VH gene segments selected from VH3-66, VH3-64, VH4-61, VH4-59, VH1-58, VH3-53, VH3-49, VH3-48, VH1-46 and VH1-45. These are gene segments that are immediately downstream of VH1-69 in a wild-type human germline heavy chain locus (see IMGT). Additionally or alternatively, the human VH gene segment repertoire of the genome in the invention does not comprise VH1-69, but does comprise one, two, three, four or more (or all of) human VH gene segments selected from VH2-5, 7-41, 4-4, 1-3, 1-2 and 6-1. Additionally or alternatively, the human VH gene segment repertoire of the genome in the invention does not comprise VH1-69, but does comprise one, two, three, four, 5, 6, 7, 8, 9, 10 or more (or all of) human VH gene segments selected from VH2-5, 7-41, 4-4, 1-3, 1-2, 6-1, 3-7, 1-8, 3-9, 3-11 and 3-13. Additionally or alternatively, the human VH gene segment repertoire of the genome in the invention does not comprise VH1-69, but does comprise one, two, three, four, 5, 6, 7, 8, 9, 10, 11, 12, 13, 14, 15, 16, 17 or more (or all of) human VH gene segments selected from VH2-5, 7-41, 4-4, 1-3, 1-2, 6-1, 3-7, 1-8, 3-9, 3-11, 3-13, 3-15, 1-18, 3-20, 3-21, 3-23, 1-24 and 2-26. Additionally or alternatively, the human VH gene segment repertoire of the genome in the invention does not comprise VH1-69, but does comprise VH6-1 (which is commonly used in human immune responses, VH6-1 being the most proximal to the constant region in a wild-type human germline heavy chain locus) and/or VH3-23 (which is commonly used in human immune responses). In embodiment (eg, for generating VH, heavy chains or antibodies for treating and/or preventing an infectious disease, eg, HIV infection, in a human), VH1-2 is omitted in the genome or locus. In this case one, two, three or all human VH gene segments immediately 5' and 3' of VH1-2 in a wild-type germline human IgH locus (eg, see IMGT) are included in the genome, such as comprised by the same IgH locus upstream of human D and JH gene segments and a constant region.

24. The vertebrate or cell of clause 22 or 23, wherein the genome comprises a human JH gene segment repertoire that does not comprise JH6.

JH Bias

25. A non-human vertebrate (eg, a mouse or a rat) or a non-human vertebrate cell (eg, a mouse cell or a rat cell) whose genome comprises a human immunoglobulin JH gene segment repertoire that is biased to human JH6.

In an example, the repertoire is biased to human JH6*02 (IMGT nomenclature).

So, the inventors made a choice of human JH6*02 on the basis of (i) Containing YYG and YYGXDX motifs that is conserved across several vertebrate species;

(ii) Provision of one less TAC codon than other human JH6 variant (an AID hotspot that risks stop codons) and a choice instead of a codon that preserves the YYG and YYGXDX motifs;

(iii) Avoidance of a GGCA AID hotspot in the region of the HCDR3/FW4 junction; and (iv) Common occurrence (and thus conservation and acceptability) in humans of the JH6*02 variant.

26. The vertebrate or cell of clause 25, wherein the genome comprises an unrearranged immunoglobulin heavy chain locus comprising a plurality of human JH6 gene segments; optionally wherein the genome is homozygous for said locus.

In an example, the plurality comprises or consists of a plurality of JH6*02 gene segments.

27. The vertebrate or cell of clause 26, wherein the heavy chain locus comprises (in 5' to 3' order) human VH, D and JH gene segments and said JH6 gene segments are spaced from the D gene segment(s) by no more than two other JH gene segments.

28. The vertebrate or cell of clause 25, 26 or 27, wherein are no other JH gene segments in the locus between said human JH6 gene segments.

29. A non-human vertebrate (eg, a mouse or a rat) or a non-human vertebrate cell (eg, a mouse cell or a rat cell) whose genome comprises a human immunoglobulin JH gene segment repertoire that consists of one or more human JH6 gene segments.

In an example, all of the gene segments are JH6*02 gene segments.

30. The vertebrate or cell of any one of clauses 25 to 29, wherein all of said gene segments are human germline gene segments.

31. The vertebrate or cell of any one of clauses 25 to 30, comprising different variant JH6 gene segments.

In an example, the variants are all naturally-occurring (eg, appearing in the IMGT or 1000 Genome databases). In an other example, one or more variant is synthetic.

32. The vertebrate or cell of any one of clauses 25 to 31, wherein said gene segments are provided by homozygous immunoglobulin heavy chain loci.

In one embodiment, the biased JH gene segment(s) are selected from the IMGT database of variants or the 1000 Genomes database.

33. A monoclonal or polyclonal antibody composition or a population of antibody-producing cells for producing such composition, wherein the composition or population is prepared by immunising at least one vertebrate according to any preceding clause with an antigen, wherein the antibody or antibodies have human heavy chain variable regions comprising non-human vertebrate AID-pattern somatic hypermutations, (eg, mouse or rat AID-pattern mutations) when compared to corresponding human germline V, D and J sequences and/or non-human (eg, mouse or rat) terminal deoxynucleotidyl transferase (TdT)-pattern junctional mutations when compared to corresponding human germline V, D and J sequences; wherein the composition comprises at least one antigen-specific antibody having a HCDR3 length of at least 20 amino acids (according to IMGT).

As will be readily apparent to the skilled person, AID and TdT mutations can be determined using bioinformatics analysis to find the closest matching human germline gene segment(s) that correspond to a given variable domain sequence, aligning the sequences and determining the differences. AID has known hotspots for mutation (eg, see Annu. Rev. Biochem. 2007.76:1-22; Javier M. Di Noia and Michael S, Neuberger, "Molecular Mechanisms of Antibody Somatic Hypermutation" (in particular FIG. 1 and associated discussion on AID hotspots in mouse); and Curr Opin Immunol. 1995 April; 7(2):248-54, "Somatic hypermutation", Neuberger M S and Milstein C (in particular, discussion on hotspots in mouse), the disclosures of which are incorporated herein by reference). By carrying out the standard bioinformatics analysis, TdT mutations (eg, to provide junctional mutations and diversity) can be determined, as will be familiar to the skilled person.

Corresponding human germline V, D and J sequences can be according to the IMGT database or 1000 Genomes database, for example.

For example, the HCDR3 length is at least 20, 21, 22, 23, 24, 25, 26, 27, 28, 29 or 30 amino acids.

For example, the HCDR3 length is from 20 to 23 or 24 to 30, eg, from 28 to 30 amino acids.

For example, the cells are B cells (eg, immortalised B cells) or hybridomas.

Optionally the antibodies of any aspect of the invention comprise human light chain variable regions. For example, the human light chain variable regions have non-human vertebrate AID-pattern somatic hypermutations, (eg, mouse or rat AID-pattern mutations) when compared to corresponding human germline V, D and J sequences and/or non-human (eg, mouse or rat) terminal deoxynucleotidyl transferase (TdT)-pattern junctional mutations when compared to corresponding human germline V, D and J sequences.

34. An isolated antibody that specifically binds an antigen, the antibody comprising human heavy chain variable regions and non-human constant regions, wherein the variable regions are derived from the recombination in a non-human vertebrate of (i) a human VH gene segment selected from the group recited in clause 8 with (ii) a human D gene segment selected from the group recited in clause 1 and with a human JH gene segment (optionally JH6); wherein the antibody has a HCDR3 length of at least 20 amino acids (according to IMGT); and non-human vertebrate AID-pattern somatic hypermutations, (eg, mouse or rat AID-pattern mutations) when compared to corresponding human germline V, D and J sequences and/or non-human (eg, mouse or rat) terminal deoxynucleotidyl transferase (TdT)-pattern junctional mutations when compared to corresponding human germline V, D and J sequences.

In examples, the VH is selected from the group VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01 and/or
the D is selected from the group
D2-2*02, D3-9*01, D3-10*01 and D3-22*01, or
D2-2*02, D3-9*01 and D3-10*01, or
D3-9*01 and D3-10*01, or
D1-26, D2-2, D3-9, D3-10, D3-22, D4-17, D6-13 and 06-19, or
D1-26*01, D2-2*02, D3-9*01, D3-10*01, D3-22*01, D4-17*01, D6-13*01 and D6-19*01, or
D2-2, D3-9, D3-10, D3-22, D4-17, D6-13 and D6-19, or
D2-2*02, D3-9*01, D3-10*01, D3-22*01,
D4-17*01, D6-13*01 and D6-19*01, or
D1-26, D2-2, D3-10 and D6-19, or
D2-2, D3-9 and D3-10.

35. The antibody of clause 34, wherein the antibody is obtained or obtainable from a vertebrate according to any one of clauses 1 to 32.

In an embodiment, the antibody is obtained from said vertebrate, or is a copy of such an antibody.

36. A method of isolating an antibody that binds a predetermined antigen, the method comprising
(a) providing a vertebrate (optionally a mouse or rat) according to any one of clauses 1 to 32;
(b) immunising said vertebrate with said antigen;
(c) removing B lymphocytes from the vertebrate and selecting one or more B lymphocytes expressing antibodies that bind to the antigen;
(d) optionally immortalising said selected B lymphocytes or progeny thereof, optionally by producing hybridomas therefrom; and
(e) isolating an antibody (eg, and IgG-type antibody) expressed by the B lymphocytes.

37. The method of clause 36, wherein in step (e) wherein the antibody has a HCDR3 length of at least 20 amino acids (according to IMGT).

The length can be 20, 21, 22, 23, 24, 25, 26, 27, 28, 29 or 30 amino acids (according to IMGT), eg, from 20 to 23 amino acids (a produced in the examples).

38. The method of clause 36 or 37, comprising the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

39. The method of clause 36, 37 or 38, further comprising making a copy, mutant or derivative (eg, humanised version) of the antibody produced by the method.

Humanisation can entail making the constant regions human.

40. The antibody composition, cell population, antibody or method of any one of clauses 33 to 39, wherein the antigen is an antigen of an infectious disease pathogen; optionally wherein the pathogen is a virus or bacterium.

41. The antibody composition, cell population, antibody or method of clause 40, wherein pathogen is selected from the group consisting of *Haemophilus influenza, E. coli,*

Neisseria meningitidis, a herpes family virus, cytomegalovirus (CMV), HIV and influenza virus.

42. The antibody composition, cell population, antibody or method of any one of clauses 33 to 41, wherein the antigen is a HIV gp120 antigen or a HIV gp41 antigen.

43. The antibody composition, cell population, antibody or method of any one of clauses 33 to 40, wherein the antigen comprises an active site or cleft, wherein the antibody having a HCDR3 length of at least 20 amino acids specifically binds to the active site or cleft of the antigen.

44. A pharmaceutical composition comprising an antibody or antibody composition according to any one of clauses 33 to 35 and 40 to 43, or an antibody produced by the method of any one of clauses 36 to 38, for treating and/or preventing an infectious disease in a human (eg, wherein the infectious disease is caused by a pathogen selected from the group consisting of Haemophilus influenza, E. coli, Neisseria meningitidis, a herpes family virus, cytomegalovirus (CMV), HIV and influenza virus).

45. A repertoire of antibody heavy chains (eg, provided by antibodies) comprising one or more heavy chains whose variable domain HCDR3 has a length of at least 20 amino acids (according to IMGT) and derived from the recombination of a human VH, D and JH, wherein
the VH is selected from the group
VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01 and
the D is selected from the group
D2-2*02, D3-9*01, D3-10*01 and D3-22*01, or
D2-2*02, D3-9*01 and D3-10*01, or
D3-9*01 and D3-10*01, or
D1-26, D2-2, D3-9, D3-10, D3-22, D4-17, D6-13 and D6-19, or
D1-26*01, D2-2*02, D3-9*01, D3-10*01, D3-22*01, D4-17*01, D6-13*01 and D6-19*01, or
D2-2, D3-9, D3-10, D3-22, D4-17, D6-13 and D6-19, or
D2-2*02, D3-9*01, D3-10*01, D3-22*01,
D4-17*01, D6-13*01 and D6-19*01, or
D1-26, D2-2, D3-10 and D6-19, or
D2-2, D3-9 and D3-10;
and optionally the JH is JH6 (eg, JH6*02);
Wherein
(a) the heavy chain variable domain has been produced in vivo in a non-human vertebrate (eg, a mouse or a rat); and/or
(b) the heavy chain variable domain comprises non-human vertebrate AID-pattern somatic hypermutations, (eg, mouse or rat AID-pattern mutations) when compared to corresponding human germline V, D and J sequences and/or non-human (eg, mouse or rat) terminal deoxynucleotidyl transferase (TdT)-pattern junctional mutations when compared to corresponding human germline V, D and J sequences.

In an example, the heavy chain (or all heavy chains in the repertoire) comprise non-human vertebrate constant regions (eg, mouse or rat constant regions). For example, the constant regions are gamma-type constant regions (eg, gamma-1, gamma-2 or gamma-4 type).

In an example, the repertoire is a naïve repertoire. This is shown in the examples section herein.

In an example, the repertoire is an immunised repertoire. This is shown in the examples section herein.

In an example, the repertoire is an antigen-specific repertoire (eg, provided by a plurality of hybridomas). This is shown in the examples section herein.

The repertoire can be provided by B cells (eg, immortalised B cells).

The repertoire can be provided by hybridomas.

In an example, the vectors are harboured by host cells (eg, CHO or HEK293 cells or yeast cells).

The HCDR3 length can be 20, 21, 22, 23, 24, 25, 26, 27, 28, 29 or 30 amino acids (according to IMGT), eg, from 20 to 23 amino acids (a produced in the examples).

In an example, in (a) the vertebrate is a vertebrate according to the invention.

46. A nucleic acid collection encoding the heavy chain repertoire of clause 45.

In an example, the nucleic acids are provided in respective vectors (eg, expression vectors, eg, E coli or CHO or HEK293 vectors).

47. A method of obtaining an antigen-specific heavy chain (eg, provided by an antibody), the method comprising exposing the repertoire of clause 45 to a predetermined antigen and selecting one or more heavy chains that specifically bind to the antigen, wherein one or more heavy chains is isolated that has a HCDR3 length of at least 20 amino acids.

Optionally, when the heavy chain has a non-human constant region, this is swapped for a human constant region, as is conventional in the art. Thus, the invention provides a human antibody heavy chain so produced (eg, provided in combination with a human light chain to produce a human antibody which is useful for human therapeutic and/or prophylactic use, eg, to treat and/or prevent an infectious disease in a human patient).

In an example of the vertebrate or cell of any aspect of the invention, the genome comprises an immunoglobulin light chain locus comprising one or more human V gene segments and one or more human J gene segments upstream of a constant region (eg, a human or a mouse lambda or kappa constant region).

For rearrangement and expression of heavy chains, the locus comprises control elements, such as an Eμ and Sμ between the J gene segment(s) and the constant region as is known by the skilled person. In one example, a mouse Eμ and Sμ is included in the heavy chain locus between the JH repertoire and the constant region (ie, in 5' to 3' order the locus comprises the JH gene segment(s), Eμ and Sμ and constant region). In an example, the Eμ and Sμ are Eμ and Sμ of a mouse 129-derived genome (eg, a 129Sv-derived genome, eg, 129Sv/EV (such as 129S7Sv/Ev (such as from AB2.1 or AB2.2 cells obtainable from Baylor College of Medicine, Texas, USA) or 129S6Sv/Ev))); in another example, the Eμ and Sμ are Eμ and Sμ of a mouse C57BL/6-derived genome. In this respect, the locus can be constructed in the IgH locus of the genome of a cell selected from AB2.1, AB2.2, VGF1, C17 and FH14. VGF1 cells were established and described in Auerbach W, Dunmore J H, Fairchild-Huntress V, et al; Establishment and chimera analysis of 129/SvEv- and C57BL/6-derived mouse embryonic stem cell lines. Biotechniques 2000; 29:1024-8, 30, 32, incorporated herein by reference.

Additionally or alternatively, the constant region (or at least a Cμ; or Cμ and gamma constant regions thereof) is a constant region (or Cμ; or Cμ and gamma constant regions thereof) is of a genome described in the paragraph immediately above.

A suitable source of human DNA sequences or gene segments will be readily apparent to the skilled person. For example, it is possible to collect a DNA sample from a consenting human donor (eg, a cheek swab sample as per the Example herein) from which can be obtained suitable DNA sequences for use in constructing a locus of the invention. Other sources of human DNA are commercially available, as will be known to the skilled person. Alternatively, the skilled person is able to construct gene segment sequence by referring to one or more databases of human Ig gene segment sequences disclosed herein.

In an example, the genome comprises all or some of the following human VH gene segments
IGHV6-1
IGHV3-7
IGHV1-8
IGHV3-9
IGHV3-11
IGHV3-13
IGHV1-18
IGHV3-30
IGHV4-31
IGHV4-39
IGHV4-59
   Optionally also (i) and/or (ii)
   (i)
   IGHV1-2
   IGHV2-5 and
   IGHV3-21
   (ii)
   IGHV1-2
   IGHV2-5
   IGHV3-21
   IGHV1-24

For example, the genome comprises all or some of the following human VH gene segment variants
IGHV6-1*01
IGHV3-7*01
IGHV1-8*01
IGHV3-9*01
IGHV3-11*01
IGHV3-13*01
IGHV1-18*01
IGHV3-30*18
IGHV4-31*03
IGHV4-39*01 and
   IGHV4-59*01;
   Optionally also (iii) or (iv)
   (ii)
   IGHV1-2*04
   IGHV2-5*10 and
   IGHV3-21*03
   (iv)
   IGHV1-2*02
   IGHV2-5*01
   IGHV3-21*01 and
   IGHV1-24*01

For example, the genome comprises all or some of the following human JH gene segment variants
   IGHJ2*01
   IGHJ3*02
   IGHJ4*02
   IGHJ5*02 and
   IGHJ6*02

For example, the genome comprises all or some of the following human D gene segments
   IGHD1-1
   IGHD2-2
   IGHD3-9
   IGHD3-10
   IGH D5-12
   IGHD6-13
   IGHD1-14
   IGHD2-15
   IGHD3-16
   IGHD4-17
   IGHD6-19
   IGHD2-21
   IGHD5-24
   IGHD1-26 and
   IGHD7-27
   and optionally also (v) or (vi)
   (v)
   IGHD3-3
   (vi)
   IGHD3-3
   IGHD4-4
   IGHD5-5
   IGHD6-6
   IGHD1-7
   IGHD2-8 and
   IGHD2-8

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non limiting Examples (Examples 1-3 being prophetic). Example 4 is a worked example.

EXAMPLES

Example 1

Recombineered BAC Vectors to Add Polymorphic V-Regions to the Mouse Genome

Figure 3:
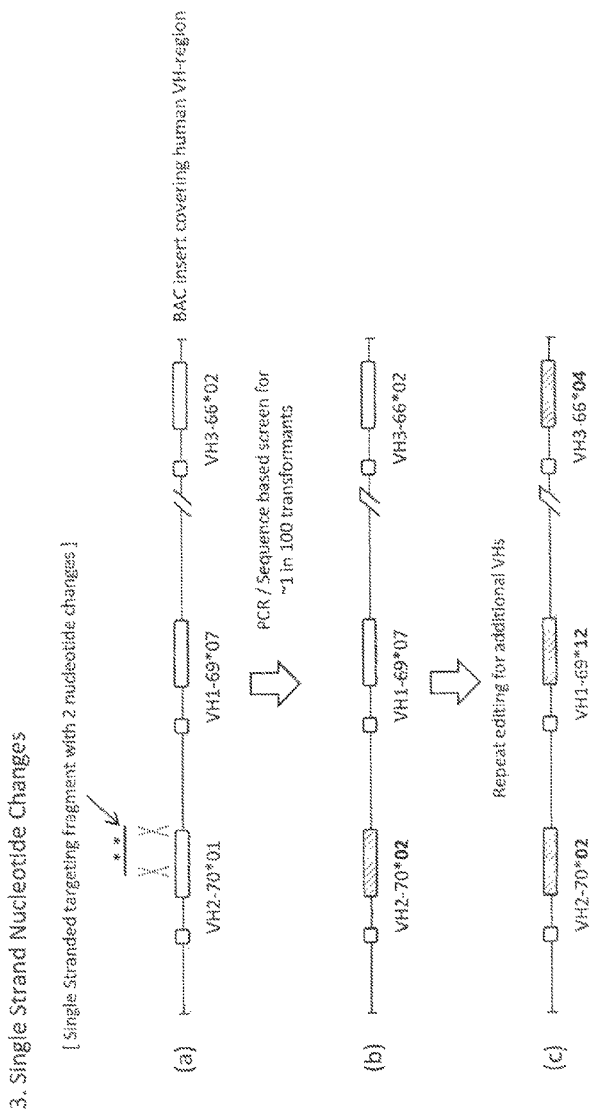

FIG. 1 through 3 depict recombineering methods (see references above) that can be used to introduce polymorphic V-gene regions into genomic DNA. In one embodiment, a genomic fragment from the human heavy chain region is inserted into a bacterial artificial chromosome (BAC) vector by standard techniques. Preferably, such a BAC, which can range in size from 20-kb to 200-kb or more, can be isolated from libraries of BACs by standard techniques including sequence searches of commercially available libraries or by hybridization to bacterial colonies containing BACs to identify those with a BAC of interest.

A BAC is chosen that has several VH gene segments; in FIG. 1, these are generically identified as VH[a] through VH[z] for example. One skilled in the art will readily identify appropriate genomic fragments, for example, an approximately 120-kb fragment from human VH5-78 through VH1-68 which includes 5 endogenous active VH gene segments and 7 VH psuedogenes. Using recombineering techniques, the endogenous VH gene segments can be replaced by polymorphic VH or VL gene segments. In this example, two steps are required. The first step replaces the V-region coding exon of an endogenous VH gene segment with a positive-negative selection operon, in this example, an operon encoding an ampicillin resistance gene (Amp) and a streptomycin-sensitizing ribosomal protein (rpsL). Certain strains of bacteria can be selected for the absence of the rpsL gene by resistance to streptomycin. Short stretches of DNA homologous to sequences flanking the endogenous VH gene exon are placed 5' and 3' of the rpsL-Amp operon. In the presence of appropriate recombination factors per standard recombineering techniques (see references above) recombination between the operon fragment and the BAC will result in replacement of the endogenous VH gene exon with the operon (FIG. 1a) which are selected by resistance to ampi-cillin. The second step uses the same homologous sequences in order to replace the inserted operon with a desired polymorphic VH gene segment. In this example, a human VI-1'-69 gene is inserted (FIGS. 1b and 1c). In particular the *02 allele of VH1-69 is used [ref IMGT and FIG. 5]. Successful integrations of the polymorphic VH gene segment are selected in bacteria that become resistant to streptomycin due to the loss of the operon, specifically the rpsL portion.

In this example, the two step process as described can be repeated for each of the endogenous VH gene segments or for as many endogenous gene segments that one wishes to replace with polymorphic V gene segments (FIG. 1d).

As is apparent, any polymorphic V gene segment can be inserted in this manner and any endogenous V gene segment can act as a target, including pseudogenes. V gene segments in each of the heavy chain and two light chain loci can be replaced using this technique with appropriate genomic fragments available as BAC inserts.

FIG. 2 depicts another method for creating a genomic fragment encoding polymorphic V gene segments. In this example, polymorphic V gene segments are inserted into a region of genomic DNA devoid of other genes, control elements or other functions. Such 'desert' regions can be selected based on sequence analysis and corresponding DNA fragments cloned into BACs or identified in existing BAC libraries. Starting with such a genomic fragment, recombineering techniques can be used to insert polymorphic V gene segments at intervals of, for example, 10-kb. In this example, a 150-kb genomic fragment might accommodate insertion of up to 15 polymorphic V gene segments. Insertion of the segments is a two-step process. The first recombineering step inserts the rpsL-Amp operon at a specific site. Sequences homologous to a specific site are used to flank the operon. These are used by the recombineering system to insert the element specifically into the BAC genomic fragment and positive events are selected by resistance to ampicillin (FIG. 2a). The second step replaces the operon in the genomic fragment with a polymorphic V gene segment by a similar recombineering step using the same sequence homology (FIG. 2b). In this example, both exons and promoter element of a polymorphic VH gene segment are inserted, resulting in replacement of the rpsL-Amp operon and therefore resistance to streptomycin (FIG. 2c).

The two step technique for inserting polymorphic V gene segments into a specific site on the genomic fragment can be repeated multiple times resulting in a BAC genomic fragment with several polymorphic gene segments, including their promoter elements. It is apparent that the examples shown in FIGS. 1 and 2 can be combined wherein the technique for insertion can be used to add extra polymorphic V gene segments to a BAC genomic fragment as depicted in FIG. 1. One might choose to add these extra segments to an IG genomic fragment since such a fragment would be more amenable to proper IG gene expression once inserted into a non-human mammal's genome. It is known that a genomic fragment can have elements such as enhancers or elements that contribute to certain chromatin conformations, both important in wild-type gene expression.

FIG. 3 depicts an additional method to create genomic fragments with polymorphic V gene segments. This method depends upon the efficiency with which short (around 50 to 150 bases, preferably 100 bases) single stranded DNA fragments recombine with a homologous sequence using recombineering (Nat Rev Genet. 2001 October; 2(10):769-79; Recombineering: a powerful new tool for mouse functional genomics; Copeland N G, Jenkins N A, Court D L). The recombinases used in recombineering preferentially bind and use such short single-stranded fragments of DNA as a substrate for initiating homologous recombination. The efficiency can be as high as 10-2, that is, a positive event can be found in approximately 100 randomly picked (not selected) clones resulting from recombineering. A positive event in this example occurring when one or more single nucleotide changes introduced into the single-stranded fragment get transferred to the BAC insert containing V gene segments and surrounding genomic DNA, said nucleotide change or changes occurring at a homologous sequence on the BAC.

Figure 5C:
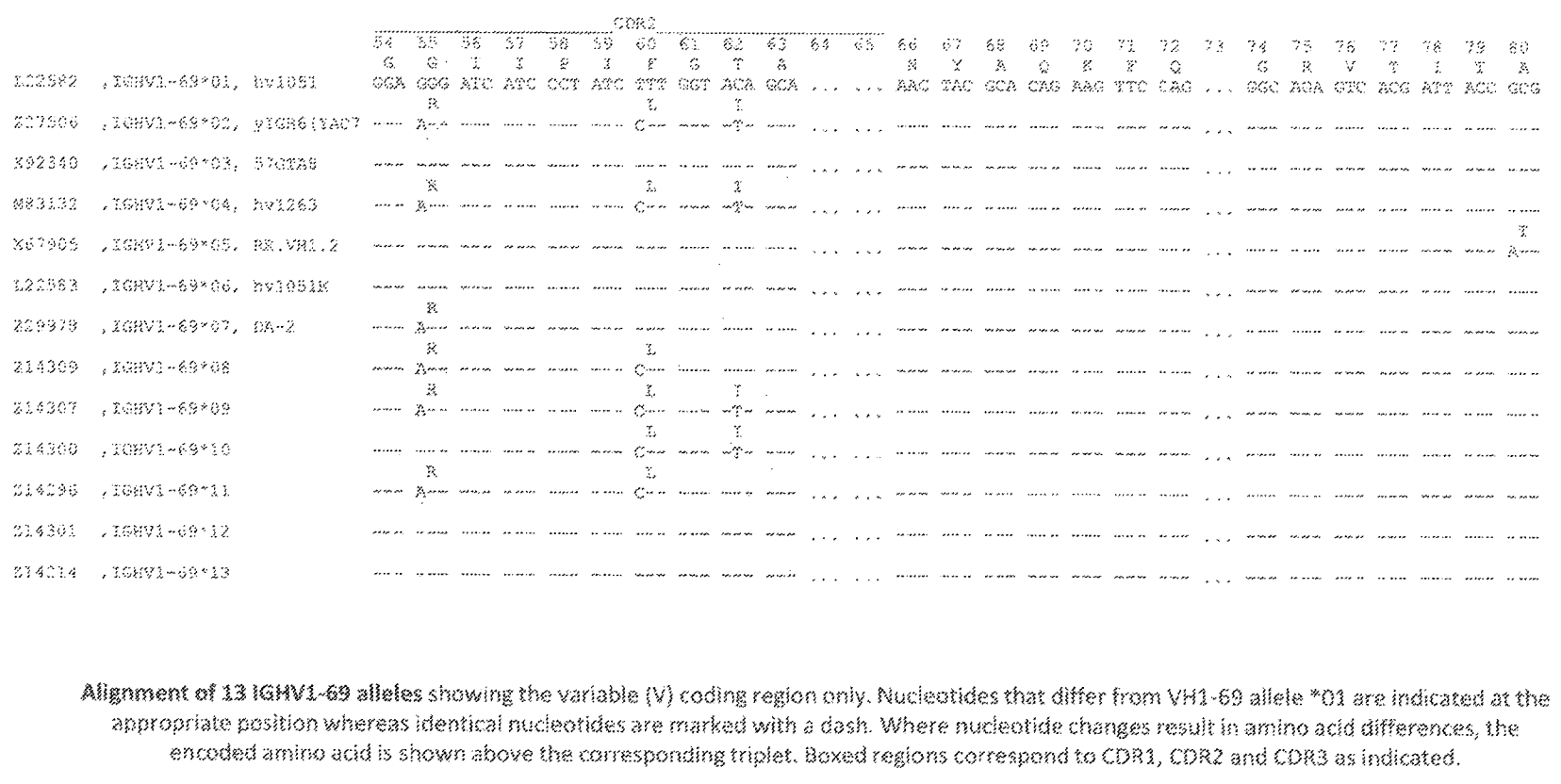

Polymorphic V gene segments can differ from endogenous V gene segments by only 1 or 2, or up to 10 or 15 nucleotide changes, for example. An example of such nucleotide polymorphisms are depicted in FIG. 5. Short single stranded regions that encompass the polymorphic nucleotide changes can be chemically synthesized using standard techniques. The resulting single stranded DNA fragments are introduced into bacteria and via recombineering techniques approximately 1 in 100 BAC fragments will have incorporated the polymorphic nucleotides via homologous incorporation of the single stranded fragment (FIG. 3a). BACs with the desired nucleotide change can be identified by screening for example several hundred individual clones by polymerase chain reaction (PCR) amplification and sequencing, both by standard techniques. In the example, two nucleotide changes will convert a VH1-69*01 gene segment into a VH1-69*02 gene segment (FIG. 3b).

It is clear that this process can be repeated for multiple endogenous V gene segments contained on a single BAC genomic fragment. In addition, the techniques depicted in FIG. 2 can be used to add additional polymorphic V gene segments by insertion into regions between existing V gene segments. As would be evident to one skilled in the art, a combination of these techniques can be used to create numerous variations of both polymorphic and endogenous human V gene segments. And it would be evident that several different genomic fragments with engineered polymorphic V gene segments and endogenous human V gene segments can be combined to create even more variations.

Example 2

Adding Polymorphic V-Regions to the Genome Using SRMCE of Modified BACs

Modified BACs with polymorphic V gene segments created using the methods described in Example 1 can be used to alter the genome of non-human mammals. These alterations can result in an intact IG locus in which normal immunoglobin region recombination results in VDJ or VJ combinations which includes the human V gene segments. An example of how such an animal can be created is by altering the genome of, for example, mouse embryonic stem (ES) cells using the strategy outlined in FIG. 4.

One technique to integrate modified BACs with polymorphic V gene segments into a genome is sequential recombinase mediated cassette exchange (SRMCE). The technique is described in WO2011004192 (Genome Research Limited), which is incorporated here in its entirety by reference.

Figure 4:
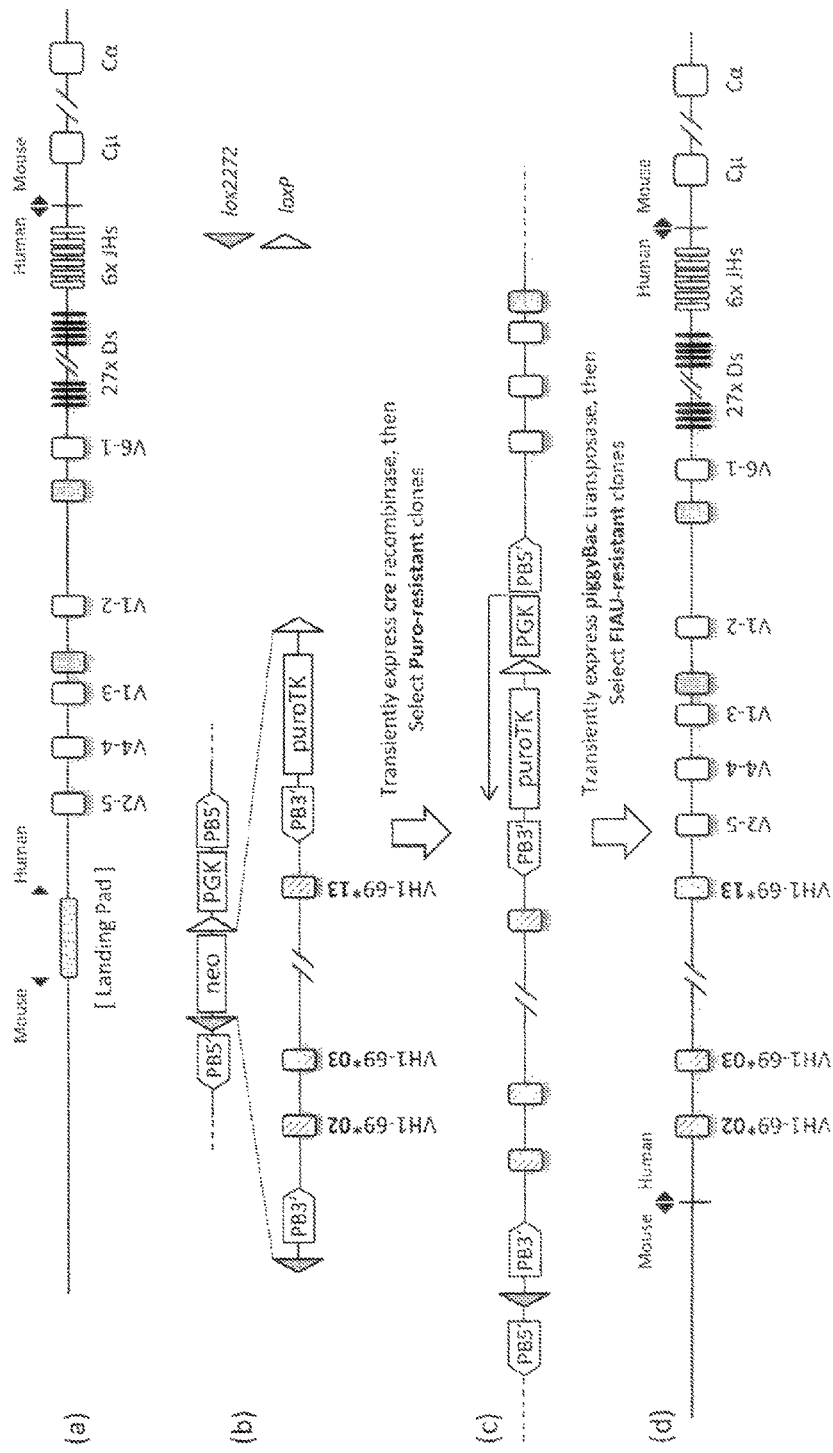
FIG. 4: Schematic illustrating a protocol for adding V gene segments to a mouse genome using sequential recombinase mediated cassette exchange (sRMCE)

SRMCE provides for a locus modified with a 'landing pad' inserted at a specific location. This insertion can either be de novo via homologous recombination or as a consequence of a previous BAC insertion. In this example, the landing pad is inserted in the mouse IGH locus between the most 3'J gene segment and the Cμ gene segment and a previous BAC insertion via SRMCE techniques have resulted in the addition of 5 human V gene segments and 2 V region pseudogenes. The landing pad has elements as shown in FIG. 4 that will allow the selection of correct insertion of a second targeting BAC fragment. The specificity of this insertion is provided by cre recombinase-mediated exchange between permissive lox sites. A lox site is permissive for recombination only with a compatible lox site. In this example, the loxP site will only recombine with loxP and lox2272 will only recombine with lox2272. This provides directionality to the insertion of the BAC fragment as depicted in FIGS. 4b and 4c.

ES cell clones with correct insertions are selected from a pool of clones without insertions or with non-productive insertions by resistance to puromycin. Resistance to puromycin results from the juxtaposition of an active promoter element, PGK, with the puroTK coding region. Correct insertions are verified by standard techniques including PCR of junctions, PCR of internal elements, Southern blotting, comparative genomic hybridization (CGH), sequencing and etc. In the example, correct lox2272-lox2272 and loxP-loxP recombination also results in two intact sets of piggyBac elements that did not exist prior to insertion. An intact piggyBac element is comprised of a set of inverted repeats which are depicted in the figure by "PB5'" and "PB3'". An appropriated oriented set of piggyBac elements are the substrate of piggyBac transposase which can catalyse recombination between the elements, resulting in deletion of intervening sequences as well as both elements. The DNA remaining after a piggyBac transposition is left intact and is lacking any remnant of the piggyBac element. In the example, ES cell clones with successful piggyBac transposition are selected by loss of the active puroTK element which renders the cells resistant to the drug FIAU (FIGS. 4c and 4d).

The final product of the SRMCE method in this example is a IGH locus with several polymorphic V gene segments inserted along with a set of endogenous unmodified VH gene segments between sequences of the mouse genome on the 5' side and the mouse IGH constant region gene segments on the 3' side. The polymorphic V gene segments are positioned such that they can participate in the recombination events associated with B cell maturation yielding VDJ gene segments. These gene segments can then be transcribed and spliced to the mouse constant region. Translation of these transcripts will result in the production of an antibody heavy chain encoded by the polymorphic V gene segment, a human DH gene segment, a human JH gene segment and a mouse constant heavy chain gene segment.

As is well known to those skilled in the art, an ES cell clone can be used to create a line of genetically modified mice via injection of said cells into a mouse blastocyst embryo, transferring the injected embryo to a suitable recipient and breeding the chimeric offspring that result. The modified gene locus can be propagated through breeding and made either heterozygous or homozygous depending on the genetic cross.

It is evident from the structure of the IGH locus provided in this example and by knowledge of the mechanisms involved in B cell receptor (BCR) and antibody gene rearrangements that a large set of different combinations of polymorphic V gene segments with various DH and JH gene segments will result and these can contribute to a large repertoire of functional antibody genes in a population of B cells in genetically modified animals. In this example, several different human VH1-69 polymorphs are incorporated to provide superhuman VH diversity. This particular VH gene segment is known to be prevalent in antibodies that bind infectious disease pathogens (such as influenza virus) and therefore the antibody repertoire of a mouse with the genetic modification of this example would be expected to produce antibodies with a bias in favour of those that bind infectious disease pathogens. The repertoire, in other words, would have a larger subset of antibodies with superior affinities for pathogen antigens. Examples of such pathogens include influenza virus, hepatitis C virus (HCV) and human immunodeficiency virus-1 (HIV-1) (see also table above).

Example 3

Alignment of 13 VH1-69 Alleles

Building a more diverse antibody repertoire by incorporating additional V gene segment polymorphs requires availability of polymorphic alleles of V gene segments. One source of such alleles include sequence databases. In this example, 13 distinct alleles of the VH1-69 gene segment are provided. These allele sequences and comparisons are drawn from the "IMmunoGeneTics" I MGT Information System database found online at imgt.com. FIG. 5 is a diagram of the alignment of alleles *02 through *13 with the *01 allele. The VH 1-69*01 nucleotide and amino acid sequence is provided at the top of the figure. Where the remaining alleles are identical to the *01 allele sequence a dash is inserted below the sequence. Nucleotide differences are noted alongside the appropriate allele and if the sequence change results in a protein coding change, the amino acid change is indicated above the triplet.

FIG. 5 depicts between 1 and 4 amino acid changes for each allele in comparison to the *01 allele. All of the amino acid changes occur in the part of the heavy chain protein encoding the complementarity determining regions (CDRs). These regions are responsible for antigen specificity and the affinity of the antibody for the antigen. It is evident that providing additional polymorphic CDRs in a repertoire of antibodies will increase the likelihood of there being an antibody with superior binding characteristics for various antigens. In several reports, it has been observed that the VH1-69-encoded variable region of the heavy chain is often found in antibodies that bind influenza virus, HCV and HIV-1 antigens (see table above). Therefore incorporating the polymorphic V gene segments of this example into a transgenic animal model using the methods of Examples 1 and 2 would likely result in an antibody repertoire in said transgenic animal with more antibodies that bind to antigens associated with these and other pathogens. And as is known in the art, a larger repertoire increases the probability of finding monoclonal antibodies using, for example, hybridoma technology, that bind with high affinity and specificity to a desired antigen.

This disclosure therefore describes in these examples a transgenic mouse model which can be immunized with pathogen or other antigens. Plasma B cells from such an immunized mouse can be used to make a hybridoma library that can be screened for production of antibodies that bind the pathogen antigens. This library will be superior to libraries from traditional transgenic mice for finding such antibodies given the addition of polymorphic VH1-69 gene segments to the IGH locus in said transgenic mouse.

These examples are not limiting to the human polymorphic V gene segments that can be chosen or to the methods used to introduce them into an animal model. The method can be used to construct a transgenic locus with immunoglobulin D and/or J segments. The V, D, J segments can be from a plurality of human sources (optionally more than one human ethnic population).

Example 4

Transgenic Mice, B-Cells, Hybridomas, Antibodies & Heavy Chains Based on Human JH6*02

A functional human gene segment repertoire (from VH2-26 to JH6, see the online IMGT database for the structure of the human IgH locus at imgt.org/IMGTrepertoire/index.php?section=LocusGenes&repertoire=locus&species=human&group=IGK) was sectored by the inventors to produce two different transgenic heavy chain alleles (denoted S2F and S3F) and corresponding mice. The transgenic alleles were expressed in the mice and the heavy chain repertoires were assessed at the RNA transcript level. Deep sequence analysis was carried out using Bioinformatics methods to assess V, D and JH gene usage, including in variable domain sequences having a HCDR3 length of at least 20 amino acids. Endogenous, mouse variable region gene segments were inactivated by inversion (as per the method described in WO2011004192 this disclosure being incorporated herein by reference).

Sequencing of Human Donor DNA Samples: Identification of Conserved JH6*02 Variant DNA samples from 9 anonymised consenting human donors were obtained by taking cheek swabs.

The samples were processed and the DNA Samples were extracted follow the protocol of QIAamp DNA Mini Kit (Cat. No. 51304, Qiagen).

PCR reactions were set up to amplify the JH6 region and PCR products were sequenced (PCR Oligos sequence: Fwd. 5'-AGGCCAGCAGAGGGTTCCATG-3' (SEQ ID NO: 444), Rev. 5'-GGCTCCCAGATCCTCAAGGCAC-3' (SEQ ID NO: 445)).

Sequence analysis was carried out by comparing to the JH6 reference sequence from the online IMGT annotated database, and this Identified that all 9 donor genomes contained the human JH6*02 variant, with this variant being in the homozygous state in 7 out of the 9 donors. The inventors also consulted the genomic sequences publicly available for Jim Watson and Craig Venter at Ensembl human genome online database at ensembl.org/]. These too contained the human JH6*02 variant. This confirmed to the inventors that human JH6*02 is a common, conserved variant in humans, and thus a good candidate for construction of a transgenic IgH locus as per the invention.

Identification of Suitable Human DNA Sequence BACs

A series of human bacterial artificial chromosome (BAC) clones were identified from Ensemble (http://www.ensembl.org/index.html) or UCSC (http://genome.ucsc.edu/) human database searches based on gene name (IGH) or location (chromosome 14: 106026574-107346185). Seven human RP11 BAC clones were selected, RP11-1065N8 BAC carrying human JH6*02. In total, the following BACs were identified as sources of human IgH locus DNA: RP11-1065N8, RP11-659B19, RP11-141I7, RP-112H5, RP11-101G24, RP11-12F16 and RP11-47P23.

With a similar approach, different BAC clones (eg, different RP11 clone IDs or different sources from RP11) or genetically engineered BACs can be selected for insertion into the mouse IGH locus to provide different sets of human repertoires in the transgenic mouse.

Construction of Transgenic IgH Loci

Insertion of human heavy gene segments from a 1st IGH BAC (RP11-1065N8) into the IGH locus of mouse AB2.1 ES cells (Baylor College of Medicine) was performed to create a heavy chain allele denoted the S1 allele. The inserted human sequence corresponds to the sequence of human chromosome 14 from position 106494908 to position 106328951 and comprises functional heavy gene segments $V_H2$-5, $V_H7$-4-1, $V_H4$-4, $V_H1$-3, $V_H1$-2, $V_H6$-1, D1-1, D2-2, D3-9, D3-10, D4-11, D5-12, D6-13, D1-14, D2-15, D3-16, D4-17, D5-18, D6-19, D1-20, D2-21, D3-22, D4-23, D5-24, D6-25, D1-26, D7-27, $J_H1$, $J_H2$, $J_H3$, $J_H4$, $J_5$ and $J_H6$ (in 5' to 3' order), wherein the JH6 was chosen to be the human JH6*02 variant. The insertion was made between positions 114666435 and 114666436 on mouse chromosome 12, which is upstream of the mouse Cu region. The mouse $V_H$, D and $J_H$ gene segments were retained in the locus, immediately upstream of (5' of) the inserted human heavy chain DNA.

A second allele, S2 was constructed in which more human functional $V_H$ gene segments were inserted upstream (5') of the 5'-most $V_H$ inserted in the S1 allele by the sequential insertion of human DNA from a second BAC (BAC2). The inserted human sequence from BAC2 corresponds to the sequence of human chromosome 14 from position 106601551 to position 106494909 and comprises functional heavy chain gene segments $V_H3$-13, $V_H3$-11, $V_H3$-9, $V_H1$-8, $V_H3$-7. The mouse $V_H$, D and $J_H$ gene segments were retained in the locus, immediately upstream of (5' of) the inserted human heavy chain DNA. In a subsequent step, these were inverted to inactivate them, thereby producing S2F mice in which only the human heavy chain variable region gene segments are active.

A third allele, S3 was constructed in which more human functional $V_H$ gene segments were inserted upstream (5') of the 5'-most $V_H$ inserted in the S2 allele by the sequential insertion of human DNA from a third BAC (BAC3). The inserted sequence corresponds to the sequence of human chromosome 14 from position 106759988 to position 106609301, and comprises functional heavy chain gene segments, $V_H2$-26, $V_H1$-24, $V_H3$-23, $V_H3$-21, $V_H3$-20, $V_H1$-18, and $V_H3$-15. The mouse $V_H$, D and $J_H$ gene segments were retained in the locus, immediately upstream of (5' of) the inserted human heavy chain DNA. In a subsequent step, these were inverted to inactivate them, thereby producing S3F mice in which only the human heavy chain variable region gene segments are active.

Mice bearing either the S2F or S3F insertion into an endogenous heavy chain locus were generated from the ES cells using standard procedures. The other endogenous heavy chain locus was inactivated in the mice by insertion of an inactivating sequence comprising $neo^R$ into the mouse $J_H$-Cμ intron (to produce the "HA" allele).

Specifically, the following alleles were included:—
VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01
D1-26*01, D2-2*02, D3-9*01, D3-10*01, D3-22*01, D4-17*01, D6-13*01 and D6-19*01

Immunisation Procedure

Transgenic mice of the S2F or S3F genotype were primed with 20-40 ug recombinant proteins obtained commercially or produced in house with Antigen 1 (OVA (Sigma A7641); Antigen 2 (a human infectious disease pathogen antigen) and Antigen 3 (a human antigen) via the ip route in complete Freunds adjuvant (Sigma F 5881) and 10 ug/animal CpG (CpG oligo; Invivogen, San Diego, Calif., USA) and then boosted twice in about two weekly intervals with about half the amount of antigen in incomplete Freunds adjuvant (Sigma F 5506) and 10 ug/animal CpG. Final boosts were administered two weeks later iv without any adjuvant and contained 5-10 ug protein in PBS.

Hybridoma Fusion Procedure

Spleens were taken 3 days after the final boost and spleenocytes were treated with CpG (25 μm final concentration) for and left until the following day. Cells were then fused with SP0/2 Ag14 myeloma cells (HPA Cultures Cat No 85072401) using a BTX ECM2001 electrofusion instrument. Fused cells were left to recover for 20 minutes then seeded in a T75 flask until next morning. Then the cells were spun down and plated out by dilution series on 96-well culture plates and left for about 10 days before screening. Media was changed 1-3 times during this period.

Screening

Culture supernatants of the hybridoma wells above were screened using homogenious time resolved fluorescence assay (htrf) using Europium cryptate labelled anti-mouse IgG (Cisbio anti-mouse Ig Europium Cryptate) and a biotin tagged target antigen with a commercially available streptavidin conjugated donor (Cisbio; streptaviding conjugated D2) or by IgG-specific 384 well ELISA. Positive wells identified by htrf were scaled to 24-well plates or immediately counterscreened using an IgG-specific detection ELISA method. Positives identified by primary ELISA screen were immediately expanded to 24-well plates. Once cultures were expanded to 24-well stage and reached confluency, supernatants were re-tested using htrf or IgG-specific ELISA to confirm binding to target antigen. Supernatant of such confirmed cultures were then also analysed by surface plasmon resonance using a BioRad ProteOn XPR36 instrument. For this, antibody expressed in the hybridoma cultures was captured on a biosensor GLM chip (BioRad 176-512) which had an anti-mouse IgG (GE Healthcare BR-1008-38)) covalently coupled the biosensor chip surface. The antigen was then used as the analyte and passed over the captured hybridoma antibody surface. For Antigen 2 and Antigen 3, concentrations of 256 nM, 64 nM, 16 nM, 4 nM and 1 nM were typically used, for Antigen 1, concentrations of 1028 nM, 256 nM, 64 nM, 16 nM and 4 nM were typically used, binding curves were double referenced using a 0 nM injection (i.e. buffer alone). Kinetics and overall affinities were determined using the 1:1 model inherent to the BioRad ProteOn XPR36 analysis software.

Any clones with confirmed binding activity were used for preparing total RNA and followed by PCR to recover the heavy chain variable region sequences. Standard 5'-RACE was carried out to analyse RNA transcripts from the transgenic heavy chain loci in the S2F and S3F mice. Additionally, deep sequence analysis of almost 2000 sequences produced by the mice was carried out.

Bioinformatics Analysis

Sequences for analysis were obtained from two different methods:
  The first is from RNA extracted from the spleen: first cDNA strand was synthesized using an oligo based on the Cmu region of the mouse IGH locus as a PCR template. PCR was performed using this oligo with an oligo dT-anchor primer. Then PCR product was cloned into pDrive vector (Qiagen) and then sequenced.
  The second is from hybridomas generated through electro-fusion: total RNA was extracted from hybridoma lines of interest using standard Trizol methods and frozen at −80° C. for long term storage. cDNA was generated from 100 ng total RNA using standard Superscript III reverse transcriptase and a gene-specific reverse primer binding to all mouse IgG isotypes for heavy chain and a mouse kappa constant region primer for the light chain amplification. 2-3 ul of cDNA were then used as template in a PCR reaction using Pfu DNA polymerase and a panel of degenerate forward primers annealing to the leader sequence of the human immunoglobulin variable domain as well as one mouse pan-IgG reverse primer. PCR products were run out of a 1% agarose gel and bands of approximately 350-450 basepairs extracted and purified. DNA was then sequenced.

The sequences from the first method can either be from IgM from Naïve mice or IgG from immunised mice. The samples from the second method are all from IgG from immunised mice, and specific to the immunising antigen. Almost 2000 sequences were analysed.

The sequences were obtained as a pair of forward and reverse reads. These were first trimmed to remove low-quality base calls from the ends of the reads (trimmed from both ends until a 19 nucleotide window had an average quality score of 25 or more). The reads were combined together by taking the reverse complement of the reverse read, and aligning it against the forward read. The alignment scoring was 5 for a match, −4 for a mismatch, a gap open penalty of 10 and a gap extension penalty of 1. A consensus sequence, was then produced by stepping through the alignment and comparing bases. When there was a disagreement the base with the highest quality value from sequencing was used.

The BLAST+(Basic Local Alignment Search Tool) (Camacho C., Coulouris G., Avagyan V., Ma N., Papadopoulos J., Bealer K., & Madden T. L. (2008) "BLAST+: architecture and applications." BMC Bioinformatics 10:421 found online at ncbi.nlm.nih.gov/pubmed/20003500) program 'blastn' was then used to find the germline J and V segments used in each sequence. A wordsize of 30 was used for V matching, and 15 for J matching. The database searched against was constructed from the NGS sequencing of the BACs which were used to generate the Kymouse.

If a sequence matched both a V and a J segment, the sequence between the two was then compared to a database of germline D segments in the mouse using 'blastn' with a wordsize of 4 and the options 'blastn-short' and 'ungapped'. This was used to assign a D segment, if possible. The CDR3 was identified by searching for the conserved "TATTACTGT" sequence in the V segment, and the "CTGGGG" in the J segment. If these motifs were not found, then up to 4 mismatches were allowed. The IMGT definition of CDR3 was used, so the CDR3 length is calculated from after the "TGT" in the V to before the "TGG" in the J. Sequences with an out of frame junction (those which do not have a CDR3 nucleotide length divisible by 3) or which contained a stop codon ("TAA", "TAG" or "TGA") were excluded.

The identity of the matching V, J and D segments as well as the CDR3 length from this assignment were then saved as a table for downstream analysis. The ratio of IGHJ6*02 used increased from the naïve to immunised mice, as well as being enriched in the sub-population of sequences with a long HCDR3 (defined as consisting of 20 or more amino acids):

|  | All | | HCDR3 > 20 | | |
| --- | --- | --- | --- | --- | --- |
|  | JH6*02% | Total Count | JH6*02% | Total Count | % HCDR3 > 20 |
| Naïve | 22.31% | 1340 | 91.11% | 45 | 3.36% |
| Immunised | 37.50% | 256 | 66.67% | 9 | 3.52% |
| Hybridoma | 36.13% | 119 | 63.64% | 11 | 9.24% |

This shows that the JH6*02 gene segment is selected for by immunisation, as the proportion of JH6*02 usage increases after immunisation. JH6*02 is also used in the majority of antibodies with a long HCDR3 length, which is desirable for targets which are specifically bound by long HCDR3 length antibodies.

Additionally, the analysis revealed that certain VH and D gene segments frequently yielded HCDR3s of long length (in all of naïve, immunised and antigen-specific repertoires of heavy chains). See Table 2.

TABLE 2

A: Long HCDR3s from Naïve Repertoires

| V | Average CBR3Length | Count |
| --- | --- | --- |
| IGHV1-2*02 | 21 | 3 |
| IGHV1-18*01 | 21 | 5 |
| IGHV3-7*01 | 22 | 3 |
| IGHV6-1*01 | 21 | 5 |
| IGHV3-9*01 | 20 | 2 |
| IGHV2-5*10 | 20 | 1 |
| IGHV7-4-1*01 | 21 | 3 |
| IGHV1-3*01 | 21 | 5 |
| IGHV4-4*02 | 20 | 3 |
| IGHV3-13*01 | 22 | 1 |
| IGHV3-23*04 | 20 | 1 |
| IGHV1-8*01 | 21 | 10 |
| IGHV3-21*03 | 23 | 3 |

| D | Average CDR3Length | Count |
| --- | --- | --- |
| IGHD2-2*02 | 20 | 1 |
| IGHD3-9*01 | 21 | 13 |
| IGHD3-10*01 | 21 | 26 |
| IGHD6-13*01 | 20 | 1 |
| IGHD4-17*01 | 22 | 2 |
| IGHD6-19*01 | 23 | 1 |
| IGHD3-22*01 | 20 | 1 |

| CDR3Length (All Naïve) | Count |
| --- | --- |
| 20 | 23 |
| 21 | 10 |
| 22 | 7 |
| 23 | 3 |
| 24 | 1 |
| 26 | 1 |

B: Long HCDR3s from Immunised Repertoires

| V | Average CDR3Length | Count |
| --- | --- | --- |
| IGHV4-4*02 | 20 | 1 |
| IGHV3-11*01 | 23 | 2 |
| IGHV3-7*01 | 21 | 6 |

| D | Average CDR3Length | Count |
| --- | --- | --- |
| IGHD2-2*02 | 22 | 2 |
| IGHD3-10*01 | 22 | 5 |

TABLE 2-continued

| | | |
|---|---|---|
| IGHD6-19*01 | 20 | 1 |
| IGHD1-26*01 | 20 | 1 |

| CDR3Length (All Immunised) | Count |
|---|---|
| 20 | 4 |
| 21 | 1 |
| 22 | 2 |
| 24 | 1 |
| 25 | 1 |

C: Long HCDR3s from Antigen-Specific Repertoires

| V | Average CDR3Length | Count |
|---|---|---|
| IGHV4-4*02 | 20 | 2 |
| IGHV1-3*01 | 21 | 3 |
| IGHV3-11*01 | 21 | 1 |
| IGHV3-7*01 | 22 | 1 |

TABLE 2-continued

| | | |
|---|---|---|
| IGHV1-8*01 | 22 | 2 |
| IGHV3-20*d01 | 22 | 1 |
| IGHV3-9*01 | 20 | 1 |

| D | Average CDR3Length | Count |
|---|---|---|
| IGHD2-2*02 | 22 | 1 |
| IGHD3-9*01 | 21 | 1 |
| IGHD3-10*01 | 21 | 9 |

| CDR3Length (All Antigen-Specific) | Count |
|---|---|
| 20 | 4 |
| 22 | 2 |
| 21 | 4 |
| 24 | 1 |

The invention claimed is:

1. A method of producing a polyclonal antibody comprising two or more antibodies directed against different epitopes of a pathogen comprising:
  (i) contacting at least a first mouse with a composition comprising two or more epitopes of said pathogen, wherein the genome of said mouse comprises:
    (a) an immunoglobulin heavy chain locus comprising one or more human VH gene segments, one or more human D gene segments and one or more human JH gene segments upstream of a constant region comprising an endogenous C segment, and wherein the heavy chain locus comprises human VH and/or human D gene segments capable of yielding CDRH-3s (third complementary determining regions of heavy chain) of 20 or more amino acids in length, wherein said one or more human VH gene segments is selected from the group consisting of: IGHV1-2*02, IGHV1-18*01, IGHV3-7*01, IGHV6-1*01 IGHV3-9*01 IGHV2-5*10 IGHV7-4-1*01 IGHV1-3*01 IGHV4-4*02 IGHV3-13*01 IGHV3-23*04 IGHV1-8*01 IGHV321*03 and IGHV3-11*01, and/or wherein said one or more human D gene segments is selected from the group consisting of: IGHD2-2*02, IGHD39*01, IGHD3-10*01, IGHD6-13*01, IGHD4-17*01, IGHD6-19*01, IGHD3-22*01 and IGHD1-26*01; and
    (b) an immunoglobulin light chain locus comprising one or more human VL gene segments selected from the group consisting of: a VλII gene family member, Vλ-VII 4A, Vλ-II 2.1, a Vλ-1 gene family member, a Vλ-3 gene family member, IGLVIS2, lalh2, lalvl, la3h3, κv325, a VκI gene family member, κI-15A (KL012), VκII family member, a VκIII family member, a VκI gene family member, VκII A2 (optionally the A2a allele), VκA27 (Humkv325) and a gene segment at least 80% identical thereto, and one or more human JL (light chain) gene segments upstream of a constant region at an endogenous mouse IgL locus;
  wherein the human gene segments in the heavy chain locus are operably linked to the constant region thereof, wherein the human gene segments in the light chain locus are operably linked to the constant region thereof, and wherein upon said contacting, the mouse is capable of producing an antibody comprising heavy chains produced by rearrangement of said heavy chain locus and light chains produced by rearrangement of said light chain locus;
  and
  (ii) isolating polyclonal antibodies comprising two or more antibodies directed to different epitopes of said pathogen from each said contacted mouse of step (i), thereby producing a polyclonal antibody mixture comprising two or more antibodies directed against different epitopes of the same pathogen, wherein said two or more antibodies have an CDRH-3 sequence of at least 20 amino acids in length.

2. The method of claim 1, wherein said method recited in step (i) is applied to at least a second mouse, and wherein said method recited in step (ii) comprises isolating polyclonal antibodies from each said contacted mouse and combining said antibodies.

3. The method of claim 1, wherein in the light chain locus of the genome of said mouse, the V gene segment repertoire of the light chain locus consists of one VL gene segment type, or a mutant thereof, wherein the VL gene segment is selected from said group of human VL gene segments recited in (b) and wherein said mutant thereof comprises up to 15 nucleotide changes from a human VL gene segment recited in (b).

4. The method of claim 1, wherein in (a) said constant region is a heavy chain endogenous mouse constant region and/or in (b) said constant region is a light chain endogenous mouse constant region.

5. The method of claim 1, wherein endogenous heavy and light immunoglobulin chain expression in said mouse is inactive.

6. The method of claim 2, wherein said first mouse is contacted with a first antigen of said pathogen and said second mouse is contacted with a second antigen of said pathogen, and said first and second antigens are different.

7. The method of claim 1, wherein the different epitopes of said pathogen are epitopes of the same antigen of the pathogen.

8. The method of claim 1, wherein the different epitopes of said pathogen are epitopes of different antigens of the pathogen.

9. The method of claim 1, wherein said composition comprising two or more epitopes of said pathogen comprises said pathogen.

10. The method of claim 1, wherein said composition comprising two or more epitopes of said pathogen comprises one or more antigens of said pathogen.

11. The method of claim 1, wherein the pathogen is a bacterial or viral infectious disease pathogen.

12. The method of claim 11, wherein said infectious disease pathogen is selected from the group consisting of cytomegalovirus (CMV), HIV, influenza virus, *E. coli, Neisseria meningitidis* and a herpes family virus.

\* \* \* \* \*